(12) United States Patent
Koshio et al.

(10) Patent No.: US 6,333,320 B1
(45) Date of Patent: Dec. 25, 2001

(54) HEXAHYDRO-1,4-DIAZEPINE DERIVATIVES OR SALTS THEREOF

(75) Inventors: Hiroyuki Koshio; Fukushi Hirayama; Tsukasa Ishihara; Masashi Funatsu; Tomihisa Kawasaki; Yuzo Matsumoto, all of Tsukuba (JP)

(73) Assignee: Yamanouchi Pharmaceutical Co., Tokyo (JP)

( * ) Notice: Subject to any disclaimer, the term of this patent is extended or adjusted under 35 U.S.C. 154(b) by 0 days.

(21) Appl. No.: 09/463,017

(22) PCT Filed: Jul. 22, 1998

(86) PCT No.: PCT/JP98/03267

§ 371 Date: Jan. 19, 2000

§ 102(e) Date: Jan. 19, 2000

(87) PCT Pub. No.: WO99/05124

PCT Pub. Date: Feb. 4, 1999

(30) Foreign Application Priority Data

Jul. 23, 1997 (JP) .................................................. 9-197587

(51) Int. Cl.⁷ .............................. A61K 31/55; A61P 7/02; C07D 243/08; C07D 401/04; C07D 405/12
(52) U.S. Cl. ............................................ 514/218; 540/575
(58) Field of Search .............................. 514/218; 540/575

(56) References Cited

U.S. PATENT DOCUMENTS

| | | | |
|---|---|---|---|
| 4,634,783 | 1/1987 | Fujii et al. | 549/475 |
| 5,478,945 | 12/1995 | Sato et al. | 548/195 |
| 5,576,343 | 11/1996 | Nagahara et al. | 514/422 |

FOREIGN PATENT DOCUMENTS 10-17549  1/1988 (JP) .

*Primary Examiner*—Brenda Coleman
(74) *Attorney, Agent, or Firm*—Finnegan, Henderson, Farabow, Garrett & Dunner, L.L.P.

(57) ABSTRACT

Hexahydro-1,4-diazepine derivatives represented by general formula (I); pharmaceutically acceptable salts thereof; and drugs containing the same as the active ingredient, such as activated blood coagulation factor X inhibitor, wherein A: phenylene, pyridylene, or the like; B: a 5- or 6-membered aryl or heteroaryl ring; X: —CO—, —CONH—, —CSNH—, —SO$_2$—, —SO$_2$NH—, or the like; Y: a bond or alkylene; R$^1$: hydrogen, alkyl, —Y—(hetero) aryl, or the like; R$^2$: hydrogen, alkoxy, —COOH, or the like; R$^3$: amidino or a group capable of being converted into amidino; and R$^4$, R$^5$: each independently hydrogen or lower alkyl.

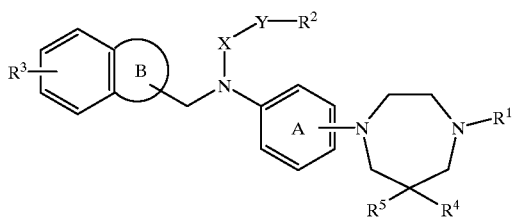

(I)

8 Claims, No Drawings

HEXAHYDRO-1,4-DIAZEPINE DERIVATIVES OR SALTS THEREOF

This application is a national stage entry under 35 U.S.C. § 371 of PCT/JP 98/03267 filed Jul. 22, 1998.

TECHNICAL FIELD

The present invention relates to hexahydro-1,4-diazepine derivatives or their salts which are useful as drugs, especially as an activated blood coagulation factor X inhibitor.

BACKGROUND OF THE INVENTION

Recently, thromboembolic disorders, such as myocardial infarction, cerebral thrombosis and peripheral arteriothrombosis, are increasing year by year with the popularization of Western life-styles and the increase in aged population, and there is much increasing social demand for the treatment of such disorders.

Anticoagulant therapy as well as adenolytic therapy and antiplatelet therapy is a part of medical therapy for treatment and prevention of thrombosis (Sogo Rinsho, 41: 2141–2145, 1989). In particular, anticoagulants for prevention of thrombosis indispensably require high safety for long-term administration and the ability of surely and appropriately expressing the anticoagulation activity.

However, the anticoagulating ability of warfarin potassium, which is only one oral anticoagulant now being popularly used in the world, is difficult to control because of the characteristic of itself based on the action and the mechanism thereof (*J. Clinical Pharmacology*, 32, 196–209, 1992; and *N. Eng. J. Med.*, 324 (26), 1865–1875, 1991), and the drug is extremely difficult to use in clinics.

It is known that thrombin acts to convert fibrinogen into fibrin in the final stage of coagulation, while deeply participating in the activation and the coagulation of platelets. At present, however, no oral thrombin inhibitor is commercially available because of its low bioavailability in oral administration and of its low safety (Biomed. Biochim. Acta, 44, 1201–1210, 1985).

On the other hand, the activated blood coagulation factor X is a key enzyme existing in the junction of intrinsic and extrinsic coagulation cascade reactions, and inhibiting this factor is more efficient than thrombin inhibition, and could bring about specific inhibition of coagulation systems (*THROMBOSIS RESEARCH* (19), 339–349, 1980).

As compounds having the ability of inhibiting the activated blood coagulation factor X, known are amidinonaphthylbenzene derivatives or their salts (JP-A-5-208946; *Thrombosis Haemostasis*, 71 (3), 314–319, 1994; *Thrombosis Haemostasis*, 72 (3), 393–396, 1994); and WO96/16940 discloses amidinonaphthyl derivatives of the following general formula or their salts.

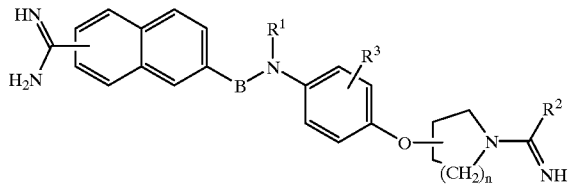

[In the formula, B represents a lower alkylene group, etc.; $R^1$ represents a hydrogen atom or a group of a formula, —A—W—$R^4$ [where A represents —CO—, —$SO_2$—, etc.; W represents a single bond or an —$NR^5$— group (where $R^5$ represents a hydrogen atom, a —$CONH_3$ group, etc.); $R^4$ represents an optionally-substituted lower alkyl group, etc.]; $R^2$ represents a lower alkyl group; $R^3$ represents a hydrogen atom, a halogen atom, etc.; and n=0 or 1.]

As so mentioned above, inhibitors for the activated blood coagulation factor X are more effective than thrombin inhibitors in anticoagulant therapy, and are expected to bring about specific inhibition of coagulation systems.

Accordingly, it is desired to create selective activated blood coagulation factor X inhibitors, which are different from the known compounds noted above in the chemical structure, can be orally administered and are more effective.

DISCLOSURE OF THE INVENTION

We, the present inventors have found that hexahydro-1,4-diazepine derivatives of the following general formula (I) or their salts, of which the chemical structure is characterized in that an amidinonaphthylmethyl group or the like is bonded to a phenyl group or a pyridyl group via a nitrogen atom and that the phenyl group or the pyridyl group is directly bonded to the nitrogen atom of the hexahydro-1,4-diazepine ring, have an excellent activity of inhibiting the activated blood coagulation factor X, and have completed the present invention.

Specifically, the invention relates to hexahydro-1,4-diazepine derivatives of the following general formula (I) or their salts, as well as pharmaceutical compositions, especially, activated blood coagulation factor X inhibitors comprising them as active ingredients:

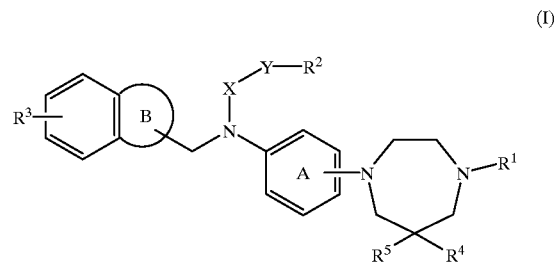

(I)

(In the formula, the symbols have the following meanings:

A: a phenylene or pyridylene group (which may be substituted),

B: forming a 5- or 6-membered aryl or heteroaryl,

X: a group of formula, —CO—, —CONH—, —CSNH—, —$SO_2$—, —$SO_2$NH—, or —$SO_2$N(-lower alkyl)-, Y: a bond or a lower alkylene group, $R^1$: a hydrogen atom, or a lower alkyl, —L-aryl, —L-heteroaryl, —L—COO—$R^6$, —L—CON(—$R^6$)—$R^7$, —C(=NH)—$NH_2$, or —C(=NH)-lower alkyl group, $R^2$: a hydrogen atom, an —O-lower alkyl, —COOH, —COO-lower alkyl, —$CONH_{21}$ —CONH-lower alkyl, or —CON—di-lower alkyl group, or an aryl or heteroaryl group (which may be substituted), $R^3$: an amidino group or a group capable of being converted into an amidino group in a living body, $R^4$, $R^5$: a hydrogen atom or a lower alkyl group, which may be the same or different, $R^6$, $R^7$: a hydrogen atom or a lower alkyl group, which may be the same or different, and L: a bond, or a lower alkylene group.)

The structure of the compounds of the invention is obviously different from that of the known compounds noted above in the basic skeleton, in which hexahydro-1,4-diazepinylphenyl (or hexahydro-1,4-diazepinyl-pyridyl) is bonded to the amidinonaphthylmethyl group via a nitrogen atom in the former, while the pyrrolidinyl- (or piperidinyl) oxyphenyl group is bonded to the amidinonaphthylmethyl group via a nitrogen atom in the latter.

Of the compounds of the invention, preferred are hexahydro-1,4-diazepine derivatives of the general formula (I), wherein the ring

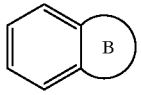

is naphthalene or benzofuran, or their salts, or hexahydro-1,4-diazepine derivatives where $R^4$ and $R^5$ are each a hydrogen atom, or their salts.

More preferred are hexahydro-1,4-diazepine derivatives of the general formula (I), wherein the ring

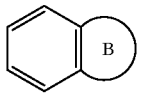

is naphthalene; A is a phenylene group (the phenylene group may be substituted with a substituent selected from a halogen atom, or an amino, cyano, nitro, —OH, —COOH, lower alkyl, —O-lower alkyl, or —COO-lower alkyl group) or a pyridyl group; $R^3$ is an amidino group; and $R^4$ and $R^5$ are each a hydrogen atom, or their salts.

Of the compounds of the invention, particularly preferred are hexahydro-1,4-diazepine derivatives of the general formula (I), wherein the ring

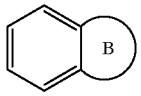

is naphthalene; A is a phenylene or pyridylene group; x is a group of formula, —CO—, —CSNH—, —SO$_2$—, or —SO$_2$NH—; $R^1$ is a hydrogen atom, or a lower alkyl, pyridyl, or —C(=NH)—CH$_3$ group; $R^2$ is a hydrogen atom, or a —COOH, —COO-lower alkyl, or tetrazolyl group; $R^3$ is an amidino group; and $R^4$ and $R^5$ are each a hydrogen atom, or their salts.

Of the compounds of the invention, most preferred are those enumerated below:

N-[4-(4-Acetimidoylhexahydro-1H-1,4-diazepin-1-yl)-phenyl]-N-[((7-amidino-2-naphthyl)methyl]-acetamide, Ethyl [N-[4-(4-acetimidoylhexahydro-1H-1,4-diazepin-1-yl) phenyl]-N-[(7-amidino-2-naphthyl)methyl]-sulfamoyl]acetate, Ethyl N-[N-[4-(4-acetimidoylhexahydro-1H-1,4-diazepin-1-yl)phenyl]-N-[(7-amidino-2-naphthyl)methyl]-sulfamoyl]glycinate, Ethyl N-[4-(4-acetimidoylhexahydro-1H-1,4-diazepin-1-yl)phenyl]-N-[(7-amidino-2-naphthyl)methyl] malonamate,

[N-[6-(4-Acetimidoylhexahydro-1H-1,4-diazepin-1-yl)-3-pyridyl]-N-[(7-amidino-2-naphthyl)methyl] sulfamoyl]acetic acid,

[N-[4-(4-Acetimidoylhexahydro-1H-1,4-diazepin-1-yl) phenyl]-N-[(7-amidino-2-naphthyl)methyl] sulfamoyl]-acetic acid, N-[4-(4-Acetimidoylhexahydro-1H-1,4-diazepin-1-yl) phenyl]-N-[(7-amidino-2-naphthyl)methyl] succinamic acid, Ethyl N-[4-(4-acetimidoylhexahydro-1H-1,4-diazepin-1-yl)-3-pyridyl]-N-[(7-amidino-2-naphthyl)methyl]-malonamate, Ethyl N-[4-(4-acetimidoylhexahydro-1H-1,4-diazepin-1-yl)-3-pyridyl]-N-[(7-amidino-2-naphthyl)methyl]-succinamate, N-[4-(4-Acetimidoylhexahydro-1H-1,4-diazepin-1-yl) phenyl]-N-[(7-amidino-2-naphthyl)methyl]thioamido-acetic acid, and N-[4-(4-Acetimidoylhexahydro-1H-1,4-diazepin-1-yl)-3-pyridyl]-N-[(7-amidino-2-naphthyl)methyl]succinamic acid.

Now, the compounds (I) of the invention are described in detail hereunder.

Unless otherwise specifically indicated, the term "lower" in the definition of the groups in the general formulae as referred to in the present specification means a linear or branched carbon chain having from 1 to 6 carbon atoms.

Accordingly, the "lower alkyl group" is an alkyl group having from 1 to 6 carbon atoms, including, for example, methyl, ethyl, propyl, butyl, pentyl and hexyl groups and their structural isomers such as isopropyl group, etc. Preferably, it is an alkyl group having from 1 to 4 carbon atoms, more preferably, a methyl or ethyl group.

The "lower alkylene group" is a linear or branched alkylene group having from 1 to 6 carbon atoms, including, for example, methylene, ethylene, trimethylene, tetramethylene, pentamethylene and hexamethylene groups and their structural isomers. Preferably, it is an alkylene group having from 1 to 3 carbon atoms, more preferably a methylene or ethylene group.

The "aryl" is an aromatic ring having from 6 to 14 carbon atoms, which may be substituted, including, for example, benzene, naphthalene, anthracene and phenanthrene groups. Preferably, it is benzene or naphthalene.

The "heteroaryl" is a 5- or 6-membered aromatic ring containing from one to four N, O or S atoms, or a bicycle having 5- or 6-membered aromatic rings fused with each other, each of which may be substituted, including, for example, furan, pyrrole, thiophene, imidazole, oxazole, thiazole, pyridine, pyrimidine, tetrazole, and naphthyridine. Most preferably, B is furan, $R^1$ is a pyridyl group, and $R^2$ is a tetrazolyl group.

The ring

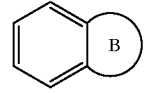

includes, for example, naphthalene, benzofuran, indole, benzothiophene, benzoimidazole, benzoxazole, benzothiazole, quinoline, and quinazoline. Preferably, it is benzoxazole or benzofuran.

The substituent for the "aryl group" or "heteroaryl group", or the substituent for the "phenylene or pyridylene group", is any substituent which is usually used as the substituent for aryl or heteroaryl, including, example, lower alkyl (the lower alkyl may be substituted with from one to four substituents selected from the group consisting of a halogen atom, and —O—lower alkyl, —COOH, amino, —NH-lower alkyl, and —N-di-lower alkyl groups), —OH, —O-lower alkyl, —COOH, —COO-lower alkyl, a halogen atom, amino, cyano, nitro, —NH—lower alkyl, and —N-di-lower alkyl groups; and the substituent for the phenylene group includes, for example, —S-lower alkyl, —SO-lower alkyl, —SO$_2$-lower alkyl, —CONH$_2$, and —O-lower alkylene-O— groups. These groups may further contain from one to three substituents. Preferably, it is a substituent selected from a halogen atom, and amino, cyano, nitro, —OH, —COOH, lower alkyl, —O-lower alkyl, and —COO-lower alkyl groups.

The "halogen atom" includes, for example, F, Cl, Br, and I atoms.

The "group capable of being converted into an amidino group in a living body" means a so-called prodrug group, which is an amidino group having —OH, —COO-lower alkyl group, or the like substituted thereon and can be removed under physiological conditions to form an amidino group. It includes, for example, —C(—NH$_2$)=N—OH, —C(—NH$_2$)=N—COO-lower alkyl, and other groups known in this art.

Depending on the type of the substituents therein, the compounds of the invention may include geometrical isomers and tautomers of cis-trans (or (E)-form and (Z)-form) ones based on the double bond therein, and optical isomers of (R)-form and (S)-form ones based on the asymmetric carbon atom therein. The invention shall encompass all of mixtures and isolated ones of those geometrical isomers, tautomers and optical isomers.

The compounds (I) of the invention may form acid-addition salts, and even salts with bases, depending on the type of the substituents therein. Those salts shall be pharmaceutically acceptable ones, and may include, for example, acid-addition salts with inorganic acids such as hydrochloric acid, hydrobromic acid, hydroiodic acid, sulfuric acid, nitric acid, phosphoric acid, etc.; or with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, propanesulfonic acid, toluene-sulfonic acid, aspartic acid, glutamic acid, etc.; as well as salts of inorganic bases of sodium, potassium, magnesium, calcium, aluminum etc., or with organic bases such as methylamine, ethylamine, ethanolamine, lysine, ornithine, etc.; ammonium salts, etc. Of these are preferred hydrochlorides, hydrobromides, sulfates, phosphates, fumarates, maleates, citrates, methanesulfonates, ethanesulfonates, propanesulfonates, and toluenesulfonates.

The invention further encompasses various hydrates, solvates and polymorphic crystals of the compounds (I) and their salts of the invention.

Naturally, the invention is not limited to the compounds described in the Examples to be mentioned hereunder, but shall include any and every type of hexahydro-1,4-diazepine derivatives of the general formula (I) or their salts.

(Production Method)

One typical method for producing the compounds (I) of the invention is mentioned below.

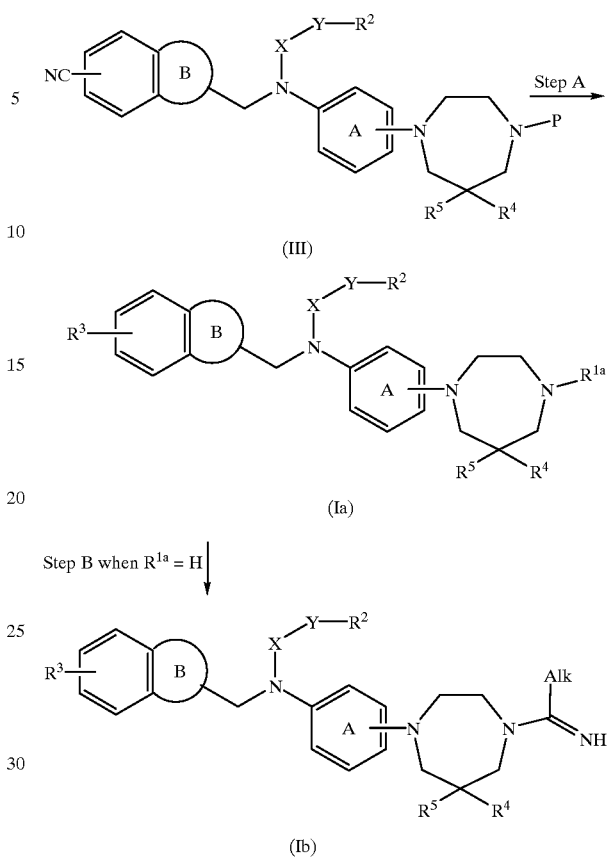

(In the formulae, A, B, R$^2$, R$^3$, R$^4$, X and Y have the same meanings as above; Alk represents a lower alkyl group; R$^{1a}$ represents a hydrogen atom or a pyridyl group; and P represents a pyridly group or anamino-protecting group.)

The amino-protecting group of P is not specifically limited, and may be any and every group generally used for protecting amino groups. For example, it includes—COO-Lower alkyl, —COO-lower alkyl-aryl, acyl, lower alkyl, -lower alkyl-aryl, SO$_2$-lower alkyl groups, ect.

[Step A]

Of the compounds of the invention, those (Ia) where R$^1$ is a hydrogen atom or a pyridyl group can be produced according to any of the methods (1) to (3) mentioned below.

(1) A method of converting a nitrile into an imidate, followed by condensing it with an amine:

A nitrile compound (III) is reacted with an alcohol such as methanol, ethanol or the like in the presence of hydrochloric acid gas at −40 to 0° C. to be converted into an imidate, which is then reacted with an amine or amine salt, such as ammonia, ammonium carbonate, ammonium chloride, ammonium acetate or the like. As a solvent, a solvent which is effective for the reaction, or an inert solvent is used. The inert solvent includes tetrahydrofuran (THF), N,N-dimethylformamide (DMF), dimethyl sulfoxide (DMSO), benzene, toluene, xylene, ethyl acetate, acetone, acetonitrile, dichloromethane, dichloroethane, chloroform, methanol, ethanol, isopropanol, mixtures thereof, etc.

(2) A method of converting a nitrile into a thioimidate via a thioamide, followed by condensing it with an amine:

First, a nitrile compound (III) is reacted with hydrogen sulfide in the presence of an organic base such as methylamine, triethylamine, pyridine, picoline, or the like, or is reacted with O,O-diethyl dithiophosphate in the presence of hydrogen chloride, thereby converting it into a thioamide. Next, the resulting thioamide is reacted with a lower alkyl halide such as methyl iodide, ethyl iodide, or the like, thereby converting it into a thioimidate, which is then reacted with an amine or amine salt, such as ammonia, ammonium carbonate, ammonium chloride, ammonium acetate, or the like. As a solvent, the above-described inert solvent is used. (3) A method of directly adding an amine, an amine salt, a metal amide, or a Grignard reagent to a nitrile:

To a nitrile compound (III), added is any reagent of ammonia, ammonium chloride combined with ammonia, ammonium thiocyanate, an alkylammonium thiocyanate, MeAl(Cl)NH$_2$, NaNH$_2$, (CH$_3$)$_2$NMgBr, or the like. The reaction can be carried out in an inert solvent such as that mentioned above or in the absence of a solvent. A base such as sodium hydride or an acid such as aluminum chloride, p-toluenesulfonic acid, etc. may be added as a catalyst, whereby the reaction may be greatly promoted. The reaction may be effected with cooling, or at room temperature, or under heating.

In the reaction of converting the nitrile into an amidino group, the amino-protecting group of P could not be removed as the case may be. In that case, the protecting group may be removed in any suitable method for further removing it to obtain the compound (Ia) of the invention.

Where the compound (III) has a —COO-alkyl group bonded thereto, the —COO-alkyl group may be converted into a —CONH$_3$ group during the amidination.

[Step B]

Of the compounds of the invention, those (Ib) where R$^1$ is a —C(=NH)-lower alkyl group can be synthesized by reacting the compound (Ia) of the invention, which is produced in the previous first step and which has a secondary amino group (R$^{1a}$=H) with an imidate compound in the presence of a base.

This reaction may be effected with cooling or under heating, in which is usable the above-described inert solvent. As the base, usable are organic bases such as N-methylmorpholine, triethylamine, trimethylamine, pyridine, picoline, lutidine, dimethylaniline, etc. and inorganic bases such as sodium hydroxide, potassium hydroxide, sodium hydrogencarbonate, etc.

Where the compound (Ib) has a —COO-alkyl group bonded thereto, the group may be converted into a carboxyl group through hydrolysis under basic, acidic or neutral conditions, as the case may be.

In the hydrolysis, employable is a base such as sodium hydroxide, potassium hydroxide, lithium hydroxide, barium hydroxide or the like under the basic conditions; an acid such as hydrochloric acid, sulfuric acid, Lewis acids, e.g., boron trichloride, p-toluenesulfonic acid, or the like under the acidic conditions; and a halide such as lithium iodide, lithium bromide, or the like, or an alkali metal salt of thiol or selenol, or iodotrimethylsilane, an enzyme such as esterase, or the like under the neutral conditions.

The reaction is effected generally at room temperature using an inert solvent such as that mentioned above, but in some cases, it requires cooling or heating the reaction system. The conditions may be suitably determined in any ordinary manner.

(Methods for Producing Starting Compounds)

Typical methods for producing starting compounds for the compounds (I) of the invention are mentioned below.

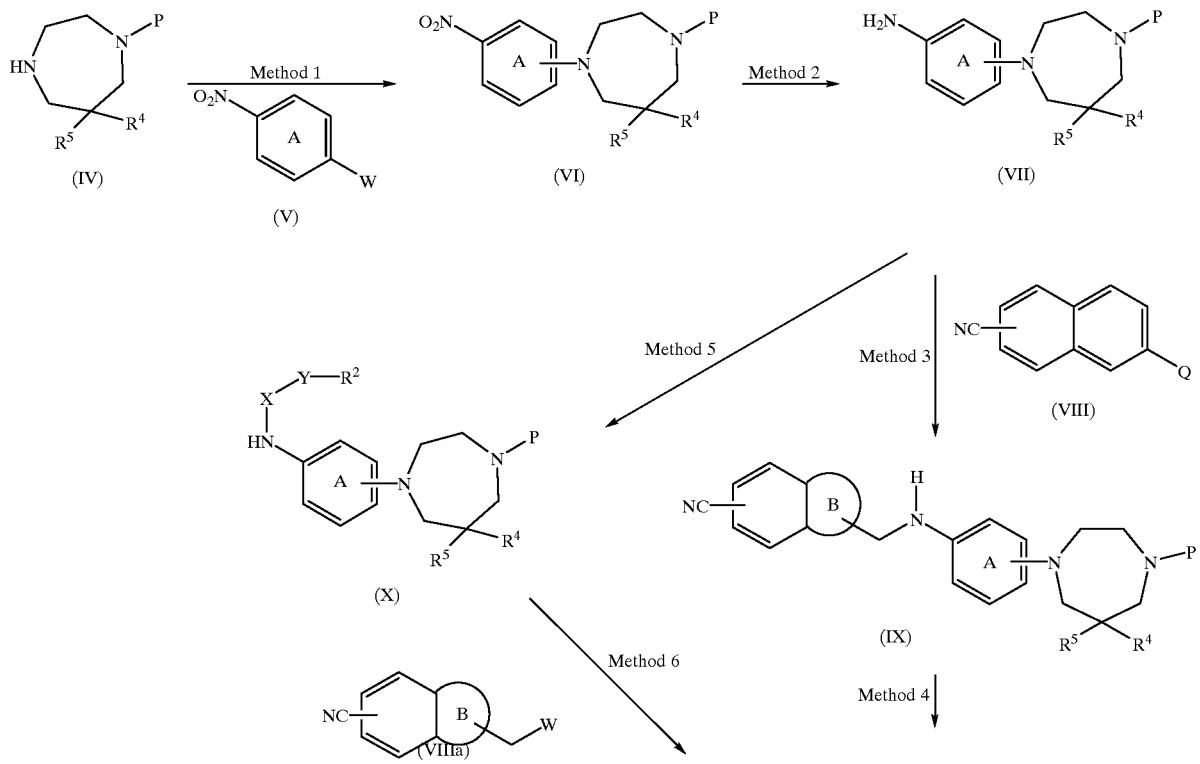

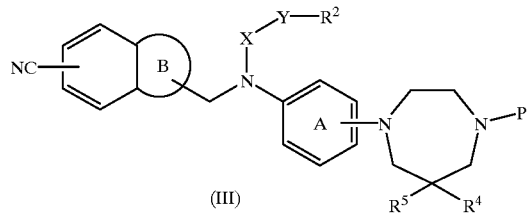

(III)

(In the formulae, A, B, R $R^2$, $R^4$, $R^5$, X, Y and P have the same meanings as above; W represents a halogen atom or an organic sulfonic acid residue; Q represents an aldehyde group or a group of formula, —$CH_2$-W; and P' represents P or a hydrogen atom.)

Method 1:

This is to react a hexahydro-1,4-diazepine derivative (IV) with a nitrobenzene or nitropyridine derivative (V) to give a compound (VI). This reaction is the same as ordinary substitution reaction, and may be effected in no solvent or in an inert organic solvent such as that mentioned above, at room temperature or under heating, or even under heating for reflux, optionally in the presence of an inorganic base such as that mentioned above. When P' is a hydrogen atom, a similar substitution reaction is further carried out by using chloropyridine, etc. to synthesize a compound (VI) where P is a pyridyl group. If desired, an amino-protecting group may be introduced into the compound formed herein, in any suitable method to give a compound (VI) where P is the amino-protecting group.

Method 2:

This is to obtain an amine compound (VII) from the nitro compound (VI). This reaction may be ordinary reduction, for which, for example, employed is method of using a metal such as zinc, tin or the like; a method of using a metal hydride such as $LiAlH_4$ or the like; or a catalytic reduction method of using palladium-carbon or the like. These methods may be effected in an inert solvent such as that mentioned above, at room temperature or under heating.

Method 3:

This is ordinary N-alkylation.

(i) Where the compound (VIII) is an alkyl halide or alkyl sulfonate:

The reaction is effected by stirring the compound (VII) and a reaction-corresponding amount of a compound (VIII) in an inert solvent such as that mentioned above with cooling or under heating. To promote the reaction, it is desirable to add a base such as that mentioned above.

(ii) Where the compound (VIII) is an aldehyde:

The reaction is reductive amination of reacting the compound (VII) with a corresponding aldehyde (VIII) and a reducing agent. As the reducing agent, for example, employable is any of sodium borohydride, sodium cyanoborohydride, sodium triacetoxyborohydride, etc. This reaction may be effected in an alcohol or an inert solvent such as that mentioned above while stirring with cooling or under heating (for reflux).

Method 4:

Starting compounds (III) can be produced according to any of the methods (a) to (c) mentioned below.

(a) Method for producing amide compounds (IIIa):

Of the starting compounds (III), amide compounds (IIIa) where X is —CO— can be synthesized through acylation of an amine (IX) with an active derivative of a carboxylic acid (for example, acid chloride, etc.).

Alternatively, amide compounds (IIIa) can also be synthesized through acylation of an amine (IX) and a carboxylic acid in the presence of a condensing agent. As the condensing agent, for example, favorably employed is any of N,N-dicyclohexylcarbodiimide (DCC), 1-ethyl-3-(3-(N,N-dimethylamino)propyl)carbodiimide, carbonyldi-imidazole, etc. In general, the reaction may be effected in an inert solvent such as that mentioned above, with cooling or at room temperature and depending on the type of the acylation, the reaction is effected under anhydrous conditions. Also, the reaction may be effected in the presence of a base such as that mentioned above or using the base as the solvent, thereby promoting the reaction.

(b) Method for producing urea compounds (IIIb):

Of the starting compounds (III), urea compounds (IIIb) where X is —CONH— can be synthesized by reacting an amine (IX) with an isocyanate derivative, or by reacting the amine (IX) with phosgene, diphosgene, triphosgene, or the like to give a carbamoyl chloride, followed by further reacting it with an amine derivative.

This reaction may be effected in an inert solvent such as that mentioned above with cooling or under reflux. The solvent may be suitably selected, depending on the type of the reaction.

The reaction may be effected in the presence of a base such as that mentioned above or using the base as the solvent, thereby promoting the reaction.

(c) Method for producing sulfonamide compounds or sulfamide compounds (IIIc):

Of the starting compounds (III), sulfonamide compounds or sulfamide compounds (IIIC) where $X^1$ is —$SO_2$— or —$SO_2NH$— can be synthesized by reacting the amine (IX) with a sulfonyl halide derivative or a sulfonic acid anhydride, generally in the presence of a base such as that mentioned above. This reaction may be effected in an inert solvent such as that mentioned above with cooling or under reflux. The solvent may be suitably selected, depending on the type of the reaction.

Method 5:

When X of the compound (VII) is a group of —CO—, —CONH—, —$SO_2$—, or —$SO_2NH$—, the compound (X) can be synthesized in a similar manner to that in the Methods 4(a) to (c) noted above. Regarding the reaction conditions including the reaction temperature and the solvent to be used, etc. referred to are those for the Methods 4(a) to (c) noted above.

Method 6:

In this method, the reaction of the compound (VIIIa) with the compound (X) to give compounds (III) is the same as that in the Method 3(i) noted above. Regarding the reaction conditions including the reaction temperature and the solvent to be used, etc. referred to are those for the Method 3(i) noted above.

The starting compounds for use in the invention may also be produced through any other known alkylation, oxidation, reduction and hydrolysis by combining them in any manner well known to those skilled in the art. For alkylation, for example, a sulfonamide compound may be reacted with a reaction-equivalent amount or an excess amount of an alcohol (e.g., methanol, ethanol, etc.) with stirring them in the presence of triphenylphosphine and diethyl azocarboxylate, in an inert solvent such as that mentioned above at room temperature or under heating to obtain alkyl-substituted sulfonamide compounds.

The compounds of the invention thus produced in the manner noted above may be isolated and purified in any known method of, for example, extraction, precipitation, fractional chromatography, fractional crystallization, recrystallization or the like, and may be formed into desired salts through ordinary salt formation.

Of the compounds of the invention, those having an asymmetric carbon atom may include optical isomers, which may be resolved in any ordinary method of, for example, fractional crystallization of recrystallizing them with suitable salts, column chromatography or the like.

Industrial Applicability

The compounds of the invention specifically inhibit the activated blood coagulation factor X, and have a strong anticoagulation activity. Accordingly, the compounds are useful as anticoagulants or as drugs for preventing and treating disorders to be induced by thrombi or emboli. The diseases for which the compounds of the invention are effective include those in cerebrovascular disorders such as cerebral infarction, cerebral thrombosis, cerebral embolism (*N Engl J Med*, 333, 1588–1593, 1995), acute and chronic myocardial infarction, unstable angina (*Thromb Haemost*, 74, 640–645, 1995), those in ischemic cardiopathy such as coronary thrombolysis, etc. (*Cardiovasc Res*, 28, 78–85, 1994; *J Am Coll Cardiol*, 28, 1858–1865, 1996), peripheral arterio-occlusion (*Fibrinolysis*, 7, 195–202, 1993), deep vein thrombosis (*Thromb Haemost*, 65, 257–262, 1991; *Thromb Res*, 71, 317–324, 1993), disseminated intravascular coagulation syndrome (*Thromb Haemost*, 72, 393–396, 1994), thrombophilia after artificial vasoformation and after artificial valvoplasty, re-occlusion and re-constriction after coronary bypass operation (*Circulation*, 84, 1741-1748, 1991), re-occlusion and re-constriction after PTCA (*Circulation*, 89, 1262–1271, 1994; *Circulation*, 93, 1542–1548, 1996), thrombophilia during extracorporeal circulation (*Thromb Haemost*, 74, 635–639, 1995), etc. Based on their activity to inhibit the activated blood coagulation factor X and their activity to inhibit the growth of influenza viruses, the compounds of the invention are expected to be usable for preventing infection with influenza viruses and for curing influenza (JP-A-6-22971).

The excellent activity of the compounds of the invention to inhibit the activated blood coagulation factor X was confirmed by the test methods mentioned below.

1) Method of measuring the time for blood coagulation with the human activated blood coagulation factor X:

The human activated blood coagulation factor X (Cosmo-Bio Co.) was dissolved in 0.05 M tris-HCl buffer (pH=7.40) to prepare its solution of 0.05 units/ml. Blood was collected in 3.8% sodium citrate to be 1/10 by volume, and centrifuged at 3,000 rpm for 10 minutes to separate human plasma therefrom. 90 $\mu$l of the thus-prepared human plasma, 10 $\mu$l of a test compound as diluted with physiological saline, and 50 $\mu$l of the solution of the activated blood coagulation factor X were kept warmed at 37° C. for 3 minutes, to which was added 100 $\mu$l of a solution of 20 mM $CaCl_2$, and the time for blood coagulation in the system was measured.

To measure the coagulation time, used was Amelung's KC4A. The dose of the test compound for 2-time prolongation of the coagulation time (hereinafter referred to as CT2) was calculated on the basis of the coagulation time for the control to which was added 10 $\mu$l of physiological saline with no test compound. The results are shown in Table 1.

TABLE 1

| Example No. | Test for measuring coagulation time with the human activated blood coagulation factor X, CT2 ($\mu$M) |
|---|---|
| 17 | 0.092 |
| 22 | 0.111 |
| 23 | 0.110 |
| 24 | 0.152 |
| 32 | 0.089 |
| 33 | 0.098 |
| 36 | 0.069 |
| 72 | 0.119 |
| 73 | 0.224 |
| 75 | 0.095 |
| 84 | 0.134 |
| Control compound | 0.590 |

*) Control compound: A compound of Example 52 of JP-A-5-208946

It has been verified that the compounds of the invention specifically inhibit the human activated blood coagulation factor X, and, while prolonging the coagulation time even at low concentrations, exhibit an excellent anticoagulation activity.

2) Method of measuring the coagulation time for mice in exo vivo (intravenous administration):

To test animals of male ICR mice (20 to 30 g, SLC Co.) that had been fed with nothing for 12 hours or longer, a solution of a test compound having been dissolved in physiological saline was intravenously administered only once through their tail vein. One minute after the administration, 0.6 ml of blood was collected from the animals which were anesthetized with diethyl ether, through their posterior artery in 3.8% sodium citrate to be 1/10 by volume, and centrifuged at 3,000 rpm for 10 minutes to separate plasma therefrom. The extrinsic coagulation time (PT) and the intrinsic coagulation time (APTT) for this plasma were measured according to the following methods a) and b), respectively.

a) Extrinsic coagulation time (PT):

Tissue thromboplastin (54 mg/vial, freeze-dried powder by Ortho Co.) was dissolved in 2.5 ml of distilled water, and pre-warmed at 37° C. 50 $\mu$l of the plasma prepared in the above was kept warmed at 37° C. for 1 minute, to which was added 50 $\mu$l of the thromboplastin solution, and the coagulation time was measured. To measure the coagulation time, used was Amelung's KC4A. The coagulation time for the control to which had been applied 50 $\mu$l of physiological saline with no test compound was also measured. Based on the value of the coagulation time for the control of being 1, obtained was the relative activity of the test compound. b) Intrinsic coagulation time (APTT):

50 $\mu$l of active thrombofacs (Ortho Co.) and 50 $\mu$l of the plasma prepared in the above were kept warmed at 37° C. for 3 minutes, to which was added 50 $\mu$l of a solution of 20 mM $CaCl_2$ having been previously warmed at 37° C., and the coagulation time was measured. To measure the coagulation time, used was Amelung's KC4A. The coagulation time for the control to which had been administered physiological saline with no test compound was also measured. Based on the value of the coagulation time for the control of being 1, obtained was the relative activity of the test compound. The dose dependency of the anticoagulation activity of the compounds of the invention and also the time-dependent change in the activity thereof were also studied in the same manner as above, in which the dose and the time for blood collection were varied.

The data obtained in those experiments verified that the intravenous administration of the compounds of the invention well prolongs the coagulation time.

3) Method of measuring the coagulation time for mice in exo vivo (oral administration):

The same test animals as in 2) were further tested in the same manner as above, except that the solution of a test compound was orally administered in a forced manner through a gastric tube inserted thereinto, in place of the single intravenous administration in 2), and that blood was collected from each test animal in 30 minutes after the oral administration.

The test data obtained herein verified that the oral administration of the compounds of the invention well prolongs the coagulation time.

4) Method of measuring the coagulation time for crab-eating macaque in exo vivo (oral administration):

To test animals of male cynomolgus monkey (3 to 6 kg, Hamri Co.) that had been fed with nothing for 12 hours or longer, a solution or suspension of a test compound having been dissolved in physiological saline or suspended in a solution of 0.5% methyl cellulose was orally administered in a forced manner through a gastric tube inserted thereinto. 3 ml of blood was collected from the thus-treated animals not being anesthetized, through their femoral vein at predetermined time intervals, in 3.8% sodium citrate to be 1/10 by volume, and centrifuged at 3,000 rpm for 10 minutes to separate human plasma therefrom. The extrinsic coagulation time (PT) and the intrinsic coagulation time (APTT) for this plasma were measured according to the same methods as in 2).

The test data obtained herein verified that the oral administration of the compounds of the invention exhibits good bioavailability and has a superior function for prolonging the coagulation time.

Pharmaceutical compositions comprising, as the active ingredient, one or more of the compounds of formula (I) and their pharmaceutically acceptable salts of the invention can be formulated along with ordinary pharmaceutical carriers, vehicles and other additives into tablets, powders, fine granules, granules, capsules, pills, liquid preparations, injections, suppositories, ointments, cataplasms, and the like, and are administered orally or parenterally.

The clinical dose of the compounds of the invention may be suitably determined, depending on the conditions, the body weight, the age and the sex of the patients to which they are administered, but is, in general, from 0.1 to 500 mg/adult/day for oral administration, and from 0.01 to 100 mg/adult/day for parenteral administration. This may be administered to the patients all at a time, or may be divided into a few portions for administration in different times. Since the dose may vary depending on various conditions, a smaller dose than the defined range may well be employed, as the case may be.

As the solid composition for oral administration of the compounds of the invention, employed are tablets, powders, granules, etc. The solid composition of those types comprises one or more active substances along with at least one inert diluent, such as lactose, mannitol, glucose, hydroxypropyl cellulose, microcrystalline cellulose, starch, polyvinyl pyrrolidone, meta-silicic acid, and magnesium aluminate. In an ordinary manner, the composition may contain any other additives except the inert diluents noted above, for example, a lubricant such as magnesium stearate, a disintegrator such as calcium cellulose glycolate, a stabilizer such as lactose, and a solubilizer or dissolution promoter such as glutamic acid or aspartic acid. If desired, the tablets and pills may be coated with a film of gastric or enteric substances such as sucrose, gelatin, hydroxypropyl cellulose, hydroxypropylmethyl cellulose phthalate, etc.

The liquid composition for oral administration includes, for example, pharmaceutically acceptable emulsions, solutions, suspensions, syrups, elixirs, and the like, which contain ordinary inactive diluents such as purified water and ethyl alcohol. In addition to the inert diluents, those compositions may further contain pharmaceutical aids such as solubilizers, dissolution promoters, wetting promoters, suspension promoters, and also sweeteners, flavorings, aromas, and preservatives.

The injection for parenteral administration includes, for example, germ-free, aqueous or non-aqueous solutions, suspensions and emulsions. The diluent for the aqueous solutions and suspensions includes, for example, distilled water and physiological saline for injections. The diluent for the non-aqueous solutions and suspensions includes, for example, propylene glycol, polyethylene glycol, vegetable oils such as olive oil, alcohols such as ethyl alcohol, Polysolvate 80 (trade name), etc. Those compositions may further contain additives such as isotonicating promoters, preservatives, wetting promoters, emulsifiers, dispersants, stabilizers (e.g., lactose), solubilizers, dissolution promoters, etc. The compositions are sterilized by filtering them through bacteria-trapping filters, or by adding microbicides thereto, or by exposing them to radiations. The germ-free, solid compositions thus produced may be dissolved in germ-free water or in germ-free solvents for injection, before using them.

Where the compounds of the invention have low solubility, they may be processed for solubilization. For the solubilization treatment, employable are any known methods applicable to pharmaceutical preparations. For example, employed are a method of adding surfactants (e.g., polyoxyethylene-hardened castor oils, etc.) to the compounds; and a method of forming solid dispersions comprising the compounds and solubilizers (for example, water-soluble polymers, e.g., hydroxypropylmethyl cellulose, etc., and enteric polymers, e.g., carboxymethylethyl cellulose). If desired, further employed are a method of forming soluble salts, and a method of forming clathrate compounds with cyclodextrin or the like. The solubilizing means may be suitably modified depending on the chemicals to be processed therewith ("Recent Pharmaceutical Techniques and Their Applications", in the *Journal of Medicines*, 157–159, 1983; and *Pharmacological Monograph* No. 1, "Bioavailability", published by Soft Science Co., 78–82, 1988). Of those, preferred is the method of forming solid dispersions of chemicals and solubilizers to improve the solubility of the chemicals (JP-A-56-49314; FR 2,460,667).

BEST MODE FOR CARRYING OUT THE INVENTION

Now, the method for producing the compounds of the invention is described concretely hereunder, with reference to the following Examples of demonstrating the production of the compounds. It is to be construed that the compounds of the invention are not limited to those described in the following Examples but that the invention encompasses all of the compounds represented by the foregoing general formula (I) and their salts, hydrates, solvates, tautomers, optical isomers and polymorphic crystals. Some starting compounds for the compounds of the invention are novel, and the method for producing such novel compounds is demonstrated in the following Reference Examples.

REFERENCE EXAMPLE 1

1.8 g of 1-t-butoxycarbonylhexahydro-1H-1,4-diazepine was dissolved in 10 ml of DMF, to which were added 1.62 g of 4-fluoronitrobenzene and 1.84 g of potassium carbonate, and stirred at 90° C. for 13 hours. After the reaction mixture was cooled, ethyl acetate was added thereto, and the mixture was washed with water and saturated saline in that order, dried over anhydrous sodium sulfate, and then evaporated. The resulting residue was dissolved in 10 ml of 1,4-dioxane, to which was added 4 ml of 4 N hydrochloric acid (in 1,4-dioxane), and stirred at 80° C. for 16 hours. The reaction mixture was cooled, and then evaporated. 50 ml of diethyl ether was added to the resulting residue, and then filtered to obtain 2.11 g of 1-(4-nitrophenyl)hexahydro-1H-1,4-diazepine dihydrochloride.

REFERENCE EXAMPLE 2

2 g of the compound obtained in Reference Example 1 was dissolved in 20 ml of isoamyl alcohol, to which were added 1.02 g of 4-chloropyridine hydrochloride and 2.57 g of sodium hydrogencarbonate, and heated under reflux for 24 hours. Then, 500 mg of 4-chloropyridine hydrochloride was added to the reaction mixture, and further heated under reflux for 24 hours. The reaction mixture was cooled, and then evaporated. Chloroform was added to the resulting residue, which was then washed with water and saturated saline in that order, dried over anhydrous sodium sulfate, and then evaporated. The resulting residue was dissolved in 30 ml of 1,4-dioxane, to which were added 0.95 ml of triethylamine and 1.48 g of di-t-butyl dicarbonate, and stirred at room temperature for 12 hours. The reaction mixture was evaporated, and the resulting residue was purified through silica gel column chromatography using an eluent solvent of chloroform/methanol (10/1) to obtain 1.94 mg of 1-(4-nitrophenyl)-4-(4-pyridyl)hexahydro-1H-1,4-diazepine.

REFERENCE EXAMPLE 3

100 mg of a 10% palladium-carbon powder was suspended in 1 ml of methanol, to which was added a solution of 460 mg of the compound obtained in Reference Example 2 and dissolved in 20 ml of methanol, and stirred in a hydrogen atmosphere at room temperature for 8 hours. The reaction mixture was filtered through Celite, and the filtrate was evaporated. The resulting residue was dissolved in 20 ml of 1,2-dichloroethane, to which were added 290 mg of 7-formyl-2-naphthalene-carbonitrile, 0.41 ml of acetic acid and 458 mg of sodium triacetoxyborohydride, and stirred at room temperature for 21 hours. Chloroform was added to the reaction mixture, which was then washed with aqueous saturated sodium hydrogencarbonate, water and saturated saline in that order, then dried over anhydrous sodium sulfate, and then evaporated. The resulting residue was purified through silica gel column chromatography using an eluent solvent of chloroform/methanol (10/1) to obtain 429 mg of 7-[[4-[4-(4-pyridyl)hexahydro-1H-1,4-diazepin-1-yl]anilino]methyl]-2-naphthalenecarbonitrile.

REFERENCE EXAMPLE 4

420 mg of the compound obtained in Reference Example 3 was dissolved in 10 ml of 1,2-dichloromethane, to which were added 0.2 ml of triethylamine and 0.11 ml of methanesulfonyl chloride, and stirred at room temperature for 12 hours. Chloroform was added to the reaction mixture, which was then washed with aqueous saturated sodium hydrogencarbonate, water and saturated saline in that order, dried over anhydrous sodium sulfate, and then evaporated. The resulting residue was purified through silica gel column chromatography using an eluent solvent of chloroform/ methanol (20/1) to obtain 340 mg of N-[(7-cyano-2-naphthyl)methyl]-N-[4-[4-(4-pyridyl)hexahydro-1H-1,4-diazepin-1-yl]phenyl]-methanesulfonamide.

In the same manner as in Reference Example 4, obtained were compounds of Reference Examples 5 and 6 shown in Table 10.

REFERENCE EXAMPLE 7

3.0 g of 4-fluoro-3-methylnitrobenzene was dissolved in 20 ml of DMF, to which were added 5.81 g of hexahydro-1H-1,4-diazepine and 3.94 g of potassium carbonate, and stirred at 90° C. for 4 hours.

After the reaction mixture was cooled, chloroform was added thereto, and the mixture was washed with water and saturated saline in that order, dried over anhydrous sodium sulfate, and then evaporated. The resulting residue was purified through silica gel column chromatography using an eluent solvent of chloroform/methanol (5/1) to obtain 3.78 g of 1-(2-methyl-4-nitrophenyl)hexahydro-1H-1,4-diazepine.

In the same manner as in Reference Example 7, obtained were compounds of Reference Examples 8 to 10 shown in Table 7.

REFERENCE EXAMPLE 11

5.8 g of 5-(hexahydro-1H-1,4-diazepin-1-yl)-2-nitrobenzonitrile obtained in Reference Example 10 was dissolved in 20 ml of ethanol, to which was added aqueous 6 M sodium hydroxide, and heated under reflux for 15 hours. The reaction mixture was cooled, neutralized with concentrated hydrochloric acid, and then evaporated. The resulting residue was dissolved in 150 ml of methanol, to which was added 10 ml of sulfuric acid, and then heated under ref lux for 2 days. The reaction mixture was cooled, and then evaporated. The resulting residue was dissolved in a small amount of water, and then neutralized with sodium carbonate. Chloroform was added to this, which was then washed with saturated saline, dried over anhydrous sodium sulfate, and then evaporated to obtain 4.21 g of methyl 5-(hexahydro-1H-1,4-diazepin-1-yl)-2-nitrobenzoate.

REFERENCE EXAMPLE 12

21.4 g of hexahydro-1H-1,4-diazepine was dissolved in 214 ml of DMF, to which were added 10.1 g of 4-fluoronitrobenzene and 19.7 g of potassium carbonate, and stirred at 90° C. for 7 hours. The reaction mixture was evaporated, and chloroform was added to the resulting residue, which was then washed with aqueous 10% potassium hydrogencarbonate and saturated saline in that order, dried over anhydrous magnesium sulfate, and then evaporated to remove the solvent. The resulting residue was dissolved in 210 ml of 1,2-dichloroethane, to which were added 86.5 g of triethylamine and 93.4 g of di-t-butyl dicarbonate, and stirred at room temperature for 13 hours. The reaction mixture was washed with water, dried over anhydrous sodium sulfate, and then evaporated. The resulting residue was washed with diethyl ether to obtain 14.12 g of 4-t-butoxycarbonyl-1-(4-nitrophenyl)hexahydro-1H-1,4-diazepine.

In the same manner as in Reference Example 12, obtained were compounds of Reference Examples 13 and 14 shown in Table 8.

RERERENCE EXAMPLE 15

3.7 g of the compound obtained in Reference Example 7 was dissolved in 50 ml of 1,4-dioxane, to which were added 3.23 ml of triethylamine and 5.2 g of di-t-butyl dicarbonate, and stirred at room temperature for 90 minutes. The reaction mixture was evaporated, and chloroform was added to the resulting residue. This was washed with water and saturated saline in that order, dried over anhydrous sodium sulfate, and then evaporated. The resulting residue was purified through silica gel column chromatography using an eluent solvent of chloroform/methanol (50/1) to obtain 7.64 g of 4-t-butoxycarbonyl-1-(2-methyl-4-nitrophenyl)hexahydro-1H-1,4-diazepine.

In the same manner as in Reference Example 15, obtained were compounds of Reference Examples 16 to 18 shown in Table 8.

REFERENCE EXAMPLE 19

14.12 g of 4-t-butoxycarbonyl-1-(4-nitrophenyl)-hexahydro-1H-1,4-diazepine obtained in Reference Example 12 was suspended in 44 ml of ethanol, to which was added 700 mg of 10% palladium-carbon, and stirred in a hydrogen atmosphere at room temperature for 16 hours. The reaction mixture was filtered, and then evaporated. The resulting residue was dissolved in 440 ml of 1,2-dichloroethane, to which were added 7.95 g of 7-formyl-2-naphthalenecarbonitrile, 26 ml of acetic acid and 18.5 g of sodium triacetoxyborohydride in that order, and stirred at room temperature for 2 hours. 0.8 g of 7-formyl-2-naphthalenecarbonitrile and 1.9 g of sodium triacetoxyborohydride were added to this, and further stirred for 1 hour. 0.8 g of 7-formyl-2-naphthalenecarbonitrile and 1.9 g of sodium tri-acetoxyborohydride were further added to this, and still further stirred for 2 hours. The reaction mixture was washed with aqueous 10% potassium carbonate and saturated saline in that order, dried over anhydrous sodium sulfate, and then evaporated. The resulting residue weighed 25.01 g. 7.04 g of this was purified through silica gel column chromatography using an eluent solvent of hexane/ethyl acetate (3/1) to obtain 4.45 g of 7-[[4-(4-t-butoxycarbonylhexahydro-1H-1,4-diazepin-1-yl)anilino]methyl]-2-naphthalenecarbonitrile.

REFERENCE EXAMPLE 20

2.1 g of the compound obtained in Reference Example 15 was dissolved in 10 ml of methanol, to which were added 300 mg of 10% palladium-carbon and 2.1 g of ammonium formate, and stirred at room temperature for 5 hours.

The reaction mixture was filtered through Celite, and the filtrate was evaporated. Chloroform was added to the resulting residue, which was then washed with water and saturated saline in that order, dried over anhydrous sodium sulfate, and then evaporated. The resulting residue was dissolved in 20 ml of 1,2-dichlroethane, to which were added 835 mg of 7-formyl-2-naphthalenecarbonitrile, 1.28 ml of acetic acid and 1.5 g of sodium triacetoxyborohydride in that order, and stirred at room temperature for 14 hours. Chloroform was added to the reaction mixture, which was then washed with aqueous saturated sodium hydrogencarbonate, water and saturated saline in that order, dried over anhydrous sodium sulfate, and then evaporated. The resulting residue was purified through silica gel column chromatography using an eluent solvent of chloroform/methanol (30/1) to obtain 1.94 g of 7-[[4-( 4-t-butoxycarbonylhexahydro-1H-1,4-diazepin-1-yl)-3-methylanilino]methyl]-2-naphthalenecarbonitrile.

REFERENCE EXAMPLE 21-1

2.1 g of 1-t-butoxycarbonyl-4-(2-chloro-4-nitro-phenyl) hexahydro-1H-1,4-diazepine obtained in Reference Example 16 was dissolved in 10 ml of a 4 N hydrochloric acid-1,4-dioxane solution, and stirred at 80° C. for 2 hours. The reaction mixture was evaporated. Chloroform was added to the resulting residue, which was then washed with aqueous saturated sodium hydrogencarbonate, water and saturated saline in that order, dried over anhydrous sodium sulfate, and then evaporated.

The resulting residue was dissolved in 20 ml of 1,2-dichloroethane, to which were added 0.6 ml of benzaldehyde, 1.65 ml of acetic acid and 1.9 g of sodium triacetoxyborohydride, and stirred at room temperature for 17 hours. Chloroform was added to the reaction mixture, which was then washed with aqueous saturated sodium hydrogencarbonate, water and saline in that order, dried over anhydrous sodium sulfate, and then evaporated.

The resulting residue was purified through silica gel column chromatography using an eluent solvent of chloroform/methanol (40/1) to obtain 1.47 g of 4-benzyl-1-(2-chloro-4-nitrophenyl)hexahydro-1H-1,4-diazepine.

REFERENCE EXAMPLE 21-2

1.4 g of the compound obtained in Reference Example 21-1 was dissolved in 20 ml of ethanol and 20 ml of water, to which were added 2.26 g of reduced iron and 108 mg of ammonium chloride, and heated under reflux for 3 hours. The reaction mixture was cooled, filtered through Celite, and then evaporated.

Chloroform was added to the resulting residue, which was then washed with aqueous saturated sodium hydrogencarbonate, water and saturated saline in that order, dried over anhydrous sodium sulfate, and then evaporated. The resulting residue was dissolved in 20 ml of 1,2-dichloroethane, to which were added 684 mg of 7-formyl-2-naphthalenecarbonitrile, 1.05 ml of acetic acid and 1.24 g of sodium triacetoxyborohydride, and stirred at room temperature for 24 hours.

Chloroform was added to the reaction mixture, which was then washed with aqueous saturated sodium hydrogencarbonate, water and saturated saline in that order, dried over anhydrous sodium sulfate, and then evaporated. The resulting residue was purified through silica gel column chromatography using an eluent solvent of chloroform/methanol (50/1) to obtain 1.61 g of 7-[[4-(4-benzylhexahydro-1H-1,4-diazepin-1-yl)-3-chloro-anilino]methyl]-2-naphthalenecarbonitrile.

REFERENCE EXAMPLE 21-3

642 mg of the compound obtained in Reference Example 21-2 was dissolved in 20 ml of 1,2-dichloroethane, to which was added 1.44 ml of 1-chloroethyl chloroformate, and stirred at 90° C. for 16 hours. The reaction mixture was cooled, and then evaporated. The resulting residue was dissolved in 20 ml of methanol, and heated under reflux for 2 hours. The reaction mixture was cooled, and then evaporated. The resulting residue was dissolved in 20 ml of 1,4-dioxane, to which were added 270 mg of di-t-butyl dicarbonate and 0.21 ml of triethylamine, and stirred at room temperature for 7 hours.

The reaction mixture was evaporated, and the resulting residue was purified through silica gel column chromatography using an eluent solvent of hexane/ethyl acetate (4/1) to obtain 298 mg of 7-[[4-(4-t-butoxycarbonylhexahydro-1H-1,4-diazepin-1-yl)-3-chloro-anilino]methyl]-2-naphthalenecarbonitrile. In the same manner as in Reference Example 19, obtained were compounds of Reference Examples 22 and 23 shown in Table 9.

REFERENCE EXAMPLE 24

400 mg of 7-[[4-(4-t-butoxycarbonylhexahydro—1H-1,4-diazepin-1-yl)anilino]methyl]-2-naphthalenecarbo-nitrile obtained in Reference Example 19 was dissolved in 5 ml of 1,2-dichloroethane, and stirred at 30° C. 208 mg of pyridine and 201 mg of methanesulfonyl chloride were added to this, and stirred at room temperature for 12 hours. Chloroform was added to the reaction mixture, which was then washed with aqueous saturated sodium hydrogencarbonate, water, aqueous 10% citric acid and water in that order, dried over anhydrous sodium sulfate, and then evaporated. The resulting residue was recrystallized from methanol to obtain 342 mg of N-[4-(4-t-butoxycarbonylhexahydro-1H-1,4-diazepin-1-yl)-phenyl]-N-[(7-cyano-2-naphthyl)methyl] methanesulfonamide.

In the same manner as in Reference Example 24, obtained were compounds of Reference Examples 25 to 35 and Reference Example 40 shown in Table 10.

REFERENCE EXAMPLE 36

509 mg of the compound obtained in Reference Example 19 was dissolved in 5 ml of 1,2-dichloroethane, to which was added 401 mg of ethoxycarbonyl isocyanate, and stirred at room temperature for 3 hours. Aqueous 10% citric acid was added to the reaction mixture, which was then extracted with chloroform. The organic layer was dried over anhydrous sodium sulfate, and then evaporated. The resulting residue was purified through silica gel column chromatography using an eluent solvent of ethanol/chloroform (2/98) to obtain 637 mg of ethyl N-[N-[4-(4-t-butoxycarbonylhexahydro-1H-1,4-diazepin-1-yl)phenyl]-N-[(7-cyano-2-naphthyl)methyl]carbamoyl]-carbamate.

REFERENCE EXAMPLE 37

1.62 g of 4-t-butoxycarbonyl-1-(2-fluoro-4-nitro-phenyl) hexahydro-1H-1,4-diazepine obtained in Reference Example 13 was suspended in 48 ml of ethanol, to which was added 160 mg of 10% palladium-carbon, and stirred in a hydrogen atmosphere at room temperature for 2 hours. The reaction mixture was filtered, and then evaporated. The resulting residue weighed 1.62 g. 0.61 g of this was dissolved in 20 ml of 1,2-dichloroethane, to which were added 357 mg of 7-formyl-2-naphthalenecarbonitrile, 1.2 g of acetic acid and 823 mg of sodium triacetoxy-borohydride in that order, and stirred at room temperature for 2 hours. The reaction mixture was washed with aqueous 10% sodium carbonate and saturated saline in that order, dried over anhydrous sodium sulfate, and then evaporated. The resulting residue was dissolved in 20 ml of 1,2-dichloroethane, to which were added 467 mg of pyridine and 560 mg of ethyl chlorosulfonylacetate at 0° C., and stirred for 1 hour. One ml of ethanol was added to this, and stirred for 1 hours, and then, the reaction mixture was concentrated. The resulting residue was purified through silica gel column chromatography using an eluent solvent of hexane/ethyl acetate (3/1) to obtain 1.08 g of ethyl [N-[4-(4-t-butoxycarbonyl-hexahydro-1H-1,4-diazepin-1-yl)-3-fluorophenyl]-N-[(7-cyano-2-naphthyl)methyl]sulfamoyl]acetate.

In the same manner as in Reference Example 37, obtained was a compound of Reference Example 38 shown in Table 10.

REFERENCE EXAMPLE 39

1.7 g of t-butyl N-[N-[4-(4-t-butoxycarbonyl-hexahydro-1H-1,4-diazepin-1-yl)phenyl]-N-[(7-cyano-2-naphthyl) methyl]sulfamoyl]carbamate obtained in Reference Example 27 was dissolved in 20 ml of DMF, to which were added 0.44 ml of ethyl bromoacetate and 543 mg of potassium carbonate, and stirred at room temperature for 24 hours. Chloroform was added to the reaction mixture, which was then washed with water and saturated saline in that order, dried over anhydrous sodium sulfate, and then evaporated. The resulting residue was purified through silica gel column chromatography using an eluent solvent of chloroform/methanol (30/1) to obtain 1.68 g of ethyl N-[N-[4-(4-t-butoxycarbonylhexahydro-1H-1,4-diazepin-1-yl) phenyl]-N-[(7-cyano-2-naphthyl)methyl]sulfamoyl]-N-t-butoxycarbonylglycinate.

EXAMPLE 1

330 mg of N-[(7-cyano-2-naphthyl)methyl]-N-[4-[4-(4-pyridyl)hexahydro-1H-1,4-diazepin-1 -yl]phenyl]-methanesulfonamide obtained in Reference Example 4 was dissolved in a mixture of 2 ml of chloroform and 10 ml of ethanol. The resulting solution was cooled to −20° C. with stirring, into which was introduced hydrogen chloride up to saturation. The reaction mixture was stirred at 5° C. for 17 hours, and then evaporated. The resulting residue was dissolved in 10 ml of ethanol, to which was added 247 mg of ammonium acetate, and stirred at room temperature for 24 hours. The reaction mixture was evaporated, and the resulting residue was purified through ODS (YMC-GEL ODS-A 120-230/70, hereinafter the same) column chromatography using an eluent solvent of methanol/water (2/98). A small amount of 1 N hydrochloric acid was added to the purified product, which was further evaporated to obtain 64 mg of N-[(7-amidino-2-naphthyl)methyl]-N-[4-[4-(4-pyridyl) hexahydro-1H-1,4-diazepin-1-yl]phenyl] methanesulfonamide dihydro-chloride.

In the same manner as in Example 1, obtained were compounds of Examples 2 and 3 shown in Table 2.

EXAMPLE 4

340 mg of ethyl [N-[(7-amidino-2-naphthyl)methyl]-N-[4-[4-(4-pyridyl)hexahydro-1H-1,4-diazepin-1-yl]-phenyl] sulfamoyl acetate dihydrochloride obtained in Example 2 was dissolved in a mixture of 10 ml of 1,4-dioxane and 10 ml, of water, to which was added 3 ml of aqueous 1 N sodium hydroxide, and stirred at room temperature for 3 hours. 3 ml of 1 N hydrochloric acid was added to the reaction mixture, and then evaporated. The resulting residue was purified through ODS column chromatography using an eluent solvent of acetonitrile/water (10/90), and a small amount of 1 N hydrochloric acid was added to the purified product, which was then freeze-dried to obtain 154 mg of [N-[(7-amidino-2-naphthyl )methyl]1-N-[4-[4-( 4-pyridyl )hexahydro-1H-1,4-diazepin-1-yl]phenyl]sulfamoyl]acetic acid di-hydrochloride.

In the same manner as in Example 4, obtained were a compound of Example 5 shown in Table 2, a compound of Example 85 shown in Table 4 and compounds of Examples 90 to 93 shown in Table 7, respectively.

EXAMPLE 6

5.19 g of ethyl [N-[4-(4-t-butoxycarbonylhexa-hydro-1H-1,4-diazepin-1-yl)phenyl]-N-[(7-cyano-2-naphthyl)methyl] sulfamoyl]acetate obtained in Reference Example 26 was dissolved in a mixture of 9 ml of chloroform and 9 ml of ethanol. The resulting solution was cooled at −20° C. with stirring, into which was introduced hydrogen chloride up to saturation. The reaction mixture was stirred at 5° C. for 23 hours, and then evaporated. The resulting residue was dissolved in 18 ml of ethanol, to which was added 6.6 g of ammonium acetate, and stirred at room temperature for 28 hours. The resulting reaction mixture was evaporated, and the residue thus obtained was purified through ODS column chromatography using an eluent solvent of ethanol/water (10/90). A small amount of 1 N hydrochloric acid was added to this, which was then freeze-dried to obtain 1.02 g of ethyl [N-[(7-amidino-2-naphthyl)methyl]-N-[4-(hexahydro-1H-1,4-diazepin-1-yl)phenyl]sulfamoyl]acetate dihydrochloride.

In the same manner as in Example 6, obtained were compounds of Examples 7 to 15 shown in Table 2, compounds of Examples 45 to 63 shown in Table 3 and a compound of Example 86 shown in Table 5, respectively.

EXAMPLE 16

333 mg of N-[4-(4-t-butoxycarbonylhexahydro-1H-1,4-diazepin-1-yl)phenyl]-N-[(7-cyano-2-naphthyl)-methyl] methanesulfonamide obtained in Reference Example 24 was dissolved in 10 ml of ethanol, and the resulting solution was cooled to −20° C. with stirring, into which was introduced hydrogen chloride up to saturation. The reaction mixture was stirred at 5° C. for 15 hours, and then evaporated. The resulting residue was dissolved in a mixture of 10 ml of ethanol and 10 ml of methanol, to which was added 480 mg of ammonium acetate, and stirred at room temperature for 24 hours. The reaction mixture was evaporated, and the resulting residue was purified through ODS column chromatography. From the fraction having been eluted with an eluent solvent of methanol/water (5/95), obtained was 249 mg of a roughly-purified product of N-[(7-amidino-2-naphthyl)methyl]-N-[4-(hexahydro-1H-1,4-diazepin-1-yl)phenyl] sulfonamide. 224 mg of this product was dissolved in 10 ml of ethanol, to which were added 650 mg of ethyl acetimidate hydrochloride and 683 mg of triethylamine, and stirred at room temperature for 20 hours. The reaction mixture was evaporated, and the resulting residue was purified through ODS (YMC-GEL ODS-A 120-230/70) column chromatography using an eluent solvent of methanol/water (5/95). A small amount of 1 N hydrochloric acid was added to the thus-purified product, which was then freeze-dried to obtain 169 mg of N-[4-(4-acet-imidoylhexahydro-1H-1,4-diazepin-1-yl)phenyl]-N-[(7-amidino-2-naphthyl)methyl] methanesulfonamide dihydro-chloride.

In the same manner as in Example 16, obtained were compounds of Examples 17 to 21 shown in Table 2 and compounds of Examples 64 and 65 shown in Table 3, respectively.

EXAMPLE 22

590 mg of ethyl [N-[(7-amidino-2-naphthyl)methyl]-N-[4-(hexahydro-1H-1,4-diazepin-1-yl)phenyl]sulfamoyl]-acetate dihydrochloride obtained in Example 6 was dissolved in 22 ml of ethanol, to which were added 680 mg of ethyl acetimidate hydrochloride and 555 mg of triethylamine, and stirred at room temperature for 15 hours. The reaction mixture was evaporated, and the resulting residue was purified through ODS column chromatography using an eluent solvent of ethanol/water (10/90). A small amount of 1 N hydrochloric acid was added to this, which was then freeze-dried to obtain 118 mg of ethyl [N-[4-(4-acetimidoylhexahydro-1H-1,4-diazepin-1-yl)phenyl]-N-[(7-amidino-2-naphthyl)methyl]-sulfamoyl]acetate dihydrochloride.

In the same manner as in Example 22, obtained were compounds of Examples 23 to 29 shown in Table 2, compounds 66 to 70 shown in Table 3, compounds of compounds of Examples 71 to 73 shown in Table 4, a compound of Example 87 shown in Table 5 and a compound of Example 89 shown in Table 6, respectively.

EXAMPLE 30

1.37 g of methyl N-[4-(4-t-butoxycarbonylhexa-hydro-1H-1,4-diazepin-1-yl)phenyl]-N-[(7-cyano-2-naphthyl) methyl]malonamate obtained in Reference Example 29 was dissolved in a mixture of 15 ml of chloroform and 15 ml of methanol, and the resulting solution was cooled to −20° C. with stirring, into which was introduced hydrogen chloride up to saturation. The reaction mixture was stirred at 5° C. for 21 hours, and then evaporated. The resulting residue was dissolved in 30 ml of methanol, to which was added 2.3 g of ammonium acetate, and stirred at room temperature for 3 days. The reaction mixture was evaporated, and the resulting residue was purified through ODS column chromatography using an eluent solvent of methanol/water (5/95) to obtain a roughly-purified product of methyl N-[(7-amidino-2-naphthyl)methyl]-N-[4-(hexahydro-1H-1,4-diazepin-1-yl)-phenyl]malonamate.

This product was dissolved in 30 ml of methanol, to which were added 5.56 g of ethyl acetimidate hydrochloride and 4.45 g of triethylamine, and stirred at room temperature for 2 days. The reaction mixture was evaporated, and the resulting residue was purified through ODS column chromatography using an eluent solvent of methanol/water (5/95). A small amount of 1 N hydrochloric acid was added to the thus-purified product, which was then freeze-dried to obtain 950 mg of methyl N-[4-(4-acetimidoylhexahydro-1H-1,4-diazepin-1-yl)-phenyl]-N-[(7-amidino-2-naphthyl) methyl]malonamate dihydrochloride.

EXAMPLE 31

980 mg of ethyl [N-[(7-amidino-2-naphthyl)methyl]-N-[4-(hexahydro-1H-1,4-diazepin-1-yl)-3-fluorophenyl]-sulfamoyl]acetate dihydrochloride obtained in Example 11 was dissolved in 36 ml of ethanol, to which were added 1.12 g of ethyl acetimidate hydrochloride and 920 mg of triethylamine, and stirred at room temperature for 5 days. The reaction mixture was evaporated, and the resulting residue was purified through ODS column chromatography using an eluent solvent of ethanol/water (10/90) to obtain a roughly-purified product of ethyl [N-[4-(4-acetimidoylhexahydro-1H-1,4-diazepin-1-yl)-3-fluorophenyl]-N-[(7-amidino-2-naphthyl)methyl]sulfamo-yl]acetate. 1.02 g of this product was dissolved in 21 ml of concentrated hydrochloric acid, and stirred at room temperature for 16 hours. The reaction mixture was evaporated, and the resulting residue was dissolved in 20 ml of concentrated hydrochloric acid, and stirred at room temperature for 4 hours. The reaction mixture was evaporated, and the resulting residue was purified through ODS column chromatography using an eluent solvent of acetonitrile/water (5/95), and a small amount of 1 N hydrochloric acid was added to the thus-purified product, which was then freeze-dried to obtain 940 mg of [N-[4-(4-acetimidoylhexahydro-1H-1,4-diazepin-1-yl)- 3-fluorophenyl]-N-[(7-amidino-2-naphthyl) methyl]sulfamo-yl]acetic acid dihydrochloride.

In the same manner as in Example 31, obtained was a compound of Example 32 shown in Table 2.

EXAMPLE 33

450 mg of ethyl [N-[4-(4-acetimidoylhexahydro-1 H-1,4-diazepin-1-yl)phenyl]-N-[(7-amidino-2-naphthyl)-methyl] sulfamoyl]acetate dihydrochloride obtained in Example 22 was dissolved in 8 ml of concentrated hydrochloric acid, and stirred at room temperature for 14 hours. The reaction mixture was evaporated, and the resulting residue was dissolved in 8 ml of concentrated hydrochloric acid, and stirred at room temperature for 4 hours. The reaction mixture was evaporated, and the resulting residue was purified through ODS column chromatography using an eluent solvent of acetonitrile/water (10/90). A small amount of 1 N hydrochloric acid was added to this, which was then freeze-dried to obtain 302 mg of [N-[4-(4-acet-imidoylhexahydro- 1H-1,4-diazepin-1-yl)phenyl]-N-[(7-amidino-2-naphthyl) methyl]sulfamoyl]acetic acid dihydro-chloride.

In the same manner as in Example 33, compounds of Examples 34 and 35 shown in Table 2, compounds of Examples 36 to 42 shown in Table 3 and compounds of Examples 74 to 84 shown in Table 4, respectively.

EXAMPLE 43

300 mg of [N-[4-(4-acetimidoylhexahydro-1H-1,4-diazepin-1-yl)-3-fluorophenyl]-N-[(7-amidino-2-naphth-yl) methyl]sulfamoyl]acetic acid dihydrochloride obtained in Example 31 was dissolved in 10 ml of ethanol, to which was added 1 ml of a 4 N hydrochloric acid gas-dioxane solution, and stirred at room temperature for 22 hours. The reaction mixture was evaporated, and the resulting residue was dissolved in 20 ml of ethanol, to which was added 2 ml of a 4 N hydrochloric acid gas-dioxane solution, and stirred at room temperature for 7 hours. The reaction mixture was evaporated, and the resulting residue was purified through ODS column chromatography using an eluent solvent of ethanol. As mall amount of 1 N hydrochloric acid was added to the thus-purified product, which was then freeze-dried to obtain 238 mg of ethyl [N-[4-(4-acetimidoylhexahydro-1H-1,4-diazepin-1-yl)-3-fluorophenyl]-N-[(7-amidino-2-naphthyl)methyl]sulfamoyl]acetate dihydrochloride.

In the same manner as in Example 43, obtained was a compound of Example 44 shown Table 3.

EXAMPLE 88

538 mg of the compound obtained in Reference Example 40 was dissolved in a mixture of 10 ml of pyridine and 2 ml of triethylamine, into which was introduced a hydrogen sulfide gas at 0° C. with stirring up to saturation. The reaction mixture was stirred at room temperature for 14 hours, and then evaporated. The resulting residue was purified through silica gel column chromatography using an eluent solvent of ethyl acetate/chloroform (1/2) to obtain 436 mg of N-[4-(4-t-butoxycarbonylhexahydro-1H-1,4-diazepin-1-yl)phenyl]-N-[(5-thiocarbamoyl-2-benzofuranyl)methyl]methanesulfon-amide. 436 mg of this compound was dissolved in 9 ml of acetone, to which was added 0.6 ml of methyl iodide. The mixture was stirred for 1.5 hours under heating for reflux. The solvent was evaporated, and the residue was dissolved in 8 ml of methanol, to which was added 267 mg of ammonium acetate. The mixture was stirred for one hour under heating for reflux. The solvent was evaporated, and the resulting residue was purified through silica gel column chromatography using an eluent solvent of methanol/chloroform (1/9). 412 mg of a roughly-purified product of N-[4-(4-t-butoxycarbonyl-hexahydro-1H-1,4-diazepin-1-yl)phenyl]-N-[(5-amidino-2-benzofuranyl)methyl] methanesulfonamide was dissolved in 16 ml of 1,4-dioxane, to which was added 8 ml of a 4 N hydrogen chloride-1,4-dioxane solution. The reaction mixture was stirred at room temperature for 40 minutes, and the solvent was evaporated. The resulting residue was purified through ODS column chromatography using an eluent solvent of methanol/water (5/95), and a small amount of 1 N hydrochloric acid was added to the thus-purified product, which was then freeze-dried to obtain 108 mg of N-[(5-amidino-2-benzofuranyl) methyl]-N-[4-(1H-1,4-diazepin-1-yl)phenyl] methanesulfonamide trihydro-chloride.

EXAMPLE 94

230 mg of N-(4-(4-methylhexahydro-1H-1,4-diazepin-1-yl)phenyl]-N-[(7-cyano-2-naphthyl)methyl]sulfamide was dissolved in 9.2 ml of ethanol, to which were added 0.25 ml of triethylamine and 90 mg of hydroxylamine hydrochlo-ride. The mixture was heated for reflux for 2 hours. The reaction mixture was evaporated, and the resulting residue was purified through silica gel column chromatography using an eluent solvent of concentrated ammonia water/methanol/chloroform (0.1/1/7). The solvent was evaporated, and a small amount of aqueous 1 N hydrochloric acid was to the residue, and then evaporated again in vacuo, to obtain 41 mg of N-[(7-hydroxyamidino-2-naphthyl)methyl]-N-[4-(4-methylhexa-hydro-1H-1,4-diazepin-1-yl)phenyl] sulfamide trichloride.

In the same manner as in Example 94, obtained were compounds of Examples 95 to 101 shown Table 7.

EXAMPLE 102

210 mg of {N-[(7-amidino-2-naphthyl)methyl]-N-[4-(4-methylhexahydro-1H-1,4-diazepin-1-yl)phenyl]}sulf-amide was dissolved in 4 ml of dimethyl sulfoxide, to which were added 0.23 ml of triethylamine and 0.042 ml of methyl chloroformate. The mixture was stirred at room temperature for 50 minutes. To the reaction mixture was added aqueous saturated sodium hydrogencarbonate. The mixture was extracted with chloroform, dried over anhydrous sodium sulfate, and then evaporated. The resulting residue was purified through silica gel column chromatography using an eluent solvent of concentrated ammonia water/methanol/chloroform (0.1/1/10). The solvent was evaporated, and a small amount of aqueous dilute hydrochloric acid was added to the residue, which was then freeze-dried to obtain 121 mg of N-{[7-(N-methoxycarbonylamidino)-2-naphthyl] methyl}-N-[4-(4-methylhexahydro-1H-1,4-diazepin-1-yl) phenyl]sulfamide trihydrochloride.

In the same manner as in Example 102, obtained were compounds of Examples 103 to 107 shown Table 7.

The structural formulae and the physico-chemical data of the compounds of the Reference Examples are shown in Tables 8 to 14; the structural formulae of the compounds of the Examples are shown in Tables 2 to 7; and the physico-chemical data of the compounds of the Examples are shown in Tables 15 to 24. Further, the compounds having the structural formulae shown in Tables 25 to 27 can be produced in substantially the same manners described in the foregoing Examples or Production Examples, or can be easily produced by applying thereto small modifications which are obvious to those skilled in the art.

The meanings of the symbols in those Tables are mentioned below.

Rf: Reference Example No.

Ex: Example No.

NMR: Nuclear magnetic resonance spectrum

MS: Mass analytical data

Me: Methyl

Et: Ethyl

Py: Pyridyl

Bn: Benzyl nBu: n-Butyl iPr: Isopropyl

Boc: Butoxycarbonyl group

Tet: Tetrazolyl group

"2-" and "3-" that precede the substituents in those Tables mean, irrespective of the chemical names of the substituents, that the indicated substituents are bonded to the "2" and "3" positions, respectively, of the structural formulae in the Tables.

TABLE 2

| Ex | R¹ | X | Y | R² | Z | R | Sal |
|---|---|---|---|---|---|---|---|
| 1 | 4-py | —SO₂— | —CH₂— | H | CH | H | 2HCl |
| 2 | 4-py | —SO₂— | —CH₂— | —COOEt | CH | H | 2HCl |
| 3 | 4-py | —CO— | —CH₂CH₂— | —COOMe | CH | H | 2HCl |
| 4 | 4-py | —SO₂— | —CH₂— | —COOH | N | H | 2HCl |
| 5 | 4-py | —CO— | —CH₂— | —COOH | CH | H | 2HCl |
| 6 | H | —SO₂— | —CH₂— | —COOEt | CH | H | 2HCl |
| 7 | H | —SO₂NH— | —CH₂— | —COOEt | CH | H | 2HCl |
| 8 | H | —CO— | —CH₂— | —COOEt | CH | H | 2HCl |
| 9 | H | —CO— | —CH₂CH₂— | —COOEt | CH | H | 2HCl |
| 10 | H | —SO₂— | —CH₂— | —COOEt | CH | 3-Me | 2HCl |
| 11 | H | —SO₂— | —CH₂— | —COOEt | CH | 3-F | 2HCl |
| 12 | H | —SO₂— | —CH₂— | —COOEt | CH | 3-Cl | 2HCl |
| 13 | H | —SO₂— | —CH₂— | —COOEt | CH | 2-Me | 2HCl |
| 14 | H | —SO₂— | —CH₂— | —COOMe | CH | 2-COOMe | 2HCl |
| 15 | H | —SO₂— | —CH₂— | —COOEt | N | H | 2HCl |
| 16 | —C(=NH)—Me | —SO₂— | —CH₂— | H | CH | H | 2HCl |
| 17 | —C(=NH)—Me | —CO— | —CH₂— | H | CH | H | 2HCl |
| 18 | —C(=NH)—Me | —SO₂NH— | — | H | CH | H | 2HCl |
| 19 | —C(=NH)—Me | —SO₂NH— | — | —COOEt | CH | H | 2HCl |
| 20 | —C(=NH)—Me | —CONH— | —CH₂— | —COOEt | CH | H | 2HCl |
| 21 | —C(=NH)—Me | —CONH— | — | —COOEt | CH | H | 2HCl |
| 22 | —C(=NH)—Me | —SO₂— | —CH₂— | —COOEt | CH | H | 2HCl |
| 23 | —C(=NH)—Me | —SO₂NH— | —CH₂— | —COOEt | CH | H | 2HCl |
| 24 | —C(=NH)—Me | —CO— | —CH₂— | —COOEt | CH | H | 2HCl |
| 25 | —C(=NH)—Me | —CO— | —CH₂CH₂— | —COOEt | CH | H | 2HCl |
| 26 | —C(=NH)—Me | —SO₂— | —CH₂— | —COOH | CH | 3-Me | 2HCl |
| 27 | —C(=NH)—Me | —SO₂— | —CH₂— | —COOEt | CH | 3-Cl | 2HCl |
| 28 | —C(=NH)—Me | —SO₂— | —CH₂— | —COOEt | CH | 2-Me | 2HCl |
| 29 | —C(=NH)—Me | —SO₂— | —CH₂— | —COOMe | CH | 2-COOMe | 2HCl |
| 30 | —C(=NH)—Me | —CO— | —CH₂— | —COOMe | CH | H | 2HCl |
| 31 | —C(=NH)—Me | —SO₂— | —CH₂— | —COOEt | CH | 3-F | 2HCl |
| 32 | —C(=NH)—Me | —SO₂— | —CH₂— | —COOH | N | H | 2HCl |
| 33 | —C(=NH)—Me | —SO₂— | —CH₂— | —COOH | CH | H | 2HCl |
| 34 | —C(=NH)—Me | —SO₂NH— | —CH₂— | —COOH | CH | H | 2HCl |
| 35 | —C(=NH)—Me | —CO— | —CH₂— | —COOH | CH | H | 2HCl |

TABLE 3

| Ex | R¹ | X | Y | R² | Z | R | Sal |
|---|---|---|---|---|---|---|---|
| 36 | —C(=NH)—Me | —CO— | —CH₂CH₂— | —COOH | CH | H | 2HCl |
| 37 | —C(=NH)—Me | —CONH— | —CH₂— | —COOH | CH | H | 2HCl |
| 38 | —C(=NH)—Me | —SO₂— | —CH₂— | —COOEt | CH | 3-Me | 2HCl |
| 39 | —C(=NH)—Me | —SO₂— | —CH₂— | —COOH | CH | 2-Me | 2HCl |
| 40 | H | —SO₂— | —CH₂— | —COOH | CH | H | 2HCl |
| 41 | H | —CO— | —CH₂— | —COOH | CH | H | 2HCl |
| 42 | H | —CO— | —CH₂CH₂— | —COOH | CH | H | 2HCl |
| 43 | —C(=NH)—Me | —SO₂— | —CH₂— | —COOH | CH | 3-F | 2HCl |
| 44 | —C(=NH)—Me | —SO₂— | —CH₂— | —COOEt | N | H | 2HCl |
| 45 | H | —CO— | —CH₂— | —CONH₂ | CH | H | 2HCl |
| 46 | H | —CO— | —CH₂— | —CONHMe | CH | H | 2HCl |
| 47 | H | —CO— | —CH₂— | —CON(Me)₂ | CH | H | 2HCl |

TABLE 3-continued

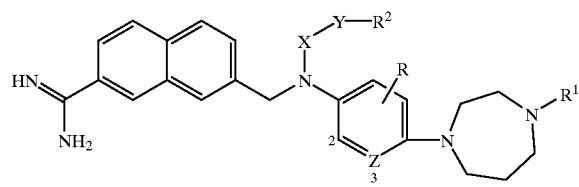

| Ex | R¹ | X | Y | R² | Z | R | Sal |
|---|---|---|---|---|---|---|---|
| 48 | H | —CO— | — | —OEt | CH | H | 2HCl |
| 49 | H | —CSNH— | —CH$_2$— | —COOEt | CH | H | 2HCl |
| 50 | H | —CO— | —CH$_2$— | -Tet | CH | H | 2HCl |
| 51 | —Me | —SO$_2$— | —CH$_2$— | —COOEt | CH | H | 2HCl |
| 52 | —Me | —SO$_2$— | —CH$_2$— | H | CH | H | 2HCl |
| 53 | —Me | —SO$_2$NH— | — | —COOEt | CH | H | 2HCl |
| 54 | —Me | —SO$_2$NH— | — | H | CH | H | 2HCl |
| 55 | —Me | —SO$_2$NH— | —CH$_2$— | H | CH | H | 2HCl |
| 56 | —Me | —SO$_2$N(Me)— | —CH$_2$— | H | CH | H | 2HCl |
| 57 | -nBu | —SO$_2$— | —CH$_2$— | —COOEt | CH | H | 2HCl |
| 58 | —Bn | —SO$_2$— | —CH$_2$— | —COOEt | CH | H | 2HCl |
| 59 | —C(=NH)—NH$_2$ | —SO$_2$— | —CH$_2$— | —COOEt | CH | H | 2HCl |
| 60 | —CH$_2$COOEt | —SO$_2$— | —CH$_2$— | H | CH | H | 2HCt |
| 61 | —CH$_2$CONH$_2$ | —SO$_2$— | —CH$_2$— | H | CH | H | 2HCl |
| 62 | H | —CO— | —CH$_2$— | —COOEt | N | H | 2HCl |
| 63 | H | —CO— | —CH$_2$CH$_2$— | —COOEt | N | H | 2HCl |
| 64 | —C(=NH)—Me | —CO— | —CH$_2$— | —COOnBu | CH | H | 2HCl |
| 65 | —C(=NH)—Me | —CO— | —CH$_2$— | —COOiPr | CH | H | 2HCl |
| 66 | —C(=NH)—Me | —CO— | —CH$_2$— | —CONH$_2$ | CH | H | 2HCl |
| 67 | —C(=NH)—Me | —CO— | —CH$_2$— | —CONHMe | CH | H | 2HCl |
| 68 | —C(=NH)—Me | —CO— | —CH$_2$— | —CON(Me)2 | CH | H | 2HCl |
| 69 | —C(=NH)—Me | —CO— | — | —OEt | CH | H | 2HCl |
| 70 | —C(=NH)—Me | —CSNH— | —CH$_2$— | —COOEt | CH | H | 2HCl |

TABLE 4

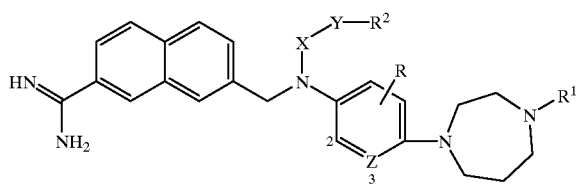

| Ex | R¹ | X | Y | R² | Z | R | Sal |
|---|---|---|---|---|---|---|---|
| 71 | —C(=NH)—Me | —CO— | —CH$_2$— | -Tet | CH | H | 2HCl |
| 72 | —C(=NH)—Me | —CO— | —CH$_2$— | —COOEt | N | H | 2HCl |
| 73 | —C(=NH)—Me | —CO— | —CH$_2$CH$_2$— | —COOEt | N | H | 2HCl |
| 74 | H | —CSNH— | —CH$_2$— | —COOH | CH | H | 2HCl |
| 75 | —C(=NH)—Me | —CSNH— | —CH$_2$— | —COOH | CH | H | 2HCl |
| 76 | —Me | —SO$_2$— | —CH$_2$— | —COOH | CH | H | 2HCl |
| 77 | -nBu | —SO$_2$— | —CH$_2$— | —COOH | CH | H | 2HCl |
| 78 | —Bn | —SO$_2$— | —CH$_2$— | —COOH | CH | H | 2HCl |
| 79 | —C(=NH)—NH$_2$ | —SO$_2$— | —CH$_2$— | —COOH | CH | H | 2HCl |
| 80 | H | —SO$_2$— | —CH$_2$— | —COOH | N | H | 2HCl |
| 81 | H | —CO— | —CH$_2$— | —COOH | N | H | 2HCl |
| 82 | —C(=NH)—Me | —CO— | —CH$_2$— | —COOH | N | H | 2HCl |
| 83 | H | —CO— | —CH$_2$CH$_2$— | —COOH | N | H | 2HCl |
| 84 | —C(=NH)—Me | —CO— | —CH$_2$CH$_2$— | —COOH | N | H | 2HCl |
| 85 | —CH$_2$COOH | —SO$_2$— | —CH$_2$— | —COOH | CH | H | 2HCl |

TABLE 5

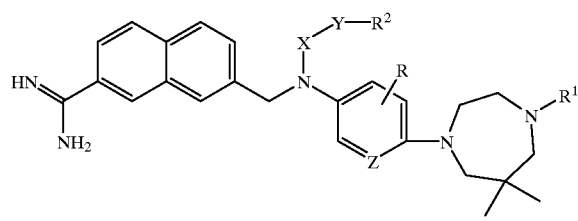

| Ex. | R¹ | X | Y | R² | Z | R | Sal |
|---|---|---|---|---|---|---|---|
| 86 | H | —SO₂— | —CH₂— | H | CH | H | 3HCl |
| 87 | —C(=NH)—Me | —SO₂— | —CH₂— | H | CH | H | 3HCl |

TABLE 6

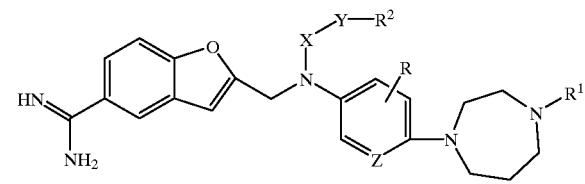

| Ex. | R¹ | X | Y | R² | Z | R | Sal |
|---|---|---|---|---|---|---|---|
| 88 | H | —SO₂— | —CH₂— | H | CH | H | 3HCl |
| 89 | —C(=NH)—Me | —SO₂— | —CH₂— | H | CH | H | 3HCl |

TABLE 7

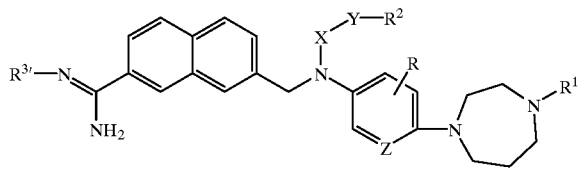

| Ex | R³ | R¹ | X | Y | R² | Z | R | Sal |
|---|---|---|---|---|---|---|---|---|
| 90 | —OH | 4-Py | —SO₂— | —CH₂— | —COOH | CH | H | 3HCl |
| 91 | —OH | —Me | —SO₂— | —CH₂— | —COOH | CH | H | 3HCl |
| 92 | —COOMe | —Me | —SO₂— | —CH₂— | —COOH | CH | H | 3HCl |
| 93 | —OH | H | —SO₂— | —CH₂— | —COOH | CH | H | 3HCl |
| 94 | —OH | —Me | —SO₂NH— | — | H | CH | H | 3HCl |
| 95 | —OH | 4-Py | —SO₂— | —CH₂— | —COOEt | CH | H | 3HCl |
| 96 | —OH | —Me | —SO₂— | —CH₂— | —COOEt | CH | H | 3HCl |
| 97 | —OH | H | —SO₂— | —CH₂— | —COOEt | CH | H | 3HCl |
| 98 | —OH | —Me | —SO₂NH— | —CH₂— | H | CH | H | 3HCl |
| 99 | —OH | —Me | —SO₂N(Me)— | —CH₂— | H | CH | H | 3HCl |
| 100 | —OH | —Me | —SO₂— | —CH₂— | H | CH | H | 3HCl |
| 101 | —OH | —Me | —SO₂NH— | — | —COOEt | CH | H | 3HCl |
| 102 | —COOMe | —Me | —SO₂NH— | — | H | CH | H | 3HCl |
| 103 | —COOMe | —Me | —SO₂— | —CH₂— | —COOEt | CH | H | 3HCl |
| 104 | —COOMe | —Me | —SO₂NH— | —CH₂— | H | CH | H | 3HCl |
| 105 | —COOMe | —Me | —SO₂N(Me)— | —CH₂— | H | CH | H | 3HCl |
| 106 | —COOMe | —Me | —SO₂— | —CH₂— | H | CH | H | 3HCl |
| 107 | —COOMe | —Me | —SO₂NH— | — | —COOEt | CH | H | 3HCl |

TABLE 8

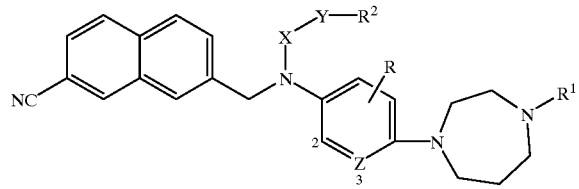

| Rf | R¹ | X | Y | R² | Z | R | Rf | R¹ | X | Y | R² | Z | R |
|---|---|---|---|---|---|---|---|---|---|---|---|---|---|
| 4 | 3-py | —SO₂— | —CH₂— | H | CH | H | 24 | -Boc | —SO₂— | — | Me | CH | H |
| 5 | 3-py | —SO₂— | —CH₂— | —COOEt | CH | H | 25 | -Boc | —CO— | — | Me | CH | H |
| 6 | 3-py | —CO— | —CH₂— | —COOMe | CH | H | 27 | -Boc | —SO₂NH— | — | -Boc | CH | H |
| 26 | -Boc | —SO₂— | —CH₂— | —COOEt | CH | H | 28 | -Boc | —SO₂NH— | — | —COOEt | CH | H |
| 29 | -Boc | —CO— | —CH₂— | —COOMe | CH | H | 30 | -Boc | —CONH— | —(CH₂)₂— | —COOEt | CH | H |
| 32 | -Boc | —SO₂— | —CH₂— | —COOEt | CH | 3-Me | 31 | -Boc | —CONH— | —CH₂— | —COOEt | CH | H |

TABLE 8-continued

| Rf | R¹ | X | Y | R² | Z | R | Rf. | R¹ | X | Y | R² | Z | R |
|---|---|---|---|---|---|---|---|---|---|---|---|---|---|
| 33 | -Boc | —SO₂— | —CH₂— | —COOEt | CH | 3-Cl | 36 | -Boc | —CONH— | — | —COOEt | CH | H |
| 34 | -Boc | —SO₂— | —CH₂— | —COOEt | CH | 2-Me | 38 | -Boc | —SO₂— | —CH₂— | —COOEt | N | H |
| 35 | -Boc | —SO₂— | —CH₂— | —COOEt | CH | 2-COOMe | 39 | -Boc | —SO₂N(Boc)- | —CH₂— | —COOEt | H | H |
| 37 | -Boc | —SO₂— | —CH₂— | —COOEt | CH | 3-F | | | | | | | |

TABLE 9

| Rf. | R¹ | Z | R³ | DATA |
|---|---|---|---|---|
| 1 | H | CH | H | NMR(DMSO-d₆)δ: 2.07–2.18(2H, m), 3.18–3.29(4H, m), 3.67(2H, t, J=5.9Hz), 3.90(2H, t, J=5.9Hz), 6.92(2H, d, J=9.5Hz), 8.09(2H, d, J=9.5Hz), 9.32(3H, br) |
| 2 | 3-Py | CH | H | NMR(CDCl₃)δ: 2.02–2.21(2H, m), 3.42–3.70(8H, m), 6.55(2H, d, J=3.2 Hz), 6.69(2H, d, J=9.5Hz), 8.14(2H, d, J=9.5Hz), 8.26(2H, d, J=3.2Hz) |
| 7 | H | CH | 3-Me | NMR(CDCl₃)δ: 1.89–1.97(2H, m), 2.38(3H, s), 2.82–3.08(4H, m), 3.35–3.73(4H, m), 6.99(1H, d, J=8.9Hz), 7.97–8.00(1H, m), 8.61(1H, br) |
| 8 | H | CH | 3-Cl | NMR(CDCl₃)δ: 1.93–2.03(2H, m), 3.03(2H, t, J=5.8Hz), 3.03(2H, t, J=5.8Hz), 3.53–3.61(4H, m), 7.01(1H, d, J=9.1Hz), 8.01(1H, dd, J=9.1Hz), 8.20(1H, dd, J=2.9Hz) |
| 9 | H | CH | 2-Me | NMR(CDCl₃)δ: 1.86–1.94(2H, m), 2.64(3H, s), 2.83(2H, t, J=5.6Hz), 3.04(2H, t, J=5.6Hz), 3.61(2H, t, J=5.6Hz), 3.66(2H, t, J=5.6Hz), 6.44(1H, d, J=2.8Hz), 6.52(1H, dd, J=2.8Hz, 9.4Hz), 8.09(1H, d, J=9.4Hz) |
| 10 | H | CH | 2-CN | NMR(CDCl₃)δ: 1.84–2.05(2H, m), 2.87(2H, t, J=5.4Hz), 3.07(2H, t, J=5.4Hz), 3.58–3.77(4H, m), 6.81(1H, dd, J=2.9Hz, 9.5Hz), 6.97(1H, d, J=2.9Hz), 8.18(1H, d, J=9.5Hz) |
| 11 | H | CH | 2-COOMe | NMR(CDCl₃)δ: 1.79–1.83(2H, m), 2.74(2H, t, J=5.5Hz), 2.95(2H, t, J=5.5Hz), 3.50–3.59(4H, m), 3.84(3H, m), 6.56(1H, s), 7.17(1H, d, J=8.2Hz), 7.91(1H, d, J=8.2Hz) |
| 12 | Boc | CH | H | NMR(CDCl₃)δ: 1.40(9H, s), 1.85–2.10(2H, m), 3.19-3.35(2H, m), 3.58–3.72(6H, m), 6.71(2H, d, J=9.5Hz), 8.12(2H, d, J=9.5Hz) |
| 13 | Boc | CH | 3-F | NMR(CDCl₃)δ: 1.36(4H, s), 1.43(5H, s), 1.91–2.02(2H, m), 3.35–3.48(2H, m), 3.59–3.72(6H, m), 6.75–6.81(1H, m), 7.86–7.95(2H, m) |
| 14 | Boc | N | H | NMR(CDCl₃)δ: 1.42(9H, s), 1.80–2.09(2H, m), 3.07–3.55(8H, m), 4.47(2H, s), 6.61(4H, s), 7.50–7.71(2H, m), 7.82–7.94(3H, m), 8.17(1H, s) |
| 15 | Boc | CH | 3-Me | NMR(CDCl₃)δ: 1.52(9H, s), 1.92–2.05(2H, m), 2.37(3H, s), 3.17–3.31(4H, m), 3.57–3.67(4H, m), 7.02(1H, d, J=8.8Hz), 7.96–8.04(2H, m) |
| 16 | Boc | CH | 3-Cl | NMR(CDCl₃)δ: 1.53(9H, s), 2.01–2.12(2H, m), 3.39–3.49(2H, m), 3.51–3.70(4H, m), 7.05(1H, d, J=9.0Hz), 8.03(1H, dd, 2.5Hz, 9.0Hz), 8.24(1H, d, J=2.5Hz) |
| 17 | Boc | CH | 2-Me | NMR(CDCl₃)δ: 1.53(9H, s), 1.94–2.02(2H, m), 2.64(3H, s), 3.23–3.38(2H, m), 3.59–3.66(6H, m), 6.45(1H, d, J=2.5Hz), 6.54(1H, dd, J=2.5Hz, 9.1Hz), 8.10(1H, d, J=9.1Hz) |
| 18 | Boc | CH | 2-COOMe | NMR(CDCl₃)δ: 1.42(9H, s), 1.91–2.00(2H, m), 3.24–3.40(2H, m), 3.58–3.70(6H, m), 3.93(3H, s), 6.64–6.74(2H, m), 8.03(1H, d, J=9.1Hz) |
| 21-1 | Bn | CH | 3-Cl | NMR(CDCl₃)δ: 1.98–2.06(2H, m), 2.76(2H, d, J=5.5Hz), 2.84(2H, t, J=5.1Hz), 3.55–3.66(4H, m), 3.67(2H, s), 6.94(1H, d, J=9.2Hz), 7.23–7.38(5H, m), 8.01(1H, dd, J=3.0Hz, 9.2Hz), 8.21(1H, d, J=2.9Hz) |

TABLE 10

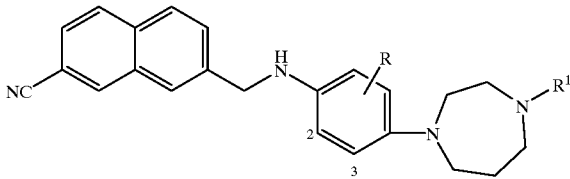

| Rf. | R₁ | R₃ | DATA |
|---|---|---|---|
| 3 | 3-Py | H | NMR(CDCl₃)δ: 2.05–2.16(2H, m), 3.35–3.48(4H, m), 3.51–3.58(2H, m), 3.63–3.68(2H, m), 4.48(2H, s), 6.52–6.58(2H, m), 6.79(1H, d, J=8.9Hz), 7.35(1H, d, J=8.9Hz), 7.56–7.60(1H, m), 7.63–7.69(2H, m), 7.86–7.90(2H, m), 8.20–8.27 (2H, m), 8.70(1H, s) |
| 19 | Boc | H | NMR(CDCl₃)δ: 1.40(4H, s), 1.42(5H, s), 1.94–2.00(2H, m), 3.27–3.40(2H, m), 3.57–3.62(2H, m), 3.71–3.93(4H, m), 6.50(1H, d, J=9.5Hz), 8.20 (1H, dd, J=2.6Hz, 9.5Hz), 9.04(1H, d, J=2.6Hz) |
| 20 | Boc | 3-Me | NMR(CDCl₃)δ: 1.45(4H, s), 1.48(5H, s), 1.82–1.95(2H, m), 2.23(3H, s), 2.91–3.02(4H, m), 3.44–3.59(4H, m), 4.69(2H, s), 6.41–6.46(1H, m), 6.51(1H, s), 6.87(1H, d, J=8.5Hz), 7.77(1H, dd, J=1.8Hz, 8.4Hz), 7.62–7.66(1H, m), 7.83–7.88(3H, m), 8.16(1H, s) |
| 21-2 | Bn | 3-Cl | NMR(CDCl₃)δ: 1.88–1.95(2H, m), 2.70–2.82(4H, m), 3.13–3.21(4H, m), 3.69 (2H, s), 4.48(2H, d, J=5.5Hz), 6.48(1H, dd, J=2.9Hz, 8.8Hz), 6.68(1H, d, J=3.0Hz), 6.97(1H, d, J=8.8Hz), 7.31–7.37(5H, m), 7.58(1H, dd, J=1.8Hz, 8.4Hz), 7.62(1H, dd, J=1.8Hz, 8.8Hz), 7.84–7.91(3H, m), 8.18(1H, s) |
| 21-3 | Boc | 3-Cl | NMR(CDCl₃)δ: 1.47(9H, s), 1.91–2.00(2H, m), 3.09–3.11(4H, m), 3.56–3.61 (4H, m), 4.49(2H, d, J=4.8Hz), 6.47(1H, dd, J=2.5Hz, 8.2Hz), 6.68(1H, d, J= 2.5Hz), 6.92(1H, d, J=8.2Hz), 7.57–7.64(2H, m), 7.84–7.92(3H, m), 8.19(1H, s) |
| 22 | Boc | 2-Me | NMR(CDCl₃)δ: 1.31(4H, s), 1.44(5H, s), 1.90–2.01(2H, m), 2.21(3H, s), 3.18–3.34(2H, m), 3.40–3.58(6H, m), 4.50(2H, s), 6.44–6.58(3H, m), 7.58(1H, dd, J=1.9Hz, 8.4Hz), 7.68(1H, dd, J=1.9Hz, 8.4Hz), 7.84–7.92(3H, m), 8.19(1H, s) |
| 23 | Boc | 2-COOMe | NMR(CDCl₃)δ: 1.35(4H, s), 1.49(5H, s), 1.87–2.01(2H, m), 3.20–3.34(2H, m), 3.40–3.49(4H, m), 3.51–3.58(2H, m), 3.89(3H, s), 4.61(2H, d, J=5.5Hz), 6.55 (1H, d, J=9.1Hz), 6.82(1H, dd, J=2.5Hz, 9.1Hz), 7.32(1H, d, J=2.5Hz), 7.57 (1H, dd, J=1.6Hz, 8.5Hz), 7.65(1H, dd, J=1.6Hz, 8.5Hz), 7.76–7.86(3H, m), 8.17(1H, s) |

TABLE 11

| Rf. | DATA |
|---|---|
| 4 | NMR(CDCl₃) δ: 1.92–2.25(2H, m), 2.98(3H, s), 3.30–3.58(8H, m), 4.95(2H, s), 6.40–6.68(4H, m), 7.08 (2H, d, J = 9.0Hz), 7.56–7.88(4H, m), 8.07–8.30(4H, m) |
| 5 | NMR(CDCl₃) δ: 1.39(3H, t, J = 7.2Hz), 2.01–2.07(2H, m), 3.38–3.43(4H, m), 3.57–3.64(4H, m), 4.06 (2H, s), 4.35(2H, q, J = 7.2Hz), 5.02(2H, s), 6.50–6.52((2H, m), 6.58(2H, d, J = 8.8Hz), 7.21 (2H, d, J = 8.8Hz), 7.57(1H, dd, J = 1.6Hz, 8.4Hz), 7.83(1H, d, J = 8.4Hz), 7.87(1H, d, J = 8.4Hz), 8.12(1H, s), 8.20–8.22(2H, m) |
| 6 | NMR(CDCl₃) δ: 2.02(2H, m), 3.29(2H, s), 3.40–3.47(4H, m), 3.61–3.66(4H, m), 3.70(3H, s), 5.03 (2H, s), 6.52(2H, d, J = 6.4Hz), 6.57(2H, d, J = 8.8Hz), 6.83(2H, d, J = 8.8Hz), 7.59 (1H, dd, J = 1.6Hz, 8.4Hz), 7.64(1H, dd, J = 1.6Hz, 8.4Hz), 7.70(1H, s), 7.84(1H, d, J = 8.4Hz), 7.89 (1H, d, J = 8.4Hz), m), 8.15(1H, s), 8.22(2H, d, J = 6.4Hz) |
| 24 | NMR(CDCl₃) δ: 1.30(4H, s), 1.38(5H, s), 1.84–1.94(2H, m), 2.97(3H, s), 3.15–3.33(2H, m), 3.44–3.56 (6H, m), 4.94(2H, s), 6.55(2H, d, J = 9.2Hz), 7.02–7.10(2H, m), 7.58(1H, dd, J = 1.9Hz, 8.4Hz), 7.65–7.73(2H, m), 7.84(1H, d, J = 9.9Hz), 7.84(1H, d, J = 9.9Hz), 8.13(1H, s) |

TABLE 12

| Rf. | DATA |
|---|---|
| 25 | NMR(CDCl₃) δ: 1.35(4H, s), 1.40(5H, s), 1.85–1.96(5H, m), 3.19–3.37(2H, m), 3.47–3.58(6H, m), 5.00 (2H, s), 6.57(2H, d, J = 9.2Hz), 6.75–6.82(2H, m), 7.55–7.67(3H, m), 7.82(1H, d, J = 8.6Hz), 7.88(1H, d, J = 8.6Hz), 8.15(1H, s) |
| 26 | NMR(CDCl₃) δ: 1.26(3H, t, J = 7.3Hz), 1.31(4H, s), 1.39(5H, s), 1.75–2.01(2H, m), 3.13–3.31(2H, m), 3.45–3.57(6H, m), 4.04(2H, s), 4.35(2H, q, J = 7.3Hz), 5.02(2H, s), 6.55(2H, d, J = 9.0Hz), 7.20 (2H, d, J = 9.0Hz), 7.50–7.92(5H, m), 8.13(1H, s) |
| 27 | NMR(CDCl₃) δ: 1.29(9H, s), 1.43(9H, s), 1.79–1.88(2H, m), 3.16–3.32(2H, m), 3.46–3.53(6H, m), 5.19(2H, s), 6.54(2H, d, J = 9.0Hz), 7.04–7.11(2H, m), 7.57(1H, dd, J = 1.9Hz, 9.0Hz), 7.65–7.70(2H, m), 7.81–7.89(2H, m), 8.13(1H, s) |

TABLE 12-continued

| Rf. | DATA |
|---|---|
| 28 | NMR(CDCl$_3$) : 1.30(4H, s), 1.37(3H, t, J = 7.0Hz), 1.39(5H, s), 1.84–1.91(2H, m), 3.15–3.21(1.4H, m), 3.25–3.30(0.6H, m), 3.44–3.51(6H, m), 4.33(2H, q, J = 7.0Hz), 5.19(2H, s), 6.54(2H, d, J = 9.2Hz), 7.04–7.07(2H, m), 7.57(1H, dd, J = 1.4Hz, 8.4Hz), 7.65–7.70(2H, m), 7.84(1H, d, J = 8.4Hz), 7.87(1H, d, J = 8.8Hz), 8.13(1H, s), 8.56–8.61(1H, m) |
| 29 | NMR(CDCl$_3$) δ: 1.35(4H, s), 1.40(5H, s), 1.86–1.92(2H, m), 3.18–3.35(4H, m), 3.47–3.55(6H, m), 3.70 (3H, s), 5.03(2H, s), 6.55(2H, d, J = 8.8Hz), 6.79–6.85(2H, m), 7.58(1H, dd, J = 1.4Hz, 8.4Hz), 7.64 (1H, dd, J = 1.4Hz, 8.4Hz), 7.70(1H, s), 7.84(1H, d, J = 8.4Hz), 7.86(1H, d, J = 8.4Hz), 8.15(1H, s) |
| 30 | NMR(CDCl$_3$) δ: 1.26(3H, t, J = 7.4Hz), 1.35(4H, s), 1.41(5H, s), 1.86–1.95(2H, m), 2.40(2H, t, J = 6.6Hz), 2.64(2H, t, J = 6.6Hz), 3.20–3.26(1H, m), 3.29–3.35(1H, m), 3.47–3.56(6H, m), 4.15(2H, q, J = 7.4 Hz), 5.00(2H, s), 6.57(2H, d, J = 8.8Hz), 6.63–6.68(2H, m), 7.58(1H, dd, J = 1.5Hz, 8.5Hz), 7.59(1H, dd, J = 1.5Hz, 8.5Hz), 7.69(1H, s), 7.82(1H, d, J = 8.5Hz), 7.88(1H, d, J = 8.5Hz), 8.15(1H, s) |
| 31 | NMR(CDCl$_3$) δ: 1.27(3H, t, J = 7.2Hz), 1.34(4H, s), 1.40(5H, s), 1.84–1.97(2H, m), 3.17–3.35(2H, m), 3.45–3.57(6H, m), 3.98(2H, d, J = 6.0Hz), 4.18(2H, q, J = 7.2Hz), 4.85(1H, t, J = 6.0Hz), 4.98(2H, s), 6.59(2H, d, J = 9.0Hz), 6.90–7.00(2H, m), 7.56(1H, dd, J = 1.5Hz, 8.4Hz), 7.65(1H, d, J = 9Hz), 7.69(1H, s), 7.82(1H, d, J = 8.4Hz), 7.87(1H, d, J = 8.4Hz), 8.15(1H, s) |
| 32 | NMR(CDCl$_3$) δ: 1.38(3H, t, J = 7.3Hz), 1.45(5H, s), 1.47(4H, s), 1.84–1.96(2H, m), 2.21(3H, s), 2.94–3.06(4H, m), 3.47–3.60(4H, m), 3.93(2H, s), 4.34(2H, q, J = 7.3Hz), 5.04(2H, s), 6.92(2H, d, J = 8.5Hz), 7.13–7.18(3H, m), 7.56–7.61(1H, m), 7.82–7.88(2H, m), 8.12(1H, s) |
| 33 | NMR(CDCl$_3$) δ: 1.38(3H, t, J = 7.2Hz), 1.45(9H, br), 1.92–2.02(2H, m), 3.08–3.14(4H, m), 3.49–3.61 (4H, m), 4.04(2H, s), 4.35(2H, q, J = 7.2Hz), 5.03(2H, s), 6.94(1H, d, J = 8.5Hz), 7.17(1H, dd, J = 2.2Hz, 8.5Hz), 7.43–7.47(2H, m), 7.57(1H, dd, J = 1.5Hz, 8.5Hz), 7.64–7.68(1H, m), 7.827.90(2H, m), 8.14(1H, s) |
| 34 | NMR(CDCl$_3$) δ: 1.39–1.42(12H, m), 1.78(3H, s), 1.86–1.95(2H, m), 3.18–3.27(2H, m), 3.45–3.56 (6H, m), 4.00(1H, d, J = 14Hz), 4.18(1H, d, J = 14Hz), 4.34(2H, q, J = 7.0Hz), 4.62(1H, d, J = 14Hz), 5.19(1H, d, J = 14Hz), 6.34(1H, d, J = 2.7Hz), 6.54(1H, d, J = 2.7Hz, 8.8Hz), 7.55–7.61(2H, m), 7.67 (1H, dd, J = 1.5Hz, 8.4Hz), 7.69(1H, d, J = 1.5Hz), 7.82(1H, d, J = 8.4Hz), 7.88(1H, d, J = 8.4Hz), 8.10(1H, s) |
| 35 | NMR(CDCl$_3$) δ: 1.29–1.36(7H, m), 1.41(5H, s), 1.86–1.94(2H, m), 3.17–3.32(2H, m), 3.46–3.54 (6H, m), 3.83(3H, s), 4.08(2H, d, J = 15.8Hz), 4.26(2H, q, J = 7.0Hz), 4.82(1H, br), 5.24(1H, br), 6.59 (1H, dd, J = 3.3Hz, 8.8Hz), 6.96–7.02(2H, m), 7.10(1H, d, J = 3.3Hz), 7.58(1H, dd, J = 1.4Hz, 8.4Hz), 7.68–7.73(1H, m), 7.82(1H, d, J = 8.5Hz), 7.88(1H, d, J = 8.5Hz), 8.12(1H, s) |
| 36 | NMR(CDCl$_3$) δ: 1.26(3H, t, J = 7.2Hz), 1.36(4H, s), 1.41(5H, s), 1.85–1.97(2H, m), 3.22–3.38(2H, m), 3.47–3.60(6H, m), 4.19(2H, q, J = 7.2Hz), 4.96(2H, s), 6.61(2H, d, J = 9.0Hz), 6.77(1H, s), 6.83(2H, d, J = 8.4Hz), 7.58(1H, dd, J = 1.8Hz, 8.4Hz), 7.63–7.70(2H, m), 7.83(1H, d, J = 9.0Hz), 7.89(1H, d, J = 8.4Hz), 8.14(1H, s) |
| 37 | NMR(CDCl$_3$) δ: 1.34(4H, s), 1.39(3H, t, J = 7.4Hz), 1.40(5H, s), 1.83–1.94(2H, m), 3.32–3.45(6H, m), 3.49–3.57(2H, m), 4.04(2H, s), 4.35(2H, q, J = 7.4Hz), 5.01(2H, s), 6.68–6.75(1H, m), 7.00–7.10 (2H, m), 7.58(1H, dd, J = 1.9Hz, 8.5Hz), 7.64–7.68(2H, m), 7.84(1H, d, J = 8.4Hz), 7.87(1H, d, J = 8.4 Hz), 8.14(1H, s) |

TABLE 13

| Rf. | DATA |
|---|---|
| 38 | NMR(CDCl$_3$) δ: 1.34–1.41(12H, m), 1.84–1.91(2H, m), 3.20–3.34(2H, m), 3.48–3.61(4H, m), 3.68–3.72(2H, m), 4.06(2H, s), 4.35(2H, q, J = 6.9Hz), 5.00(2H, s), 6.36(1H, d, J = 9.2Hz), 7.27–7.39 (1H, m), 7.58(1H, dd, J = 1.7Hz, 8.6Hz), 7.65–7.70(2H, m), 7.85(1H, d, J = 8.1Hz), 7.88(1H, d, J = 8.1 Hz), 8.13–8.15(2H, m) |
| 39 | NMR(CDCl$_3$) δ: 1.24(3H, t, J = 7.2Hz), 1.30(9H, s), 1.38(9H, s), 1.82–1.94(2H, m), 3.14–3.31(2H, m), 3.44–3.54(6H, m), 4.08(2H, s), 4.16(2H, q, J = 7.2Hz), 5.16(2H, s), 6.52(2H, d, J = 9.0Hz), 7.01–7.07 (2H, m), 7.56(1H, dd, J = 1.9Hz, 9.0Hz), 7.65–7.70(2H, m), 7.81–7.89(2H, m), 8.12(1H, s) |

TABLE 14

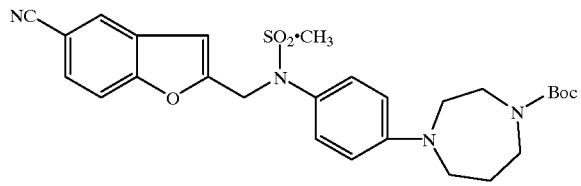

| Rf. | Data |
|---|---|
| 40 | NMR(CDCl$_3$)δ: 1.35(s, 4H), 1.41(s, 5H), 1.87–1.97(m, 2H), 2.98(s, 3H), 3.18–3.27(m, 1H), 3.27–3.36 (m, 1H), 3.48–3.60(m, 6H), 4.93(s, 2H), 6.60(d, 2H, J=9.0Hz), 6.65(s, 1H), 7.08(d, 2H, J=9.0Hz), 7.54–7.57(m, 2H), 7.85(s, 1H) |

TABLE 15

| Ex | DATA |
|---|---|
| 1 | NMR(DMSO-d$_6$) δ: 1.80–1.90(2H, m), 3.05(3H, s), 3.42–3.46(2H, m), 3.56–3.63(2H, m), 3.85–3.90 (4H, m), 4.97(2H, s), 6.66(2H, d, J = 9.2Hz), 7.02–7.11(2H, m), 7.15(2H, d, J = 9.2Hz), 7.62 (1H, dd, J = 1.9Hz, 8.8Hz), 7.79(1H, dd, J = 1.9Hz, 8.8Hz), 7.91(1H, s), 8.00(1H, d, J = 8.8Hz), 8.10(1H, d, J = 8.8Hz), 8.12–8.17(2H, m), 8.46(1H, s), 9.19(3H, br), 9.46(2H, br) |
| 2 | NMR(DMSO-d$_6$) δ: 1.27(3H, t, J = 6.8Hz), 1.82–1.89(2H, m), 3.42–3.46(2H, m), 3.60–3.63(4H, m), 3.83–3.86(2H, m), 4.24(2H, q, J = 6.8Hz), 4.33(2H, s), 4.98(2H, s), 6.82(2H, d, J = 9.2Hz), 7.03–7.10 (2H, m), 7.15(2H, d, J = 9.2Hz), 7.60(1H, dd, J = 1.6Hz, 8.8Hz), 7.82(1H, dd, J = 1.6Hz, 8.8Hz), 7.89 (1H, s), 8.01(1H, d, J = 8.8Hz), 8.11(1H, d, J = 8.8Hz), 8.12–8.16(2H, m), 8.48(1H, s), 9.31(2H, s), 9.52(2H, s), 13.68(1H, br) |
| 3 | NMR(DMSO-d$_6$) δ: 1.81–1.88(2H, m), 3.21(2H, s), 3.44–3.47(2H, m), 3.57(3H, s), 3.60–3.66(4H, m), 3.84–3.86(2H, m), 4.99(2H, s), 6/60(2H, d, J = 9.2Hz), 6.93(2H, d, J = 9.2Hz), 7.02–7.10(2H, m), 7.57(1H, dd, J = 1.6Hz, 8.4Hz), 7.82(1H, dd, J = 1.6Hz, 8.4Hz), 7.87(1H, s), 8.02(1H, d, J = 8.4Hz), 8.12(1H, d, J = 8.4Hz), 8.13–8.17(2H, m), 8.45(1H, s), 9.29(2H, s), 9.53(2H, s), 13.66(1H, br) |
| 4 | NMR(DMSO-d$_6$) δ: 1.83–1.89(2H, m), 3.42–3.45(2H, m), 3.59–3.63(4H, m), 3.83–3.86(2H, m), 4.22(2H, s), 4.98(2H, s), 6.69(2H, d, J = 8.8Hz), 7.03–7.09(2H, m), 7.15(2H, d, J = 8.8Hz), 7.61 (1H, dd, J = 1.6Hz, 8.4Hz), 7.83(1H, dd, J = 1.6Hz, 8.4Hz), 7.89(1H, s), 8.01(1H, d, J = 8.4Hz), 8.11 (1H, d, J = 8.4Hz), 8.12–8.15(2H, m), 8.50(1H, s), 9.37(2H, s), 9.55(2H, s), 13.76(1H, br) |
| 5 | NMR(DMSO-d$_6$) δ: 1.82–1.89(2H, m), 3.12(2H, s), 3.45–3.48(2H, m), 3.60–3.66(4H, m), 3.84–3.87 (2H, m), 4.99(2H, s), 6.70(2H, d, J = 8.8Hz), 6.95(2H, d, J = 8.8Hz), 7.02–7.09(2H, m), 7.58 (1H, dd, J = 1.6Hz, 8.4Hz), 7.84(1H, dd, J = 1.6Hz, 8.4Hz), 7.90(1H, s), 8.02(1H, d, J = 8.8Hz), 8.11–8.16(3H, m), 8.48(1H, s), 9.39(2H, s), 9.58(2H, s), 13.80(1H, br) |
| 6 | NMR(DMSO-d$_6$) δ: 1.27(3H, t, J = 7.0Hz), 2.01–2.07(2H, m), 3.03–3.06(2H, m), 3.11–3.15(2H, m), 3.41(2H, t, J = 6.0Hz), 3.62–3.65(2H, m), 4.24(2H, q, J = 7.0Hz), 4.36(2H, s), 5.01(2H, s), 6.68(2H, d, J = 9.2Hz), 7.20(2H, d, J = 9.2Hz), 7.66(1H, dd, J = 1.7Hz, 8.6Hz), 7.82(1H, dd, J = 1.7Hz, 8.6Hz), 7.90 (1H, s), 8.02(1H, d, J = 8.6Hz), 8.10(1H, d, J = 8.6Hz), 8.49(1H, s), 9.27(2H, br), 9.31(2H, s), 9.52 (2H, s) |

TABLE 16

| Ex | DATA |
|---|---|
| 7 | NMR(DMSO-d$_6$) δ: 1.24(3H, t, J = 7.0Hz), 2.01–2.08(2H, m), 2.99–3.06(2H, m), 3.08–3.15(2H, m), 3.34–3.42(2H, m), 3.59–3.65(2H, m), 3.81(2H, d, J = 5.2Hz), 4.18(2H, q, J = 7.0Hz), 4.91(2H, s), 6.63 (2H, d, J = 9.0Hz), 7.16(2H, d, J = 9.0Hz), 7.66(1H, dd, J = 1.5Hz, 8.4Hz), 7.81(1H, dd, J = 1.5Hz, 8.4Hz), 7.88(1H, s), 7.96–8.01(2H, m), 8.08(1H, d, J = 8.8Hz), 8.45(1H, s), 9.42(4H, s), 9.53(2H, br) |
| 8 | NMR(DMSO-d$_6$) δ: 1.16(3H, t, J = 7.0Hz), 2.02–2.09(2H, m), 3.01–3.06(2H, m), 3.10–3.15(2H, m), 3.28(2H, s), 3.43(2H, t, J = 7.0Hz), 3.63–3.67(2H, m), 4.04(2H, q, J = 7.0Hz), 5.03(2H, s), 6.69(2H, d, J = 9.1Hz), 7.00(2H, d, J = 9.1Hz), 7.63(1H, dd, J = 1.6Hz, 9.6Hz), 7.81(1H, dd, J = 1.6Hz, 8.6Hz), 7.87 (1H, s), 8.04(1H, d, J = 8.6Hz), 8.12(1H, d, J = 8.6Hz), 8.45(1H, s), 9.29(4H, s), 9.53(2H, s) |
| 9 | NMR(DMSO-d$_6$) δ: 1.18(3H, t, J = 7.0Hz), 1.89–1.96(2H, m), 2.35(2H, t, J = 7.0Hz), 2.53(2H, t, J = 7.0Hz), 2.89(2H, t, J = 5.6Hz), 3.02(2H, t, J = 5.2Hz), 3.44(2H, t, J = 6.2Hz), 3.56(2H, t, J = 5.2Hz), 4.06(2H, q, J = 7.0Hz), 4.99(2H, s), (2H, d, J = 9.2Hz), 6.99(2H, d, J = 9.2Hz), 7.61(1H, dd, J = 1.6Hz, 8.2Hz), 7.79(1H, dd, J = 1.6Hz, 8.2Hz), 7.84(1H, s), 8.01(1H, d, J = 8.6Hz), 8.11(1H, d, J = 8.6Hz), 8.44(1H, s), 9.52(6H, br) |
| 10 | NMR(DMSO-d$_6$) δ: 1.26(3H, t, J = 7.0Hz), 1.95–2.04(2H, m), 2.21(3H, s), 3.02(2H, t, J = 5.5Hz), 3.16–3.26(6H, m), 4.23(2H, q, J = 7.0Hz), 4.41(2H, s), 5.06(2H, s), 7.02(1H, d, J = 8.8Hz), 7.17 (1H, dd, J = 2.4Hz, 8.8Hz), 7.28(1H, d, J = 2.4Hz), 7.64–7.68(1H, m), 7.80–7.84(1H, m), 7.93(1H, s), 8.02(1H, d, J = 8.5Hz), 8.10(1H, d, J = 8.5Hz), 8.49(1H, s), 9.34(2H, br), 9.41(2H, br), 9.54(2H, br) |
| 11 | NMR(DMSO-d$_6$) δ: 1.26(3H, t, J = 7.0Hz), 2.03–2.10(2H, m), 3.13–3.22(4H, m), 3.27(2H, t, J = 6.8Hz), 3.42–3.46(2H, m), 4.23(2H, q, J = 7.0Hz), 4.45(2H, s), 5.06(2H, s), 6.84–6.89(1H, m), 7.11(1H, dd, J = 2.8Hz, 9.2Hz), 7.28(1H, dd, J = 2.8Hz, 14.4Hz), 7.66(1H, dd, J = 1.6Hz, 8.8Hz), 7.80(1H, dd, J = 1.6Hz, 8.8Hz), 7.94(1H, s), 8.02(1H, d, J = 8.8Hz), 8.10(1H, d, J = 8.8Hz), 8.48(1H, s), 9.15 (2H, br), 9.23(2H, s), 9.49(2H, s) |
| 12 | NMR(DMSO-d$_6$) δ: 1.24(3H, t, J = 7.3Hz), 2.00–2.03(2H, m), 3.14–3.28(6H, m), 3.31–3.36(2H, m), 4.23(2H, q, J = 7.3Hz), 4.50(2H, s), 5.04(2H, s), 7.14(1H, d, J = 8.8Hz), 7.32(1H, dd, J = 2.3Hz, 8.8Hz), 7.53(1H, d, J = 2.3Hz), 7.64–7.68(1H, m), 7.82(1H, dd, J = 1.9Hz, 8.5Hz), 7.94(1H, s), 8.03(1H, d, J = 8.5Hz), 8.10(1H, d, J = 8.5Hz), 8.49(1H, s), 9.32(4H, br), 9.51(2H, br) |
| 13 | NMR(DMSO-d$_6$) δ: 1.26(3H, t, J = 7.0Hz), 1.83(3H, s), 2.02–2.10(2H, m), 3.01–3.09(2H, m), 3.11–3.17 (2H, m), 3.40–3.46(2H, m), 3.63–3.71(2H, m), 4.24(2H, q, J = 7.0Hz), 4.32(1H, d, J = 14.3Hz), 4.52 (1H, d, J = 14.3Hz), 4.68(1H, d, J = 14.3Hz), 5.12(1H, d, J = 14.3Hz), 6.47(1H, d, J = 2.7Hz), 6.65(1H, dd, J = 2.7Hz, 8.8Hz), 7.38(1H, d, J = 8.8Hz), 7.64(1H, dd, J = 1.6Hz, 8.4Hz), 7.80(1H, s), 7.84(1H, dd, J = 1.6Hz, 8.4Hz), 8.02(1H, d, J = 8.4Hz), 8.11(1H, d, J = 8.4Hz), 8.47(1H, s), 9.40(4H, br), 9.55 (2H, br) |
| 14 | NMR(DMSO-d$_6$) δ: 2.01–2.09(2H, m), 3.03–3.10(2H, m), 3.11–3.19(2H, m), 3.41–3.48(2H, m), 3.65–3.70(2H, m), 3.71(3H, s), 3.72(3H, s), 4.39(2H, d, J = 4.8Hz), 4.97(2H, br), 6.85(1H, dd, J = 2.9Hz, 8.8 Hz), 6.97(1H, d, J = 2.9Hz), 7.19(1H, d, J = 8.8Hz), 7.71(1H, dd, J = 1.5Hz, 8.4Hz), 7.82(1H, dd, J = 1.5 Hz, 8.4Hz), 7.88(1H, s), 8.01(1H, d, J = 8.4Hz), 8.10(1H, d, J = 8.4Hz), 8.45(1H, s), 9.28(4H, br), 9.52 (2H, br) |
| 15 | NMR(DMSO-d$_6$) δ: 1.27(3H, t, J = 7.2Hz), 1.92–2.04(2H, m), 3.08–3.18(4H, m), 3.56–3.61(2H, m), 3.81–3.85(2H, m), 4.24(2H, q, J = 7.2Hz), 4.47(2H, s), 5.04(2H, s), 6.68(1H, d, J = 8.8Hz), 7.60 (1H, d, J = 8.8Hz), 7.67(1H, dd, J = 1.6Hz, 8.8Hz), 7.81(1H, dd, J = 1.6Hz, 8.4Hz), 7.95(1H, s), 8.02–8.06(2H, m), 8.11(1H, d, J = 8.8Hz), 8.48(1H, s), 8.98(2H, br), 9.15(2H, s), 9.46(2H, s) |
| 16 | NMR(DMSO-d$_6$) δ: 1.77–1.87(2H, m), 2.01(1.8H, s), 2.24(1.2H, s), 3.09(3H, s), 3.44–3.76(8H, m), 4.98(2H, s), 6.65–6.73(2H, m), 7.16–7.23(2H, m), 7.63–7.68(1H, m), 7.78–7.84(1H, m), 7.89–7.93 |

TABLE 16-continued

| Ex | DATA |
|---|---|
| | (1H, m), 7.99–8.04(1H, m), 8.09(1H, d, J = 8.8Hz), 8.49(0.4H, s), 8.51(0.6H, s), 8.61(0.6H, s), 8.75 (0.4H, s), 9.24–9.32(3H, m), 9.51(2H, s) |
| 17 | NMR(DMSO-d$_6$) δ: 1.78–1.87(5H, m), 2.01(2H, s), 2.25(1H, s), 3.48–3.88(8H, m), 4.99(2H, s), 6.68–6.75(2H, m), 6.95–7.03(2H, m), 7.55–7.61(1H, m), 7.79–7.87(2H, m), 7.99–8.04(1H, m), 8.11(1H, d, J = 8.9Hz), 8.49(0.3H, s), 8.53(0.7H, s), 8.64(0.7H, s), 8.78(0.3H, s), 9.27–9.35(3H, m), 9.50–9.56 (2H, s)<br>MS(m/z): 457(M − 2HCl + 1)$^+$ |

TABLE 17

| Ex | DATA |
|---|---|
| 18 | NMR(DMSO-d$_6$) δ: 1.82–1.88(2H, m), 2.03(2H, s), 2.26(1H, s), 3.45–3.71(8H, m), 4.86(2H, s), 6.72 (2H, br), 7.13–7.20(3H, m), 7.71(1H, d, J = 8.6Hz), 7.81–7.86(1H, m), 7.91(1H, d, J = 8.6Hz), 8.00 (1H, d, J = 8.6Hz), 8.02(1H, d, J = 8.6Hz), 8.06–8.11(1H, m), 8.74(1H, s), 9.49(4H, br), 9.63(2H, br) |
| 19 | NMR(DMSO-d$_6$) δ: 1.28(3H, t, J = 7.0Hz), 1.78–1.85(2H, m), 2.07(1.8H, s), 2.33(1.2H, s), 3.45–3.59 (5H, m), 3.63–3.74(3H, m), 4.15(2H, q, J = 7.0Hz), 5.12(1.2H, s), 5.13(0.8H, s), 6.69–6.74(2H, m), 7.06–7.10(2H, m), 7.62–7.65(1H, m), 7.81–7.84(1H, m), 7.91(1H, s), 8.02–8.05(1H, m), 8.11 (1H, d, J = 8.6HZ), 8.49(0.4H, s), 8.52(0.6H, s), 8.67(0.6H, s), 8.80(0.4H, s), 9.31(2H, s), 9.38(1H, s), 9.53(0.8H, s), 9.54(1.2H, s), 11.44(1H, s) |
| 20 | NMR(DMSO-d$_6$) δ: 1.21(3H, t, J = 7.0Hz), 1.79–1.90(2H, m), 2.09(2H, s), 2.26(1H, s), 3.40–3.80 (10H, m), 4.11(2H, q, J = 7.0Hz), 4.94(2H, s), 5.87(0.7H, t, J = 5.9Hz), 5.93(0.3H, t, J = 5.9Hz), 6.70–6.77(2H, m), 6.97–7.04(2H, m), 7.59–7.64(1H, m), 7.78–7.85(2H, m), 7.99–8.04(1H, m), 8.11 (1H, d, J = 8.6Hz), 8.44(0.7H, s), 8.48(0.3H, s), 8.62(0.7H, s), 8.75(0.3H, s), 9.22(2H, s), 9.33(1H, s), 9.46–9.53(2H, m) |
| 21 | NMR(DMSO-d$_6$) δ: 1.13(3H, t, J = 7.0Hz), 1.78–1.90(2H, m), 2.07(2H, s), 2.28(1H, s), 3.48–3.83 (8H, m), 4.01(2H, q, J = 7.5Hz), 4.95–5.01(2H, m), 6.77(1H, d, J = 8.6Hz), 6.96–7.06(2H, m), 7.56–7.62(1H, m), 7.82–7.91(2H, m), 7.99–8.05(1H, m), 8.11(1H, d, J = 8.6Hz), 8.49–8.64(2H, m), 8.79(0.7H, s), 8.95(0.3H, s), 9.44(2H, s), 9.54(1H, s), 9.59–9.66(2H, m) |
| 22 | NMR(DMSO-d$_6$) δ: 1.25–1.29(3H, m), 1.79–1.85(2H, m), 2.03(2H, s), 2.25(1H, s), 3.47–3.75(8H, m), 4.21–4.27(2H, m), 4.37(2H, s), 5.00(2H, s), 6.68–6.73(2H, m), 7.17–7.21(2H, m), 7.62–7.66(1H, m), 7.82(1H, d, J = 8.8Hz), 7.90(1H, s), 8.03(1H, dd, J = 4.0Hz, 8.8Hz), 8.10(1H, d, J = 8.8Hz), 8.49 (0.4H, s), 8.51(0.6H, s), 8.64(0.6H, s), 8.76(0.4H, s), 9.29(2H, s), 9.33(1H, s), 9.53(2H, s)<br>MS(m/z): 565(M − 2HCl + 1)$^+$ |
| 23 | NMR(DMSO-d$_6$) δ: 1.22(3H, t, J = 7.0Hz), 1.80–1.86(2H, m), 2.01(2H, s), 2.25(1H, s), 3.49–3.54 (6H, m), 3.66(2H, s), 3.71–3.82(2H, m), 4.13(2H, q, J = 7.0Hz), 4.90(2H, s), 6.66–6.75(2H, m), 7.16–7.20(2H, m), 7.62–7.67(1H, m), 7.82–7.89(2H, m), 8.08–8.11(2H, m), 8.51(1H, s), 8.74(1H, s), 9.43 (4H, br), 9.62(2H, br)<br>MS(m/z): 580(M − 2HCl + 1)$^+$ |
| 24 | NMR(DMSO-d$_6$) δ: 1.13–1.18(3H, m), 1.78–1.85(2H, m), 2.03(2H, s), 2.25(1H, s), 3.26(1.4H, s), 3.28 (0.6H, s), 3.48–3.54(4H, m), 3.58–3.72(4H, m), 4.00–4.07(2H, m), 5.02(2H, s), 6.69–6.73(2H, m), 6.69–7.01(2H, m), 7.60–7.63(1H, m), 7.80–7.83(1H, m), 7.86(0.7H, s), 7.88(0.3H, s), 8.04(1H, d, J = 8.4Hz), 8.12(1H, d, J = 8.4Hz), 8.45(0.3H, s), 8.48(0.7H, s), 8.60(0.7H, bs), 8.74(0.3H, bs), 9.24 (2H, br), 9.28(1H, br), 9.52(2H, s)<br>MS(m/z): 529(M − 2HCl + 1)$^+$ |
| 25 | NMR(DMSO-d$_6$) δ: 1.18(3H, t, J = 7.0Hz), 1.81–1.86(2H, m), 2.01(2H, s), 2.25(1H, s), 2.29–2.36 (2H, m), 2.52–2.57(2H, m), 3.50–3.56(3H, m), 3.58–3.62(1H, m), 3.65–3.76(4H, m), 4.06 (2H, q, J = 7.0Hz), 4.99(2H, s), 6.71–6.76(2H, m), 6.97–7.02(2H, m), 7.56–7.58(1H, m), 7.79–7.85 (2H, m), 8.02(1H, d, J = 8.6Hz), 8.11(1H, d, J = 8.6Hz), 8.46(0.3H, s), 8.49(0.7H, s), 8.62(0.7H, s), 8.76(0.3H, s), 9.27(2H, s), 9.37(1H, s), 9.52(2H, s) |
| 26 | NMR(DMSO-d$_6$) δ: 1.26(3H, t, J = 7.0Hz), 1.86–1.97(2H, m), 2.14–2.21(3H, brs), 2.27(2H, s), 2.34 (1H, s), 2.97–3.03(2H, br), 3.10–3.17(2H, m), 3.66–3.75(4H, m), 4.23(2H, q, J = 7.0Hz), 4.43 (2H, brs), 5.07(2H, s), 6.96–7.04(1H, m), 7.19(1H, dd, J = 2.1Hz, 8.0Hz), 7.27–7.30(1H, br), 7.66 (1H, dd, J = 1.4Hz, 8.4Hz), 7.85(1H, dd, J = 1.4Hz, 8.4Hz), 7.93(1H, s), 8.03(1H, d, J = 8.6Hz), 8.09(1H, d, J = 8.6Hz), 8.53(1H, s), 8.78(0.6H, s), 8.85(0.4H, s), 9.44(3H, s), 9.61(2H, s) |
| 27 | NMR(DMSO-d$_6$) δ: 1.24(3H, t, J = 7.0Hz), 1.90–2.00(2H, m), 2.25(2H, s), 2.32(1H, s), 3.09–3.18 (2H, m), 3.20–3.40(2H, m), 3.64–3.74(4H, m), 4.22(2H, q, J = 7.0Hz), 4.51(2H, s), 5.04(2H, s), 7.12 (0.4H, d, J = 8.8Hz), 7.14(0.6H, d, J = 8.8Hz), 7.33(1H, dd, J = 2.5Hz, 8.8Hz), 7.54(1H, d, J = 2.5Hz), 7.64–7.68(1H, m), 7.83(1H, dd, J = 1.8Hz, 8.4Hz), 7.94(1H, s), 8.03(1H, d, J = 8.5Hz), 8.10 (1H, d, J = 8.5Hz), 8.51(1H, s), 8.74(0.6H, s), 8.77(0.4H, s), 9.37(3H, br), 9.56(2H, br) |

TABLE 18

| Ex | DATA |
|---|---|
| 28 | NMR(DMSO-d$_6$) δ: 1.27(3H, t, J = 7.5Hz), 1.78(2H, s), 1.82(1H, s), 1.83(2H, br), 2.10(2H, s), 2.29 (1H, s), 3.50–3.61(5H, m), 3.70(2H, br), 3.79(1H, br), 4.25(2H, q, J = 7.5Hz), 4.34(1H, d, J = 14.0Hz), 4.54(1H, d, J = 14.0Hz), 5.13(2H, d, J = 14.0Hz), 6.54(1H, br), 6.69(1H, br), 7.37–7.40(1H, m), |

TABLE 18-continued

| Ex | DATA |
|---|---|
| | 7.58–7.63(1H, m), 7.78(1H, s), 7.86–7.92(1H, m), 8.02–8.06(1H, m), 8.09–8.14(1H, m), 8.47(1H, s), 8.57(0.6H, s), 8.79(0.4H, s), 9.48(2H, s), 9.56(1H, br), 9.67(2H, s) |
| 29 | NMR(DMSO-$d_6$) δ: 1.82(2H, br), 2.11(2H, s), 2.27(1H, s), 3.51–3.59(8H, m), 3.72(6H, s), 4.43(2H, br) 4.91(1H, d, J = 14.5Hz), 5.13(1H, d, J = 14.5Hz), 6.86–6.92(1H, m), 6.99(1H, br), 7.14 (1H, d, J = 9.1Hz), 7.18(1H, d, J = 9.1Hz), 7.66–7.74(1H, m), 7.87(1H, br), 8.00–8.04(1H, m), 8.08–8.14(1H, m), 8.54(1H, s), 8.84(0.6H, s), 8.98(0.4H, s), 9.47(2H, s), 9.55(1H, br), 9.75(2H, br) |
| 30 | NMR(DMSO-$d_6$) δ: 1.78–1.84(2H, m), 2.03(2H, s), 2.25(1H, s), 3.28(1.3H, s), 3.30(0.7H, s), 3.49–3.55(4H, m), 3.57(1H, s), 3.58(2H, s), 3.60–3.75(4H, m), 5.01(2H, s), 6.70–6.73(2H, m), 6.96–7.00(2H, m), 7.57–7.62(1H, m), 7.81–7.91(2H, m), 8.04(1H, d, J = 8.6Hz), 8.12(1H d, J = 8.6Hz), 8.47(0.3H, s), 8.51(0.7H, s), 8.65(0.7H, s), 8.80(0.3H, s), 9.30(3H, br), 9.55(2H, s) |
| 31 | NMR(DMSO-$d_6$) δ: 1.82–1.89(2H, m), 2.09(1.5H, s), 2.28(1.5H, s), 3.29–3.35(2H, m), 3.39–3.42 (1H, m), 3.47–3.50(1H, m), 3.60–3.70(3H, m), 3.72–3.78(1H, m), 4.33(2H, s), 5.05(2H, s), 6.86–6.92(1H, m), 7.08–7.12(1H, m), 7.25–7.29(1H, m), 7.66(1H, dd, J = 1.6Hz, 8.6Hz), 7.83(1H, d, J = 8.6 Hz), 7.93(1H, s), 8.03(1H, d, J = 8.6Hz), 8.10(1H, d, J = 8.6Hz), 8.51(1H, s), 8.73(1H, br), 9.33(3H, br), 9.53(2H, s) |
| 32 | NMR(DMSO-$d_6$) δ: 1.79–1.83(2H, m), 2.12(1.8H, s), 2.25(1.2H, s), 3.53–3.60(2H, m), 3.64–3.70 (3H, m), 3.73–3.82(2H, m), 3.84–3.88(1H, m), 4.39(2H, s), 5.04(2H, s), 6.79–6.86(1H, m), 7.64–7.69(2H, m), 7.84(1H, dd, J = 2.0Hz, 10.2Hz), 7.94(1H, s), 8.01–8.06(1H, m), 8.12(1H, d, J = 11.3Hz), 8.53(0.6H, s), 8.54(0.4H, s), 8.73(0.6H, s), 8.82(0.4H, s), 9.36(2H, s), 9.41(0.4H, s), 9.43(0.6H, s), 9.57(2H, s) MS(m/z): 538(M − 2HCl + 1)⁺ |
| 33 | NMR(DMSO-$d_6$) δ: 1.79–1.86(2H, m), 2.03(2H, s), 2.26(1H, s), 3.49–3.79(8H, m), 4.26(2H, s), 5.00 (1.4H, s), 5.01(0.6H, s), 6.70–6.74(2H, m), 7.18–7.22(2H, m), 7.63–7.67(2H, m), 7.84–7.90(1H, m), 8.02(0.3H, d, J = 8.4Hz), 8.03(0.7H, d, J = 8.4Hz), 8.10(1H, d, J = 8.4Hz), 8.54(0.3H, s), 8.57 (0.7H, s), 8.75(0.7H, s), 8.92(0.3H, s), 9.45(2H, s), 9.48(1H, s), 9.62(0.6H, s), 9.63(1.4H, s) MS(m/z): 537(M − 2HCl + 1)⁺ |
| 34 | NMR(DMSO-$d_6$) δ: 1.80–1.87(2H, m), 2.01(2H, s), 2.25(1H, s), 3.46–3.56(4H, m), 3.63–3.71(2H, m), 3.73(2H, s), 3.75–3.79(2H, m), 4.89(2H, s), 6.76–6.84(2H, m), 7.13–7.20(2H, m), 7.65(1H, dd, J = 3.8Hz, 8.1Hz), 7.82–7.94(3H, m), 8.01(1H, d, J = 8.1Hz), 8.08(1H, d, J = 8.6Hz), 8.65(1H, s), 9.42 (4H, br), 9.61(2H, br) |
| 35 | NMR(DMSO-$d_6$) δ: 1.78–1.86(2H, m), 2.03(2H, s), 2.25(1H, s), 3.17(1.4H, s), 3.19(0.6H, s), 3.49–3.55(4H, m), 3.59–3.74(4H, m), 5.02(2H, s), 6.70–6.74(2H, m), 6.97–7.02(2H, m), 7.60–7.62 (1H, m), 7.78–7.83(1H, m), 7.90(0.7H, s), 7.92(0.3H, s), 8.03(1H, d, J = 8.8Hz), 8.12(1H, d, J = 8.8Hz), 8.45(0.7H, s), 8.48(0.7H, s), 8.61(0.7H, s), 8.75(0.3H, s), 9.27(3H, br), 9.53(2H, s) |
| 36 | NMR(DMSO-$d_6$) δ: 1.80–1.82(2H, m), 2.04(2H, s), 2.25(1H, s), 2.26–2.33(2H, m), 2.46–2.52(2H, m), 3.48–3.75(8H, m), 4.99(2H, s), 6.71–6.74(2H, m), 6.99–7.06(2H, m), 7.56–7.59(1H, m), 7.95–7.82 (1H, m), 7.86(1H, br), 8.00(1H, d, J = 9.2Hz), 8.12(1H, d, J = 9.2Hz), 8.44(0.3H, s), 8.45(0.7H, s), 8.53(0.7H, br), 8.65(0.3H, br), 9.17(3H, br), 9.47(2H, s), MS(m/z): 515(M − 2HCl + 1)⁺ |
| 37 | NMR(DMSO-$d_6$) δ: 1.78–1.92(2H, m), 2.08(2H, s), 2.33(1H, s), 3.47–3.82(10H, m), 4.94(2H, s), 5.70–5.90(1H, m), 6.78(2H, d, J = 7.5Hz), 6.98–7.07(2H, m), 7.62(1H, d, J = 8.5Hz), 7.80–7.87 (2H, m), 7.98–8.04(1H, m), 8.10(1H, d, J = 8.9Hz), 8.47(0.3H, s), 8.52(0.7H, s), 8.73(0.7H, s), 8.90 (0.3H, s), 9.39(2H, s), 9.49(1H, s), 9.54–9.62(2H, m) |
| 38 | NMR(DMSO-$d_6$) δ: 1.86–1.96(2H, m), 2.18(3H, br), 2.26(2H, s), 2.33(1H, s), 2.98(2H, br), 3.12 (2H, br), 3.66–3.71(4H, m), 4.29(2H, br), 5.06(2H, s), 6.98–7.02(1H, m), 7.19(1H, d, J = 6.0Hz), 7.29 (1H, br), 7.66(1H, d, J = 8.8Hz), 7.82(1H, dd, J = 1.6Hz, 8.8Hz), 7.94(1H, s), 8.02(1H, d, J = 8.8Hz), 8.09(1H, d, J = 8.8Hz), 8.51(1H, s), 8.70(0.6H, s), 8.76(0.4H, s), 9.35(3H, s), 9.54(2H, s) |

TABLE 19

| Ex | DATA |
|---|---|
| 39 | NMR(DMSO-$d_6$) δ: 1.82(2H, br), 2.11(2H, s), 2.27(1H, s), 3.51–3.59(8H, m), 3.72(6H, s), 4.43 (2H, br), 4.91(1H, d, J = 14.5Hz), 5.13(1H, d, J = 14.5Hz), 6.86–6.92(1H, m), 6.99(1H, br), 7.14 (1H, d, J = 9.1Hz), 7.18(1H, d, J = 9.1Hz), 7.66–7.74(1H, m), 7.87(1H, br), 8.00–8.04(1H, m), 8.08–8.14(1H, m), 8.54(1H, s), 8.84(0.6H, s), 8.98(0.4H, s), 9.47(2H, s), 9.55(1H, br), 9.75(2H, br) |
| 40 | NMR(DMSO-$d_6$) δ: 1.99–2.06(2H, m), 3.03–3.08(2H, m), 3.12–3.16(2H, m), 3.41(2H, t, J = 6.0Hz), 3.61–3.65(2H, m), 4.23(2H, s), 5.01(2H, s), 6.68(2H, d, J = 9.1Hz), 7.21(2H, d, J = 9.1Hz), 7.66 (1H, dd, J = 1.6Hz, 8.6Hz), 7.79–7.82(1H, m), 7.91(1H, s), 8.02(1H, d, J = 8.6Hz), 8.10 (1H, d, J = 8.6Hz), 8.47(1H, s), 9.12(2H, br), 9.23(2H, br), 9.48(2H, s) |
| 41 | NMR(DMSO-$d_6$) δ: 2.01–2.07(2H, m), 3.03–3.08(2H, m), 3.12–3.16(2H, m), 3.20(2H, s), 3.43 (2H, t, J = 5.9Hz), 3.63–3.67(2H, m), 5.03(2H, s), 6.70(2H, d, J = 9.2Hz), 7.02(2H, d, J = 9.2Hz), 7.63 (1H, dd, J = 1.6Hz, 8.6Hz), 7.81(1H, dd, J = 1.6Hz, 8.6Hz), 7.91(1H, s), 8.02(1H, d, J = 8.6Hz), 8.12 (1H, d, J = 8.6Hz), 8.44(1H, s), 9.16(2H, br), 9.23(2H, br), 9.50(2H, s) |
| 42 | NMR(DMSO-$d_6$) δ: 2.00–2.06(2H, m), 2.32(2H, t, J = 6.4Hz), 2.51(2H, t, J = 6.4Hz), 3.06–3.11(2H, m), 3.15–3.19(2H, m), 3.40–3.46(2H, m), 3.61–3.66(2H, m), 5.00(2H, s), 6.71(2H, d, J = 8.8Hz), 7.03 (2H, d, J = 8.8Hz), 7.58(1H, dd, J = 1.6Hz, 8.6Hz), 7.78(1H, dd, J = 1.6Hz, 8.6Hz), 7.86(1H, s), 8.00 (1H, d, J = 8.6Hz), 8.11(1H, d, J = 8.6Hz), 8.43(1H, s), 8.93(2H, br), 9.12(2H, s), 9.45(2H, s) |
| 43 | NMR(DMSO-$d_6$) δ: 1.26(1H, t, J = 7.0Hz), 1.83–1.89(2H, m), 2.09(1.5H, s), 2.29(1.5H, s), 3.30–3.36 (2H, m), 3.40–3.43(1H, m), 3.47–3.51(1H, m), 3.61–3.70(3H, m), 3.76–3.80(1H, m), 4.23 (2H, q, J = 7.0Hz), 4.47(2H, s) , 5.06(2H, s), 6.87–6.93(1H, m), 7.07–7.11(1H, m), 7.25–7.29(1H, m), |

TABLE 19-continued

| Ex | DATA |
|---|---|
| | 7.65(1H, d, J = 8.6Hz), 7.84(1H, d, J = 8.6Hz), 7.93(1H, s), 8.07(1H, d, J = 8.0Hz), 8.10(1H, d, J = 8.0Hz), 8.52(0.5H, s), 8.54(0.5H, s), 8.80(0.5H, s), 8.82(0.5H, s), 9.41–9.46(3H, m), 9.59(2H, br) |
| 44 | NMR(DMSO-$d_6$) δ: 1.24–1.28(3H, m), 1.78–1.85(2H, m), 2.12(18H, s), 2.25(1.2H, s), 3.53–3.61 (2H, m), 3.64–3.70(3H, m), 3.74–3.81(2H, m), 3.84–3.88(1H, m), 4.22–4.27(2H, m), 4.52(2H, s), 5.04(2H, s), 6.78–6.86(1H, m), 7.64–7.68(2H, m), 7.84(1H, d, J = 8.6Hz), 7.93(1H, s), 8.02–8.06 (2H, m), 8.12(1H, d, J = 8.6Hz), 8.53(0.6H, s), 8.55(0.4H, s) 8.75(0.6H, br), 8.84(0.4H, br), 9.34–9.46(3H, m), 9.58(2H, br) |
| 45 | NMR(DMSO-$d_6$) δ: 2.01–2.07(2H, m), 3.02–3.07(4H, m), 3.11–3.16(2H, m), 3.41–3.45(2H, m), 3.64–3.67(2H, m), 5.03(2H, s), 6.69(2H, t, J = 9.3Hz), 6.95(2H, d, J = 9.3Hz), 7.39(1H, s), 7.64 (1H, dd, J = 1.2Hz, 8.8Hz), 7.80(1H, dd, J = 1.2Hz, 8.4Hz), 7.94(1H, s), 8.02(1H, d, J = 8.4Hz), 8.14 (1H, d, J = 8.8Hz), 8.43(1H, s), 9.17(2H, s), 9.23(2H, s), 9.51(2H, s) |
| 46 | NMR(DMS)-$d_6$) δ: 0.99(3H, t, J = 3.0Hz), 2.01–2.07(2H, m), 3.01–3.08(6H, m), 3.41–3.44(2H, m), 3.63–3.67(2H, m), 5.02(2H, s), 6.68(2H, d, J = 9.0Hz), 7.02(2H, d, J = 9.0Hz), 7.64(1H, dd, J = 1.6Hz, 8.0Hz), 7.80(1H, dd, J = 1.6Hz, 8.8Hz), 7.88–7.91(2H, m), 8.02(1H, d, J = 8.8Hz), 8.13 (1H, d, J = 8.0Hz), 8.43(1H, s), 9.14–9.24(4H, m), 9.50(2H, s) |
| 47 | NMR(DMSO-$d_6$) δ: 0.83(3H, t, J = 6.8Hz), 0.98(3H, t, J = 6.8Hz), 1.93–2.00(2H, m), 2.88–2.92(2H, m), 3.00–3.10(4H, m), 3.18–3.42(6H, m), 3.56–3.60(2H, m), 5.02(2H, s), 6.34(2H, d, J = 8.8Hz), 6.99(2H, d, J = 8.8Hz), 7.70(1H, dd, J = 1.4Hz, 8.3Hz), 7.80(1H, dd, J = 2.0Hz, 8.8Hz), 7.91(1H, s), 8.03(1H, d, J = 8.3Hz), 8.12(1H, d, J = 8.8Hz), 8.41(1H, s) |
| 48 | NMR(DMSO-$d_6$) δ: 1.15(3H, t, J = 6.8Hz), 2.01–2.11(2H, m), 3.02–3.20(4H, m), 3.39–3.45(2H, m), 3.62–3.67(2H, m), 4.11(2H, q, J = 6.8Hz), 4.99(2H, s), 6.66(2H, d, J = 8.7Hz), 7.02(2H, d, J = 8.7Hz), 7.60(1H, d, J = 8.8Hz), 7.82(1H, d, J = 8.8Hz), 7.86(1H, s), 8.03(1H, d, J = 8.3Hz), 8.11(1H, d, J = 8.3Hz), 8.50(1H, s), 9.22–9.37(4H, m), 9.49–9.56(2H, s) |
| 49 | NMR(DMSO-$d_6$) δ: 1.22(3H, t, J = 7.3Hz), 2.03–2.11(2H, m), 3.00–3.15(4H, m), 3.40–3.46(2H, m), 3.64–3.70(2H, m), 4.11(2H, q, J = 7.3Hz), 4.22(2H, d, J = 5.8Hz), 5.62(2H, s)6.75(2H, d, J = 9.3Hz), 6.98(2H, d, J = 9.3Hz), 7.14(1H, t, J = 5.8Hz), 7.71(1H, dd, J = 1.4Hz, 8.8Hz), 7.81(1H, dd, J = 1.4Hz, 8.8Hz), 7.89(1H, s), 8.01(1H, d, J = 8.8Hz), 8.11(1H, d, J = 8.8Hz), 8.45(1H, s), 9.22–9.35(4H, m), 9.51(2H, s) |

TABLE 20

| Ex | DATA |
|---|---|
| 50 | NMR(DMSO-$d_6$) δ: 2.02–2.10(2H, m), 3.03–3.09(2H, m), 3.11–3.18(2H, m), 3.42–3.48(2H, m), 3.64–3.71(2H, m), 3.91(2H, s), 5.06(2H, s), 6.73(2H, d, J = 8.8Hz), 7.11(2H, d, J = 8.8Hz), 7.63 (1H, dd, J = 1.4Hz, 8.3Hz), 7.81(1H, dd, J = 1.4Hz, 8.3Hz), 7.91(1H, s), 8.03(1H, d, J = 8.3Hz), 8.12 (1H, d, J = 8.3Hz), 8.49(1H, s), 9.29(4H, br), 9.53(2H, s) |
| 51 | NMR(DMSO-$d_6$) δ: 1.27(3H, t, J = 7.2Hz), 2.04–2.16(1H, m), 2.28–2.40(1H, m), 2.71(1.5H, s), 2.72 (1.5H, s), 2.99–3.09(2H, m), 3.26–3.42(4H, m), 3.62–3.76(2H, m), 4.25(2H, q, J = 7.2Hz), 4.36(2H, s), 5.02(2H, s), 6.67(2H, d, J = 8.4Hz), 7.22(2H, d, J = 8.4Hz), 7.67(1H, d, J = 8.4Hz), 7.83(1H, d, J = 8.4Hz), 7.90(1H, s), 8.03(1H, d, J = 8.4Hz), 8.10(1H, d, J = 8.4Hz), 8.51(1H, s), 9.37(2H, s), 9.56 (2H, s), 11.21(1H, s) |
| 52 | NMR(DMSO-$d_6$) δ: 2.08–2.12(1H, m), 2.29–2.41(1H, m), 2.70(1.5H, s), 2.72(1.5H, s), 2.96–3.08 (5H, m), 3.25–3.42(4H, m), 3.62–3.76(2H, m), 5.00(2H, s), 6.65(2H, d J = 8.8Hz), 7.23 (2H, d, J = 8.8Hz), 7.68(1H, dd, J = 1.6Hz, 8.4Hz), 7.84(1H, d, J = 8.0Hz), 7.90(1H, s), 8.01 (1H, d, J = 8.4Hz), 8.09(1H, d, J = 8.0Hz), 8.54(1H, s), 9.44(2H, s), 9.61(2H, s), 11.30(1H, s) |
| 53 | NMR(DMSO-$d_6$) δ: 1.29(3H, t, J = 7.2Hz), 2.04–2.14(1H, m), 2.29–2.40(1H, m), 2.71(1.5H, s), 2.73 (1.5H, s), 2.99–3.09(2H, m), 3.28–3.40(4H, m), 3.61–3.72(2H, m), 4.24(2H, q, J = 7.2Hz), 5.14(2H, s), 6.68(2H, d, J = 8.8Hz), 7.11(2H, d, J = 8.8Hz), 7.68(1H, dd, J = 1.6Hz, 8.8Hz), 7.83(1H, dd, J = 1.6Hz, 8.4Hz), 7.91(1H, s), 8.03(1H, d, J = 8.4Hz), 8.10(1H, d, J = 8.4Hz), 8.49(1H, s), 9.35(2H, s), 9.55 (2H, s), 11.22(1H, s), 11.41(1H, s) |
| 54 | NMR(DMSO-$d_6$) δ: 2.04–2.12(1H, m), 2.25–2.37(1H, m), 2.71(1.5H, s), 2.72(1.5H, s), 2.97–3.07 (2H, m), 3.25–3.42(4H, m), 3.60–3.72(2H, m), 4.87(2H, s), 5.30–5.85(2H, br), 6.62(2H, d, J = 8.8Hz), 7.17(2H, d, J = 8.8Hz), 7.73(1H, d, J = 1.6Hz, 8.8Hz), 7.81(1H, dd, J = 1.6Hz, 8.8Hz), 7.72(1H, s), 7.99(1H, d, J = 8.8Hz), 8.08(1H, d, J = 8.8Hz), 8.45(1H, s), 9.34(2H, s), 9.54(2H, s), 11.16(1H, s) |
| 55 | NMR(DMSO-$d_6$) δ: 2.03–2.15(1H, m), 2.28–2.38(1H, m), 2.67(3H, s), 2.71(3H, d, J = 4.9Hz), 2.97–3.11(2H, m), 3.22–3.46(4H, m), 3.60–3.75(2H, m), 4.93(2H, s), 6.62(2H, d, J = 9.2Hz), 7.17 (2H, d, J = 9.2Hz), 7.67(1H, br d), 7.82(1H, dd, J = 1.8Hz, 8.6Hz), 7.90(1H, br s), 8.00 (1H, d, J = 8.6Hz), 8.08(1H, d, J = 8.6Hz), 8.48(1H, s), 9.35(2H, s), 9.55(2H, s), 11.16(1H, br s) |
| 56 | NMR(DMSO-$d_6$) δ: 2.02–2.16(1H, m), 2.25–2.40(1H, m), 2.71(3H, d, J = 4.4Hz), 2.78(6H, s), 2.98–3.11(2H, m), 3.22–3.46(4H, m), 3.60–3.75(2H, m), 4.93(2H, s), 6.62(2H, d, J = 9.2Hz), 7.17 (2H, d, J = 8.8Hz), 7.66(1H, dd, J = 1.6Hz, 8.4Hz), 7.82(1H, dd, J = 1.6Hz, 8.4Hz), 7.88(1H, br s), 8.01(1H, d, J = 8.4Hz), 8.09(1H, d, J = 8.4Hz), 8.49(1H, s), 9.34(2H, s), 9.55(2H, s) |
| 57 | NMR(DMSO-$d_6$) δ: 0.85–0.89(3H, m), 1.23–1.30(5H, m), 1.59–1.72(2H, m), 2.06–2.13(1H, m), 2.31–2.41(1H, m), 2.95–3.05(4H, M), 3.25–3.45(4H, m), 3.68–3.73(2H, m), 4.25(2H, 1, J = 7.2Hz), 4.36 (2H, s), 5.02(2H, s), 6.66(2H, d, J = 8.8Hz), 7.22(2H, d, J = 8.8Hz), 7.66(1H, dd, J = 1.6Hz, 8.8Hz), 7.82(1H, dd, J = 1.6Hz, 8.8Hz), 7.91(1H, s), 8.02(1H, d, J = 8.8Hz), 8.10(1H, d, J = 8.8Hz), 8.48(1H, s), 9.28(2H, s), 9.51(2H, s), 10.88(1H, s) |
| 58 | NMR(DMSO-$d_6$) δ: 1.27(3H, t, J = 7.6Hz), 2.07–2.16(1H, m), 2.39–2.49(1H, m), 2.91–3.02(2H, m), 3.24–3.42(4H, m), 3.72–3.76(2H, m), 4.22–4.34(4H, m), 4.35(2H, s), 5.02(2H, s), 6.66(2H, d, J = 8.8Hz), 7.20(2H, d, J = 8.8Hz), 7.41–7.44(3H, m), 7.61–7.68(3H, m), 7.83(1H, dd, J = 1.2Hz, |

TABLE 20-continued

| Ex | DATA |
|---|---|
|  | 8.8Hz), 7.90(1H, s), 8.02(1H, d, J = 8.8Hz), 8.10(1H, d, J = 8.8Hz), 8.50(1H, s), 9.34(2H, s), 9.54 (2H, s), 11.41(1H, s) |
| 59 | NMR(DMSO-$d_6$) δ: 1.27(3H, t, J = 7.2Hz), 1.78–1.83(2H, m), 3.36–3.38(2H, m), 3.44–3.49(2H, m), 3.52–3.58(4H, m), 4.24(2H, q, J = 7.2Hz), 4.38(2H, s), 5.00(2H, s), 6.69(2H, d, J = 9.2Hz), 7.18 (2H, d, J = 9.2Hz), 7.37(4H, s), 7.64(1H, dd, J = 1.2Hz, 8.4Hz), 7.81(1H, dd, J = 1.4Hz, 8.8Hz), 7.91 (1H, s), 8.03(1H, d, J = 8.8Hz), 8.11(1H, d, J = 8.4Hz), 8.47(1H, s), 9.20(2H, s), 9.47(2H, s) |
| 60 | NMR(DMSO-$d_6$) δ: 1.15(3H, t, J = 7.1Hz), 1.73–1.83(2H, m), 2.53–2.68(2H, m), 2.68–2.86(2H, m), 3.08(3H, s), 3.29–3.41(6H, m), 4.03(2H, br s), 4.97(2H, s), 6.58(2H, d, J = 8.8Hz), 7.16 (2H, d, J = 8.8Hz), 7.66(1H, dd, J = 1.5Hz, 8.8Hz), 7.79(1H, dd, J = 1.5Hz, 8.8Hz), 7.92(1H, s), 8.01 (1H, d, J = 8.8Hz), 8.10(1H, d, J = 8.8Hz), 8.45(1H, s), 9.18(2H, s), 9.45(2H, s) |

TABLE 21

| Ex | DATA |
|---|---|
| 61 | NMR(DMSO-$d_6$) δ: 1.79–1.85(2H, m), 2.49–2.53(2H, m), 2.65–2.69(2H, m), 2.94(2H, s), 3.08(3H, s), 3.36–3.39(2H, m), 3.42–3.45(2H, m), 4.96(2H s), 6.58(2H, d, J = 9.0Hz), 7.03(1H, s), 7.13(1H, s), 7.15(2H, d, J = 9.0Hz), 7.64(1H, dd, J = 1.5Hz, 8.3Hz), 7.79(1H, dd, J = 1.5Hz, 8.8Hz), 7.88(1H, s), 7.99(1H, s), 8.05(1H, s), 8.39(1H, s), 9.90(2H, br) |
| 62 | NMR(DMSO-$d_6$) δ: 1.16(3H, t, J = 7.4Hz), 2.05–2.12(2H, m), 3.08–3.24(4H, m), 3.37(2H, s), 3.63–3.68 (2H, m), 3.92–3.96(2H, m), 4.05(2H, q, J = 7.4Hz), 5.06(2H, s), 6.91(1H, d, J = 9.2Hz), 7.57(1H, d, J = 9.2Hz), 7.63(1H, dd, J = 1.5Hz, 8.8Hz), 7.84(1H, dd, J = 1.2Hz, 8.8Hz), 7.89(1H, s), 7.91(1H, d, J = 2.5 Hz), 8.05(1H, d, J = 8.8Hz), 8.13(1H, d, J = 8.8Hz), 8.50(1H, s), 9.37(2H, s), 9.53(2H, s), 9.58(2H, s) |
| 63 | NMR(DMSO-$d_6$) δ: 1.19(3H, t, J = 1.2Hz), 2.04–2.11(2H, m), 2.39(2H, t, J = 6.4Hz), 2.58(2H, t, J = 6.4 Hz), 3.10–3.20(4H, m), 3.64–3.68(2H, m), 3.91–3.95(2H, m), 4.07(2H, q, J = 7.2Hz), 5.03(2H, s), (1H, d, J = 8.0Hz), 7.55–7.61(2H, m), 7.83(1H, d, J = 8.8Hz), 7.87(1H, s), 7.95(1H, d, J = 2.8Hz), 8.03 (1H, d, J = 8.8Hz), 8.12(1H, d, J = 8.8Hz), 8.49(1H, s), 9.35(2H, s), 9.45(2H, s), 9.56(2H, s) |
| 64 | NMR(DMSO-$d_6$) δ: 0.87(3H, t, J = 7.2Hz), 1.24–1.32(2H, m), 1.48–1.54(2H, m), 1.78–1.85(2H, m), 2.03(2H, s), 2.26(1H, s), 3.26(1.3H, s), 3.28(0.7H, s), 3.52–3.78(8H, m), 3.99(2H, t, J = 6.8Hz), 5.02 (2H, s), 6.70–6.73(2H, m), 6.95–7.00(2H m), 7.60–7.64(1H, m), 7.83–7.87(2H, m), 8.02–8.06 (1H, m), 8.13(1H, d, J = 8.8Hz), 8.49(0.3H, s), 8.55(0.7H, s), 8.73(0.7H, s), 8.89(0.3H, s) 9.41(2H, s), 9.45(1H, s), 9.60–9.62(2H, m) |
| 65 | NMR(DMSO-$d_6$) δ: 1.14–1.17(6H, m), 1.78–1.84(2H, m), 2.03(1.8H, s), 2.26(1.2H, s), 3.22(1.3H, s), 3.24(0.7H, s), 3.50–3.78(8H, m), 4.82–4.89(1H, m), 5.02(2H, s), 6.69–6.75(2H, m), 6.94–7.00 (2H, m), 7.63(1H, d, J = 8.8Hz), 7.83–7.87(2H, m), 8.03–8.06(1H, m), 8.12(1H, d, J = 8.8Hz), 8.50 (0.4H, s), 8.56(0.6H, s), 8.75(0.6H, s), 8.92(0.4H, s), 9.43–9.48(3H, m), 9.61–9.64(2H, m) |
| 66 | NMR(DMSO-$d_6$) δ: 1.78–1.85(2H, m), 2.04(2H, s), 2.25(1H, s), 3.04–3.07(2H, m), 3.49–3.75(8H, m), 5.02(2H, s), 6.69–6.73(2H, m), 6.83(1H, s), 6.99–7.04(2H, m), 7.41(1H, s), 7.61–7.65(1H, m), 7.80–7.84(1H, m), 7.92(0.7H, s), 7.94(0.3H, s), 8.01(1H, d, J = 8.8Hz), 8.12(1H, d, J = 8.8Hz), 8.46(0.3H, s), 8.50(0.7H, s), 8.67(0.7H, s), 8.81(0.3H, s), 9.34(2H, s), 9.38–9.41(1H, m), 9.55–9.57(2H, m) |
| 67 | NMR(DMSO-$d_6$) δ: 0.96–1.00(3H, m), 1.78–1.86(2H, m), 2.04(2H, s), 2.25(1H, s), 3.00–3.07(4H, m), 3.43–3.56(4H, m), 3.57–3.74(4H, m), 5.01(2H, s), 6.68–6.72(2H, m), 6.98–7.03(2H, m), 7.61–7.65 (1H, m), 7.79–7.82(1H, m), 7.88–7.92(2H, m), 8.03(1H, d, J = 8.8Hz), 8.12(1H, d, J = 8.7Hz), 8.44 (0.3H, s), 8.47(0.7H, s), 8.61(0.7H, s), 8.74(0.3H, s), 9.25(2H, s), 9.30–9.33(1H, m), 9.53(2H, s) |
| 68 | NMR(DMSO-$d_6$) δ: 0.78(1.2H, t, J = 7.2Hz), 0.84(1.8H, t, J = 7.2Hz), 0.95–1.00(3H, m), 1.74–1.85 (2H, m), 2.07(1.8H, s), 2.25(1.2H, s), 3.00–3.10(2H, m), 3.17–3.27(4H, m), 3.44–3.54(4H, m), 3.56–3.74(4H, m), 5.01(2H, s), 6.65–6.71(2H, m), 6.96–7.00(2H, m), 7.67–7.72(1H, m), 7.80–7.84(1H, m), 7.89(0.6H, s), 7.92(0.4H, s), 8.02(0.6H, s), 8.05(0.4H, s), 8.11(0.6H, s), 8.13(0.4H, s), 8.43(0.4H, s), 8.48(0.6H, s), 8.66(0.6H, s), 8.80(0.4H, s), 9.29(2H, s), 9.37–9.39(1H, m), 9.53–9.55(2H, m) |
| 69 | NMR(DMSO-$d_6$) δ: 1.15(3H, m), 1.79–1.88(2H, m), 2.03(2H, s), 2.26(1H, s), 3.48–3.61(4H, m), 3.65–3.78(4H, m), 4.10(2H, q, J = 6.9Hz), 4.98(2H, s), 6.65–6.72(2H, m), 6.96–7.06(2H, m), 7.59 (1H, d, J = 8.8Hz), 7.82(1H, dd, J = 1.9Hz, 8.8Hz), 7.85(1H, s), 8.03(1H, d, J = 8.8Hz), 8.11(1H, d, J = 8.8Hz), 8.52(1H, d, J = 8.8Hz), 8.63(0.7H, s), 8.77(0.3H, s), 9.30(3H, s), 9.53(3H, s) |
| 70 | NMR(DMSO-$d_6$) δ: 1.22(3H, t, J = 7.3Hz), 1.77–1.87(2H, m), 2.06(0.7H, s), 2.27(0.3H, s), 3.46–3.79 (8H, m), 4.11(2H, q, J = 7.3Hz), 4.23(2H, d, J = 5.9Hz), 5.60(2H, s), 6.73 6.8l (2H, m), 6.93–7.00 (2H, m), 7.09(0.7H, tJ = 5.8Hz, z), 7.15(0.3H, tJ = 5.8Hz), 7.70(1H, d, J = 8.3Hz), 7.80–7.85(1H, m), 7.83(1H, s), 7.99–8.40(1H, m), 8.11(1H, d, J = 8.8Hz), 8.47(0, 3H, s), 8.53(0.7H, s), 8.70(0.7H, s), 8.80(0.3H, s), 9.32(2H, s), 9.41–9.46(1H, m), 9.51–9.80(2H, m) |
| 71 | NMR(DMSO-$d_6$) δ: 1.79–1.88(2H, m), 2.05(2H, s), 2.26(1H, s), 3.49–3.79(8H, m), 3.89(1.3H, s), 3.91 (0.7H, s), 5.05(2H, s), 6.71–6.78(2H, m), 7.05–7.12(2H, m), 7.59–7.64(1H, m), 7.80–7.85(1H, m), 7.91(1H, d, J = 8.8Hz), 8.03(1H, dd, J = 1.4Hz, 8.8Hz), 8.12(1H, d, J = 8.8Hz), 8.51(0.3H, s), 8.55 (0.7H, s), 8.66(0.7H, s), 8.81(0.3H, s), 9.29–9.37(3H, m), 9.53–9.58(2H, m) |

TABLE 22

| Ex | DATA |
|---|---|
| 72 | NMR(DMSO-d$_6$) δ: 1.14–1.18(3H, m), 1.78–1.86(2H, m), 2.14(1.8H, s), 2.27(1.2H, s), 3.35(1.2H, s), 3.37(0.8H, s), 3.56–3.61(2H, m), 3.66–3.94(6H, m), 4.01–4.07(2H, m), 5.05(2H, s), 6.89–6.95 (1H, m), 7.50–7.53(1H, m), 7.63(1H, d, J = 8.4Hz), 7.84–7.93(3H, m), 8.04–8.08(1H, m), 8.13 (1H, d, J = 8.4Hz), 8.52(0.4H, s), 8.56(0.6H, s), 8.84(0.6H, s), 8.93(0.4H, s), 9.44(2H, s), 9.53–9.56 (1H, m), 9.64(2H, s) |
| 73 | NMR(DMSO-d$_6$) δ: 1.19(3H, t, J = 6.8Hz), 1.80–1.87(2H, m), 2.13(1.8H, s), 2.27(1.2H, s), 2.33–2.41 (2H, m), 2.55–2.61(2H, m), 3.58–3.62(2H, m), 3.68–3.95(6H, m), 4.07(2H, q, J = 6.8Hz), 5.24(2H, s), 6.91–6.97(1H, m), 7.51–7.61(2H, m), 7.83–7.88(2H, m), 7.93(1H, dd, J = 2.4Hz, 12.8Hz), 8.04 (1H, dd, J = 3.2Hz, 8.8Hz), 8.12(1H, d, J = 8.8Hz), 8.52(0.4H, s), 8.55(0.6H, s), 8.81(0.6H, s), 8.90 (0.4H, s), 9.42(2H, s), 9.52(0.4H, s), 9.56(0.6H, s), 9.62(2H, s) |
| 74 | NMR(DMSO-d$_6$) δ: 2.02–2.09(2H, m), 3.01–3.09(2H, m), 3.09–3.16(2H, m), 3.40–3.45(2H, m), 3.63–3.69(2H, m), 4.18(2H, q, J = 5.4Hz), 5.62(2H, s), 6.75(2H, d, J = 8.7Hz), 6.97–7.03(2H, m), 7.69 (1H, d, J = 8.7Hz), 7.80(1H, d, J = 8.7Hz), 7.92(1H, s), 8.01(1H, d, J = 8.7Hz), 8.10(1H, d, J = 8.7Hz), 8.44(1H, s), 9.11–9.19(4H, m), 9.47(2H, s), 12.53(1H, br) |
| 75 | NMR(DMSO-d$_6$) δ: 1.78–1.88(2H, m), 2.07(0.7H, s), 2.26(0.3H, s), 3.45–3.76(8H, s), 4.18(2H, d, J = 5.4Hz), 5.60(2H, s), 6.74–6.81(2H, m), 6.94(1H, t, J = 5.4Hz), 6.95–7.02(2H, m), 7.68(1H, d, J = 8.3 Hz), 7.79–7.83(1H, m), 7.92(1H, s), 7.99–8.03(1H, m), 8.11(1H, d, J = 8.3Hz), 8.45(0.3H, s), 8.50 (0.7H, s), 8.64(0.7H, s), 8.76(0.3H, s), 9.24(2H, s), 9.34(1H, s), 9.48–9.54(2H, m), 12.56(1H, br) |
| 76 | NMR(DMSO-d$_6$) δ: 2.73(3H, s), 3.01–3.11(2H, m), 3.31–3.33(6H, m), 3.52–3.55(2H, m), 4.23(2H, s), 5.02(2H, s), 6.66(2H, d, J = 8.8Hz), 7.22(2H, d, J = 8.8Hz), 7.67(1H, d, J = 8.8Hz), 7.80(1H, dd, J = 2.0Hz, 8.8Hz), 7.92(1H, s), 8.02(1H, d, J = 8.8Hz), 8.10(1H, d, J = 8.8Hz), 8.47(1H, s), 9.20(2H, s), 9.47(2H, s), 10.73(1H, s) |
| 77 | NMR(DMSO-d$_6$) δ: 0.87(3H, t, J = 7.4Hz), 1.22–1.31(2H, m), 1.59–1.71(2H, m), 2.06–2.14(1H, m), 2.32–2.43(1H, m), 2.95–3.05(4H, m), 3.25–3.47(4H, m), 3.69–3.74(2H, m), 4.24(2H, s), 5.02(2H, s), 6.66(2H, d, J = 9.2Hz), 7.22(2H, d, J = 9.2Hz), 7.67(1H, dd, J = 1.2Hz, 8.8Hz), 7.82(1H, dd, J = 1.2Hz, 8.8Hz), 7.91(1H, s), 8.02(1H, d, J = 8.8Hz), 8.10(1H, d, J = 8.8Hz), 8.49(1H, s), 9.32(2H, s), 9.53(2H, s), 10.96(1H, s) |
| 78 | NMR(DMSO-d$_6$) δ: 2.08–2.16(1H, m), 2.38–2.49(1H, m), 2.92–3.02(2H, m), 3.24–3.46(4H, m), 3.72–3.77(2H, m), 4.23(2H, s), 4.25–4.35(2H, m), 5.02(2H, s), 6.65(2H, d, J = 8.8Hz), 7.21(2H, d, J = 8.8Hz), 7.41–7.44(3H, m), 7.60–7.64(2H, m), 7.67(1H, dd, J = 1.5Hz, 8.8Hz), 7.82(1H, dd, J = 1.2Hz, 8.8Hz), 7.90(1H, s), 8.02(1H, d, J = 8.8Hz), 8.10(1H, d, J = 8.8Hz), 8.49(1H, s), 9.32(2H, s), 9.53(2H, s), 11.35(1H, s) |
| 79 | NMR(DMSO-d$_6$) δ: 1.79–1.84(1H, m), 3.35–3.39(2H, m), 3.45–3.49(2H, m), 3.52–3.55(2H, m), 3.58–3.62(2H, m), 4.26(2H, s), 5.00(2H, s), 6.70(2H, d, J = 8.8Hz), 7.19(2H, d, J = 8.8Hz), 7.51(4H, s), 7.65 (1H, dd, J = 1.0Hz, 8.8Hz), 7.83(1H, dd, J = 0.9Hz, 8.8Hz), 7.91(1H, s), 8.03(1H, d, J = 8.8Hz), 8.10 (1H, d, J = 8.8Hz), 8.51(1H, s), 9.38(2H, s), 9.56(2H, s) |
| 80 | NMR(DMSO-d$_6$) δ: 1.98–2.05(2H, m), 3.06–3.17(4H, m), 3.54–3.58(2H, m), 3.81–3.85(2H, m), 4.33 (2H, s), 5.03(2H, s), 6.68(1H, d, J = 9.2Hz), 7.59(1H, dd, J = 2.8Hz, 9.2Hz), 7.66–7.69(1H, m), 7.79–7.82(1H, m), 7.95(1H, m), 8.02–8.05(2H, m), 8.11(1H, d, J = 8.4Hz), 8.49(1H, s), 9.09(2H, s), 9.21 (2H, s), 9.48(2H, s) |
| 81 | NMR(DMSO-d$_6$) δ: 2.06–2.12(2H, m), 3.12–3.22(4H, m), 3.31(2H, s), 3.66–3.70(2H, m), 3.95–3.98 (2H, m), 5.06(2H, s), 7.01(1H, d, J = 9.2Hz), 7.62–7.66(2H, m), 7.84(1H, dd, J = 1.2Hz, 8.4Hz), 7.93–7.95(2H, m), 8.05(1H, d, J = 8.0Hz), 8.13(1H, d, J = 8.8Hz), 8.50(1H, s), 9.40(2H, s), 9.60(4H, s) |
| 82 | NMR(DMSO-d$_6$) δ: 1.79–1.86(2H, m), 2.13(1.8H, s), 2.27(1.2H, s), 3.27(1.2H, s), 3.28(0.8H, s), 3.56–3.62(2H, m), 3.68–3.92(6H, m), 5.04(2H, s), 6.88–6.94(1H, m), 7.49–7.56(1H, m), 7.63 (1H, d, J = 8.4Hz), 7.83–7.86(1H, m), 7.90–7.94(2H, m), 8.03–8.06(1H, m), 8.13(1H, d, J = 8.8Hz), 8.50(0.4H, s), 8.54(0.6H, s), 8.79(0.6H, s), 8.88(0.4H, s), 9.40(2H, s), 9.48(1H, s), 9.61(2H, s) |

TABLE 23

| Ex | DATA |
|---|---|
| 83 | NMR(DMSO-d$_6$) δ: 2.06–2.12(2H, m), 2.36(2H, t, J = 6.4Hz), 2.52(2H, t, J = 6.4Hz), 3.12–3.22(4H, m), 3.65–3.69(2H, m), 3.93–3.97(2H, m), 5.26(2H, s), 6.97–7.02(1H, m), 7.59–7.67(2H, m), 7.83 (1H, dd, J = 2.0Hz, 8.8Hz), 7.89(1H, s), 7.96(1H, d, J = 2.4Hz), 8.02(1H, d, J = 8.8Hz), 8.12(1H, d, J = 8.8Hz), 8.50(1H, s), 9.38(2H, s), 9.51(2H, s), 9.58(2H, s) |
| 84 | NMR(DMSO-d$_6$) δ: 1.81–1.87(2H, m), 2.14(2H, s), 2.28(1H, s), 2.31–2.37(2H, m), 2.51–2.55(2H, m), 3.59–3.63(2H, m), 3.70–3.96(6H, m), 5.03(2H, s), 6.94–7.00(1H, m), 7.55–7.61(2H, m), 7.83–7.90 (2H, m), 7.00(1H, dd, J = 2.4Hz, 12.0Hz), 8.03(1H, d, J = 8.8Hz), 8.12(1H, d, J = 8.8Hz), 8.52(0.3H, s), 8.55(0.7H, s), 8.82(0.7H, s), 8.91(0.3H, s), 9.44(2H, s), 9.53(0.3H, s), 9.57(0.7H, s), 9.63(2H, s) |
| 85 | NMR(DMSO-d$_6$) δ: 1.86–1.94(2H, m), 2.81–2.84(2H, m), 2.93–2.97(2H, m), 3.09(3H, s), 3.34–3.37 (4H, m), 3.48–3.51(2H, m), 4.97(2H, s), 6.60(2H, d, J = 9.0Hz), 7.17(2H, d, J = 9.0Hz), 7.67 (1H, d, J = 8.8Hz), 7.79(1H, d, J = 8.8Hz), 7.91(1H, s), 8.01(1H, d, J = 8.8Hz), 8.09(1H, d, J = 8.8Hz), 8.46(1H, s), 9.27(2H, s), 9.46(2H, s) |
| 86 | NMR(DMSO-d$_6$) δ: 0.96(6H, s), 2.86–2.89(2H, m), 3.09(3H, s), 3.28–3.33(2H, m), 3.35(2H, s), 3.35 (2H, t, J = 5.4Hz), 4.99(2H, s), 6.74(2H, d, J = 8.8Hz), 7.19(2H, d, J = 8.8Hz), 7.67(1H, dd, J = 1.4Hz, 8.8Hz), 7.83(1H, dd, J = 1.9Hz, 8.8Hz), 7.91(1H, s), 8.01(1H, d, J = 8.8Hz), 8.09(1H, d, J = 8.8Hz), 8.51(1H, s), 9.37(4H, s), 9.56(2H, s) |
| 87 | NMR(DMSO-d$_6$) δ: 0.89(3H, s), 0.92(3H, s)2.25(1.5H, s), 2.29(1.5H, s), 3.09(3H, s), 3.30(1H, s), 3.34(1H, s), 3.43–3.54(4H, m), 3.81–3.86(2H, m), 4.99(2H, s), 6.68(1H, d, J = 9.2Hz), 6.72 (1H, d, J = 9.2Hz), 7.16–7.21(2H, m), 7.65–7.68(1H, m), 7.84(1H, dd, J = 1.6Hz, 8.4Hz), 7.90(1H, s), |

TABLE 23-continued

| Ex | DATA |
|---|---|
| | 8.01(1H, d, J = 8.4Hz), 8.09(1H, d, J = 8.4Hz), 8.52(1H, s), 8.88(0.5H, s), 8.91(0.5H, s), 9.43–9.47 (3H, m), 9.59(2H, s) |
| 88 | NMR(DMSO-$d_6$) δ: 1.98–2.08(m, 2H), 3.07(s, 3H), 3.05–3.13(m, 2H), 3.15–3.22(m, 2H), 3.40–3.45 (m, 2H), 3.61–3.68(m, 2H), 4.99(s, 2H), 6.71(d, 2H, J = 8.8Hz), 6.89(s, 1H), 7.20(d, 2H, J = 9.3Hz), 7.70(dd, 1H, J = 1.9Hz, 8.8Hz), 7.82(d, 1H, J = 8.8Hz), 8.05(d, 1H, J = 1.5Hz), 8.84–8.91(m, 2H), 8.95 (s, 2H), 9.25(s, 2H) |
| 89 | NMR(DMSO-$d_6$) δ: 1.80–1.89(m, 2H), 2.04(s, 2H), 2.26(s, 1H), 3.08(s, 3H), 3.48–3.58(m, 4H), 3.58–3.64(m, 1H), 3.65–3.78(m, 3H), 4.99(s, 2H), 6.72(d, 0.6H, J = 9.3Hz), 6.74(d, 1.4H, J = 9.3Hz), 6.86 (s, 0.7H), 6.88(s, 0.3H), 7.18(d, 1.4H, J = 8.8Hz), 7.18(d, 0.6H, J = 8.9Hz), 7.72(dd, 1H, J = 2.0Hz, 8.8Hz), 7.82(d, 1H, J = 8.8Hz), 8.08(d, 0.3H, J = 1.9Hz), 8.11(d, 0.7H, J = 1.4Hz), 8.62(s, 0.7H), 8.76 (s, 0.3H), 9.12(s, 2H), 9.26–9.32(m, 1H), 9.32–9.42(m, 2H) |
| 90 | NMR(DMSO-$d_6$) δ: 1.82–1.89(2H, m), 3.42–3.46(2H, m), 3.59–3.64(4H, m), 3.83–3.87(2H, m), 4.22 (2H, s), 4.98(2H, s), 6.69(2H, d, J = 8.8Hz), 7.03–7.09(2H, m), 7.16(2H, m), 7.60(1H, dd, J = 1.6Hz, 8.4Hz), 7.74(1H, dd, J = 1.6Hz, 8.4Hz), 7.87(1H, s), 8.00(1H, d, J = 8.4Hz), 8.09(1H, d, J = 8.4Hz), 8.12–8.16(2H, m), 8.38(1H, s), 13.86(1H, s) |
| 91 | NMR(DMSO-$d_6$) δ: 2.06–2.13(1H, m), 2.28–2.42(1H, m), 3.70(1.5H, s), 2.72(1.5H, s), 2.99–3.08 (2H, m), 3.26–3.40(4H, m), 3.62–3.76(2H, m), 4.24(2H, s), 5.02(2H, s), 6.66(2H, d, J = 9.2Hz), 7.22, (2H, d, J = 9.2Hz), 7.66(1H, dd, J = 1.6Hz, 8.4Hz), 7.73(1H, dd, J = 1.6Hz, 8.4Hz), 7.89(1H, s), 8.01 (1H, d, J = 8.8Hz), 8.08(1H, d, J = 8.8Hz), 8.38(1H, s), 8.96–9.50(2H, br), 11.24(1H, s) |
| 92 | NMR(DMSO-$d_6$) δ: 1.98–2.05(2H, m), 2.55(3H, s), 2.89–3.00(4H, m), 3.28–3.33(2H, m), 3.52–3.55 (2H, m), 3.64(3H, s), 3.92(2H, s), 5.01(2H, s), 6.60(2H, d, J = 8.8Hz), 7.25(2H, d, J = 8.8Hz), 7.57 (1H, d, J = 7.2Hz), 7.81(1H, s), 7.89–7.94(2H, m), 8.00(1H, dd, J = 2.0Hz, 8.8Hz), 8.51(1H, s), 9.20 (2H, s) |
| 93 | NMR(DMSO-$d_6$) δ: 2.00–2.10(2H, m), 3.00–3.08(2H, m), 3.08–3.16(2H, m), 3.38–3.45(2H, m), 3.60–3.70(2H, m), 4.24(2H, s), 5.01(2H, s), 6.68(2H, d, J = 8.8Hz), 7.21(2H, d, J = 8.8Hz), 7.65 (1H, dd, J = 1.6Hz, 8.8Hz), 7.73(1H, dd, J = 1.6Hz, 8.8Hz), 7.89(1H, s), 8.01(1H, d, J = 8.8Hz), 8.08 (1H, d, J = 8.8Hz), 8.37(1H, s), 9.33(4H, br), 11.43(1H, br) |
| 94 | NMR(DMSO-$d_6$) δ: 2.02–2.14(1H, m), 2.25–2.35(1H, m), 2.72(3H, d, J = 4.9Hz), 2.96–3.08(2H, m), 3.24–3.44(4H, m), 3.59–3.74(2H, m), 4.87(2H, s), 6.62(2H, d, J = 9.0Hz), 7.18(2H, d, J = 9.0Hz), 7.67–7.74(2H, m), 7.91(1H, br s), 7.98(1H, d, J = 8.6Hz), 8.07(1H, d, J = 8.6Hz), 8.33(1H, br s) |

TABLE 24

| Ex | DATA |
|---|---|
| 95 | NMR(DMSO-$d_6$) δ: 1.26(3H, t, J = 6.8Hz), 1.83–1.90(2H, m)3.33–3.37(2H, m), 3.39–3.43(2H, m), 3.52–3.56(2H, m), 3.62–3.66(2H, m), 4.23(2H, 1, J = 6.8Hz), 4.33(2H, s), 4.93(2H, s), 5.94(2H, s), 6.66(2H, d, J = 9.2Hz), 6.71(2H, d, J = 6.4Hz), 7.13(2H, d, J = 9.2Hz), 7.43(1H, dd, J = 1.6Hz, 8.8Hz), 7.69(1H, s), 7.82–7.85(3H, m), 8.06(2H, d, J = 9.2Hz), 8.13(1H, s), 9.79(1H, s) |
| 96 | NMR(DMSO-$d_6$) δ: 1.27(3H, t, J = 7.2Hz), 1.93–2.01(2H, m), 2.42(3H, s), 2.68–2.83(2H, m), 2.95–3.03 (4H, m), 3.50–3.53(2H, m), 4.24(2H, q, J = 7.2Hz), 4.34(2H, s), 4.95(2H, s), 5.91(2H, s), 6.61(2H, d, J = 9.2Hz), 7.16(2H, d, J = 9.2Hz), 7.46(1H, dd, J = 1.6Hz, 8.0Hz), 7.71(1H, s), 7.81–7.82(2H, m), 7.85 (1H, d, J = 8.0Hz), 8.14(1H, s), 9.77(1H, s) |
| 97 | NMR(DMSO-$d_6$) δ: 1.27(3H, t, J = 6.8Hz), 2.00–2.04(2H, m), 2.98–3.08(2H, m), 3.08–3.17(2H, m), 3.38–3.45(2H, m), 3.60–3.70(2H, m), 4.24(2H, q, J = 6.8Hz), 4.36(2H, s), 5.01(2H, s), 6.69(2H, d, J = 8.8Hz), 7.21(2H, d, J = 8.8Hz), 7.65(1H, dd, J = 1.6Hz, 8.8Hz), 7.73(1H, dd, J = 1.6Hz, 8.8Hz), 7.89 (1H, s), 8.02(1H, d, J = 8.8Hz), 8.08(1H, d, J = 8.8Hz), 8.38(1H, s), 9.37(4H, br), 11.42(1H, br) |
| 98 | NMR(DMSO-$d_6$) δ: 2.08–2.25(2H, m), 2.67(3H, d), 2.77(3H, d), 3.00–3.15(2H, m), 3.25–3.72(6H, m), 4.92(2H, s), 6.62(2H, d), 7.17(2H, d), 7.28(1H, q), 7.64(1H, d), 7.71(1H, d), 7.91(1H, s), 7.97(1H, d), 8.04(1H, d), 8.29(1H, s), 10.45–10.60(1H, brs) |
| 99 | NMR(DMSO-$d_6$) δ: 2.04–2.14(1H, m), 2.22–2.34(1H, m), 2.73(3H, d), 2.78(6H, s), 2.99–3.10(2H, m), 3.25–3.43(3H, m), 3.56–3.92(3H, m), 4.99(2H, s), 6.63(2H, d), 7.21(2H, d), 7.65(1H, dd), 7.72 (1H, dd), 7.87(1H, s), 8.00(1H, d), 8.07(1H, d), 8.85–9.35(1H, br), 10.82–10.94(1H, brs), 11.20–11.42(1H, brs) |
| 100 | NMR(DMSO-$d_6$) δ: 2.04–2.12(1H, m), 2.27–2.39(1H, m), 2.71(1.5H, s), 2.72(1.5H, s), 2.98–3.08 (5H, m), 3.23–3.42(4H, m), 3.60–3.75(2H, m), 4.58–4.88(1H, br), 4.99(2H, s), 6.65(2H, d, J = 8.8Hz), 7.23(2H, d, J = 8.8Hz), 7.66(1H, dd, J = 2.0Hz, 8.4Hz), 7.72(2H, dd, J = 1.6Hz, 8.4Hz), 7.90(1H, s), 8.00(1H, d, J = 8.8Hz), 8.07(1H, d, J = 8.8Hz), 8.38(1H, s), 11.09(1H, s) |
| 101 | NMR(DMSO-$d_6$) δ: 1.24(3H, t, J = 7.1Hz), 1.93–2.03(2H, m), 2.52–2.58(3H, m), 2.88–3.05(6H, m), 3.10–3.20(2H, m), 4.08(2H, q, J = 7.1Hz), 5.07(2H, s), 5.90(2H, s), 6.53(2H, d, J = 8.8Hz), 7.07(2H, d, J = 8.8Hz), 7.49(1H, dd, J = 1.5Hz, 8.3Hz), 7.69(1H, br s), 7.77–7.83(3H, m), 8.09(1H, s), 9.74(1H, s) |
| 102 | NMH(DMSO-$d_6$) δ: 2.04–2.15(1H, m), 2.27–2.40(1H, m), 2.71(3H, d, J = 4.8Hz), 2.94–3.11(2H, m), 3.25–3.47(4H, m), 3.60–3.75(2H, m), 3.91(3H, s), 4.88(2H, s), 6.62(2H, d, J = 9.2Hz), 7.18(2H, d, J = 9.2Hz), 7.73–7.80(2H, m), 7.96(1H, s), 8.00(1H, d, J = 7.6Hz), 8.08(1H, d, J = 7.6Hz), 8.43(1H, s), 10.65(1H, brs), 11.31(1H, brs), 11.63(1H, brs) |
| 103 | NMR(DMSO-$d_6$) δ: 1.27(3H, t, J = 7.2Hz), 1.85–1.93(2H, m), 2.34(3H, s), 2.52–2.75(2H, m), 3.32–3.35(4H, m), 3.45–3.49(2H, m), 3.65(3H, s), 4.24(2H, q, J = 7.2Hz), 4.35(2H, s), 4.98(2H, s), 6.60 (2H, d, J = 8.8Hz), 7.16(2H, d, J = 8.8Hz), 7.57(1H, dd, J = 1.2Hz, 8.8Hz), 7.82(1H, s), 7.92–7.95 (2H, m), 8.01(1H, dd, J = 1.6Hz, 8.8Hz), 8.52(1H, s), 9.17(2H, s) |
| 104 | NMR(DMSO-$d_6$ δ: 2.02–2.15(1H, m), 2.30–2.40(1H, m), 2.67(3H, s), 2.71(3H, d, J = 4.9Hz), 2.98–3.10(2H, m), 3.24–3.44(4H, m), 3.60–3.75(2H, m), 3.92(3H, s), 4.94(2H, s), 6.63(2H, d, J = 9.0Hz), 7.18(2H, d, J = 9.0Hz), 7.69(1H, dd, J = 1.6Hz, 8.7Hz), 7.78(1H, dd, J = 1.6Hz, 8.7Hz), 7.93(1H, brs), 8.01(1H, d, J = 8.3Hz), 8.08(1H, d, J = 8.3Hz), 8.45(1H, brs), 10.65(1H, s), 11.34(1H, brs), 11.65 (1H, s) |

TABLE 24-continued

| Ex | DATA |
|---|---|
| 105 | NMR(DMSO-$d_6$) δ: 1.76–1.86(2H, m), 2.19(3H, s), 2.35–2.42(2H, m), 2.75(3H, s), 3.32(6H, s), 3.37–3.44(2H, m), 3.64(4H, s), 4.93(2H, s), 6.55(2H, d, J = 9.1Hz), 7.12(2H, d, J = 9.1Hz), 7.47–7.59(1H, m), 7.80(1H, brs), 7.91–8.03(3H, m), 8.51(1H, s), 9.17(1H, brs) |
| 106 | NMR(DMSO-$d_6$) δ: 2.04–2.15(2H, m), 2.25–2.35(1H, m), 2.73(3H, d, J = 4.3Hz), 3.02–3.10(2H, m), 3.04(3H, s), 3.25–3.75(6H, m), 3.91(3H, s), 5.00(2H, s), 6.65(2H, d, J = 9.1Hz), 7.23(2H, d, J = 9.1Hz), 7.69(1H, dd, J = 1.5Hz, 8.3Hz), 7.78(1H, dd, J = 1.5Hz, 8.3Hz), 7.78(1H, dd, J = 1.5Hz, 8.3Hz), 7.94 (1H, brs), 8.02(1H, d, J = 8.6Hz), 8.08(1H, d, J = 8.6Hz), 8.46(1H, brs), 10.16(1H, brs), 10.91(1H, brs) |
| 107 | NMR(DMSO-$d_6$) δ: 1.23(3H, t, J = 7.1Hz), 1.91(2H, brs), 2.54(3H, s), 2.65(2H, brs), 2.84(2H, brs), 2.93(2H, brs), 3.06(2H, brs), 3.64(3H, s), 4.04(2H, q, J = 7.0Hz), 5.10(2H, s), 6.47(2H, d, J = 8.8Hz), 7.07(2H, d, J = 8.8Hz), 7.62(1H, dd, J = 1.2Hz, 8.6Hz), 7.79(1H, brs), 7.87–7.99(3H, m), 8.46 (1H, brs), 9.16(1H, brs) |

TABLE 25

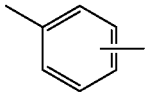

| Ex | R$^1$ | | X | Y | R$^2$ |
|---|---|---|---|---|---|
| 108 | —C(=NH)—Me | | —SO$_2$— | -4-Ph— | —COOH |
| 109 | —Me | | —SO$_2$— | -4-Ph— | —COOH |
| 110 | —C(=NH)—Me | | —SO$_2$— | -4-Ph— | —COOEt |
| 111 | —C(=NH)—Me | | —SO$_2$— | -4-Ph— | —COOH |
| 112 | —Me | | —SO$_2$— | -4-Ph— | —COOH |
| 113 | —C(=NH)—Me | | —SO$_2$— | -3-Ph | —COOH |
| 114 | —Me | | —SO$_2$— | -3-Ph— | —COOH |
| 115 | —C(=NH)—Me | | —CO— | -3-Ph | —COOH |
| 116 | —COOEt | | —SO$_2$— | —CH$_2$— | —COOH |
| 117 | —CONH$_2$ | | —SO$_2$— | —CH$_2$— | —COOH |
| 118 | —CONHMe | | —SO$_2$— | —CH$_2$— | —COOH |
| 119 | —CON(Me)$_2$ | | —SO$_2$— | —CH$_2$— | —COOH |
| 120 | —Me | | —CO— | —CH$_2$— | —COOH |
| 121 | —Me | | —CO— | —CH$_2$CH$_2$— | —COOH |
| 122 | —Me | | —CO— | —CH$_2$— | —COOH |
| 123 | —Me | | —SO$_2$— | —CH$_2$— | —COOEt |
| 124 | —Me | | —SO$_2$— | —CH$_2$CH$_2$— | —COOH |
| 125 | —C(=HN)—Me | | —CO— | —CH$_2$— | —COOH |
| 126 | —C(=HN)—Me | | —CO— | —CH$_2$CH$_2$— | —COOH |
| 127 | —C(=HN)—Me | | —SO$_2$— | —CH$_2$— | —COOH |
| 128 | —C(=HN)—Me | | —SO$_2$— | —CH$_2$— | —COOEt |
| 129 | —C(=HN)—Me | | —SO$_2$— | —CH$_2$CH$_2$— | —COOH |

TABLE 26

[Structure: benzamidine-B-CH2-N(X-Y-R2)-phenyl-N(homopiperazine)-R1]

B group: methyl-substituted bicyclic with benzofuran (2-methyl-6-yl benzofuran shown)

| Ex  | R¹        | X     | Y         | R²    |
|-----|-----------|-------|-----------|-------|
| 130 | —Me       | —CO—  | —CH₂—     | —COOH |
| 131 | —Me       | —CO—  | —CH₂CH₂—  | —COOH |
| 132 | —Me       | —SO₂— | —CH₂—     | —COOH |
| 133 | —Me       | —SO₂— | —CH₂—     | —COOH |
| 134 | —Me       | —SO₂— | —CH₂CH₂—  | —COOH |
| 135 | —C(=HN)—Me | —CO—  | —CH₂—    | —COOH |
| 136 | —C(=HN)—Me | —CO   | —CH₂CH₂— | —COOH |
| 137 | —C(=HN)—Me | —SO₂— | —CH₂—    | —COOH |
| 138 | —C(=HN)—Me | —SO₂— | —CH₂—    | —COOEt |
| 139 | —C(=HN)—Me | —SO₂— | —CH₂CH₂— | —COOH |

TABLE 27

[Same core structure as Table 26]

B group shown: 2-methylbenzothiazole and 2-methylindole

| Ex  | R¹        | X     | Y         | R²    |
|-----|-----------|-------|-----------|-------|
| 140 | —Me       | —CO—  | —CH₂—     | —COOH |
| 141 | —Me       | —CO—  | —CH₂CH₂—  | —COOH |
| 142 | —Me       | —SO₂— | —CH₂—     | —COOH |
| 143 | —Me       | —SO₂— | —CH₂—     | —COOEt |
| 144 | —Me       | —SO₂— | CH₂CH₂—   | —COOH |
| 145 | —C(=HN)—Me | —CO—  | —CH₂—    | —COOH |
| 146 | —C(=HN)—Me | —CO—  | —CH₂CH₂— | —COOH |
| 147 | —C(=HN)—Me | —SO₂— | —CH₂—    | —COOH |
| 148 | —C(=HN)—Me | —SO₂— | —CH₂—    | —COOEt |
| 149 | —C(=HN)—Me | —SO₂— | —CH₂CH₂— | —COOH |
| 150 | —Me       | —CO—  | —CH₂—     | —COOH |
| 151 | —Me       | —CO—  | —CH₂CH₂—  | —COOH |
| 152 | —Me       | —SO₂— | —CH₂—     | —COOH |
| 153 | —Me       | —SO₂— | CH₂—      | —COOEt |
| 154 | —Me       | —SO₂— | —CH₂CH₂—  | —COOH |
| 155 | —C(=HN)—Me | —CO—  | —CH₂—    | —COOH |
| 156 | —C(=HN)—Me | —CO—  | —CH₂CH₂— | —COOH |
| 157 | —C(=HN)—Me | —SO₂— | —CH₂—    | —COOH |
| 158 | —C(=HN)—Me | —SO₂— | —CH₂—    | —COOEt |
| 159 | —C(=HN)—Me | —SO₂— | —CH₂CH₂— | —COOH |

TABLE 27-continued

| Ex | B | R¹ | X | Y | R² |
|---|---|---|---|---|---|
| 160 | benzimidazole | —Me | —CO— | —CH₂— | —COOH |
| 161 | | —Me | —CO— | —CH₂CH₂— | —COOH |
| 162 | | —Me | —SO₂— | —CH₂— | —COOH |
| 163 | | —Me | —SO₂— | —CH₂— | —COOEt |
| 164 | | —Me | —SO₂— | —CH₂CH₂— | —COOH |
| 165 | | —C(=HN)—Me | —CO— | —CH₂— | —COOH |
| 166 | | —C(=HN)—Me | —CO— | —CH₂CH₂— | —COOH |
| 167 | | —C(=HN)—Me | —SO₂— | —CH₂— | —COCH |
| 168 | | —C(=HN)—Me | —SO₂— | —CH₂— | —COOEt |
| 169 | | —C(=HN)—Me | —SO₂— | —CH₂CH₂— | —COOH |
| 170 | quinoline | —Me | —CO— | —CH₂— | —COOH |
| 171 | | —Me | —CO— | —CH₂CH₂— | —COOH |
| 172 | | —Me | —SO₂— | —CH₂— | —COOH |
| 173 | | —Me | —SO₂— | —CH₂— | —COOEt |
| 174 | | —Me | —SO₂— | —CH₂CH₂— | —COOH |
| 175 | | —C(=HN)—Me | —CO— | —CH₂— | —COOH |
| 176 | | —C(=HN)—Me | —CO— | —CH₂CH₂— | —COOH |
| 177 | | —C(=HN)—Me | —SO₂— | —CH₂— | —COOH |
| 178 | | —C(=HN)—Me | —SO₂— | —CH₂— | —COOEt |
| 179 | | —C(=HN)—Me | —SO₂— | —CH₂CH₂— | —COOH |

What is claimed is:

1. A hexahydro-1,4-diazepine compound represented by the following formula (I) or its pharmaceutically acceptable salt:

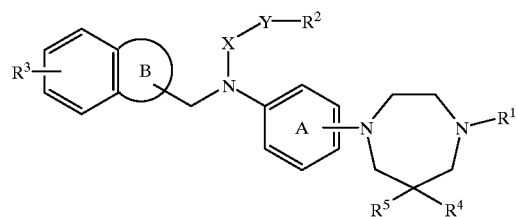

(I)

wherein the symbols have the following meanings:

A: a phenylene or pyridylene group (which may be substituted),

B: forming a 5- or 6-membered aryl or heteroaryl,

X: a group of formula, —CO—, —CONH—, —CSNH—, —SO₂—, —SO₂NH—, or —SO₂N(-lower alkyl)-, Y: a bond or a lower alkylene group, R¹: a hydrogen atom, or a lower alkyl, —L-aryl, —L-heteroaryl, —L—COO-R⁶, —L—CON(—R⁶)—R⁷, —C(=NH)—NH₂, or —C(=NH)-lower alkyl group, R²: a hydrogen atom, an —O-lower alkyl, —COOH, —COO-lower alkyl, —CONH₂, —CONH-lower alkyl, or —CON—di-lower alkyl group, or an aryl or heteroaryl group (which may be substituted), R³ an amidino group or a group capable of being converted into an amidino group in a living body, R⁴, R⁵: a hydrogen atom or a lower alkyl group, which may be the same or different, R⁶, R7: a hydrogen atom or a lower alkyl group, which may be the same or different, and L: a bond or a lower alkylene group.

2. The hexahydro-1,4-diazepine compound or its pharmaceutically acceptable salt as claimed in claim 1, wherein the ring

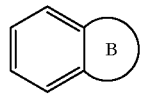

is naphthalene or benzofuran.

3. The hexahydro-1,4-diazepine compound or, its pharmaceutically acceptable salt as claimed in claim 2, wherein R⁴ and R⁵ are each a hydrogen atom.

4. The hexahydro-1,4-diazepine compound or its pharmaceutically acceptable salt as claimed in claim 3, wherein the ring

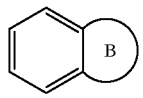

is naphthalene; A is a phenylene group (the phenylene group may be substituted with a substituent selected from a halogen atom, or an amino, cyano, nitro, —OH, —COOH, lower alkyl, —O-lower alkyl, or —COO-lower alkyl group), or a pyridylene group; and $R^3$ is an amidino group.

5. The hexahydro-1,4-diazepine compound or its pharmaceutically acceptable salt as claimed in claim 4, wherein A is a phenylene or pyridylene group; X is a group of formula, —CO—, —CSNH—, —SO$_2$—, or —SO$_2$NH—; $R^1$ is a hydrogen atom, or a lower alkyl, pyridyl, or —C(=NH)—CH$_3$ group; and $R^2$ is a hydrogen atom or a —COOH, —COO-lower alkyl, or tetrazolyl group.

6. A hexahydro-1,4-diazepine compound which is:
N-[4-(4-Acetimidoylhexahydro-1H-1,4-diazepin-1-yl)-phenyl]-N-[(7-amidino-2-naphthyl)methyl]acetamide,
ethyl [N-[4-(4-acetimidoylhexahydro-1H-1,4-diazepin-1-yl)phenyl]-N-[(7-amidino-2-naphthyl)methyl]-sulfamoyl]acetate,
ethyl N-[N-[4-(4-acetimidoylhexahydro-1H-1,4-diazepin-1-yl)phenyl]-N-[(7-amidino-2-naphthyl)methyl]-sulfamoyl]glycinate,
ethyl N-[4-(4-acetimidoylhexahydro-1H-1,4-diazepin-1-yl)phenyl]-N-[(7-amidino-2-naphthyl)methyl]malonamate,
[N-[6-(4-acetimidoylhexahydro-1H-1,4-diazepin-1-yl)-3-pyridyl]-N-[(7-amidino-2-naphthyl)methyl]sulfamoyl]acetic acid,
[N-[4-(4-acetimidoylhexahydro-1H-1,4-diazepin-1-yl)phenyl]-N-[(7-amidino-2-naphthyl)methyl]sulfamoyl]-acetic acid,
N-[4-(4-acetimidoylhexahydro-1H-1,4-diazepin-1-yl)phenyl]-N-[(7-amidino-2-naphthyl)methyl]succinamic acid,
ethyl N-[4-(4-acetimidoylhexahydro-1H-1,4-diazepin-1-yl)-3-pyridyl]-N-[(7-amidino-2-naphthyl)methyl]-malonamate,
ethyl N-[4-(4-acetimidoylhexahydro-1H-1,4-diazepin-1-yl)-3-pyridyl]-N-[(7-amidino-2-naphthyl)methyl]-succinamate,
N-[4-(4-acetimidoylhexahydro-1H-1,4-diazepin-1-yl)phenyl]-N-[(7-amidino-2-naphthyl)methyl]thioamido-acetic acid,
N-[4-(4-acetimidoylhexahydro-1H-1,4-diazepin-1-yl)-3-pyridyl]-N-[(7-amidino-2-naphthyl)methyl]succinamic acid, or pharmaceutically acceptable salts thereof.

7. A pharmaceutical composition containing the hexahydro-1,4-diazepine compound or its pharmaceutically acceptable salt as claimed in claim 1 and a pharmaceutically acceptable carrier.

8. The pharmaceutical composition as claimed in claim 7, which is an activated blood coagulation factor X inhibitor.

* * * * *